US007625880B2

(12) United States Patent
Jankowski et al.

(10) Patent No.: US 7,625,880 B2
(45) Date of Patent: Dec. 1, 2009

(54) INHIBITORS OF TYROSINE KINASES AND USES THEREOF

(75) Inventors: Orion D. Jankowski, Burlingame, CA (US); James T. Palmer, Corte Madera, CA (US); Lee Honigberg, San Francisco, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 124 days.

(21) Appl. No.: 11/617,651

(22) Filed: Dec. 28, 2006

(65) Prior Publication Data

US 2008/0039426 A1 Feb. 14, 2008

Related U.S. Application Data

(60) Provisional application No. 60/758,617, filed on Jan. 13, 2006.

(51) Int. Cl.
*A61K 31/675* (2006.01)
*C07D 403/00* (2006.01)
(52) U.S. Cl. .................... 514/79; 514/252.13; 544/359; 558/80
(58) Field of Classification Search ................. 544/359; 558/80; 514/252.13, 79
See application file for complete search history.

(56) References Cited

U.S. PATENT DOCUMENTS

| | | | |
|---|---|---|---|
| 6,326,469 B1 | 12/2001 | Ullrich et al. | |
| 6,506,769 B2 * | 1/2003 | Snow et al. ................. | 514/293 |
| 6,660,744 B1 | 12/2003 | Hirst et al. | |
| 6,753,348 B2 | 6/2004 | Uckun et al. | |
| 6,770,639 B2 | 8/2004 | Snow et al. | |
| 6,921,763 B2 | 7/2005 | Hirst et al. | |
| 2003/0040461 A1 | 2/2003 | McAtee | |
| 2003/0125235 A1 | 7/2003 | Foxwell | |
| 2005/0008640 A1 | 1/2005 | Waegell et al. | |
| 2005/0090499 A1 | 4/2005 | Currie et al. | |
| 2005/0101604 A1 | 5/2005 | Currie et al. | |
| 2005/0196851 A1 | 9/2005 | Uckun | |
| 2005/0209255 A1 | 9/2005 | Jimenez et al. | |
| 2006/0167090 A1 | 7/2006 | Uckun et al. | |

FOREIGN PATENT DOCUMENTS

| | | |
|---|---|---|
| WO | WO-97-028161 | 8/1997 |
| WO | WO-00-56737 A2 | 9/2000 |
| WO | WO-01-19829 A2 | 3/2001 |
| WO | WO-01-19829 A3 | 3/2001 |
| WO | WO-01-25238 A2 | 4/2001 |
| WO | WO-01-41754 | 6/2001 |
| WO | WO-01-44258 A1 | 6/2001 |
| WO | WO-02-38797 A2 | 5/2002 |
| WO | WO-02-080926 | 10/2002 |
| WO | WO-03-000187 | 1/2003 |
| WO | WO-2004-096253 | 11/2004 |
| WO | WO-2005-005429 | 1/2005 |
| WO | WO-2005-014599 | 2/2005 |

OTHER PUBLICATIONS

Snow et al., 2002, 136:151166.*
Browning, J.L., "B cells move to centre stage: novel opportunities for autoimmune disease treatment", Nature Reviews/Drug Discovery vol. 5, Jul. 2006, pp. 564-576.
Cohen, M.S. et al., "Structural Bioinformatics-Based Design of Selective, Irreversible Kinase Inhibitors," Science, vol. 308, May 27, 2005, pp. 1318-1321.
Desiderio, S., "Role of Btk in B cell development and signaling," Curr. Op. in Immunology 1997, 9:534-540.
Fruman, D.A., "Xid-like Phenotypes: A B Cell Signalosome Takes Shape," Immunity 13:1-3 (Jul. 2000).
Gold, Michael R., "To make antibodies or not:signaling by the B-cell antigen receptor," Trends in Pharmacological Sciences, 23(7):316-324 (Jul. 2002).
Horwood, Nicole J. et al., "Bruton's Tyrosin Kinase Is Required for Lipopolysaccharide—induced Tumor Necrosis Factor α Production," J. Exp. Med. 197(12):1603-1611 (Jun. 2003).
Iwaki, Shoki et al., "Btk Plays a Crucial Role in the Amplification of FceRI-mediated Mast Cell Activation by Kit," J. Biol. Chem. 280(48):40261-40270 (Dec. 2, 2005).
Jefferies, Caroline A. et al., "Bruton's Tyrosine Kinase Is a Toll/Interleukin-1 Receptor Domain-binding Protein That Participates in Nuclear Factor κB Activation by Toll-like Receptor 4," J. Biol. Chem. 278:26258-26264 (2003).
Kawakami, Yuko et al., "Terreic acid, a quinone epoxide inhibitor of Bruton's tyrosine kinase," PNAS USA 96:2227-2232 (1999).
Kuppers, R., "Mechanisms of B-cell lymphoma pathogenesis," Nature Reviews/Cancer, vol. 5, Apr. 2005, pp. 251-262.
Kurosaki, Tomohiro, "Functional dissection of BCR signaling pathways," Curr. Op. Imm. 12:276-281 (2000).
Mahajan, S. et al., "Rational Design and Synthesis of a Novel Antileukemic Agent Targeting Bruton's Tyrosine Kinase (BTK), LFM-A13 [α-Cyano-β-Methyl-N-(2,5-Dibromophenyl)Propenamide]," J. of Biol. Chem., vol. 274, No. 14, Apr. 2, 1999, pp. 9587-9599.
Mangla, Anita et al., "Pleiotropic consequences of Bruton tyrosin kinase deficiency in myeloid lineages lead to poor inflammatory responses," Blood 104(4):1191-1197 (2004).

(Continued)

*Primary Examiner*—Rei-tsang Shiao
(74) *Attorney, Agent, or Firm*—Wilson Sonsini Goodrich & Rosati

(57) ABSTRACT

Disclosed herein are compounds that inhibit the activity of particular tyrosine kinases. Methods for the preparation of such compounds are disclosed. Also disclosed are pharmaceutical compositions that include the compounds. Methods of using the compounds disclosed, alone or in combination with other therapeutic agents, for the treatment of tyrosine kinase-mediated diseases or conditions or tyrosine kinase-dependent diseases or conditions are provided.

20 Claims, No Drawings

OTHER PUBLICATIONS

Niiro, Hiroaki and Clark, Edward A., "Regulation of B-Cell Fate by Antigen-Receptor Signals," Nature Reviews 2:945-956 (2002).

Oligino, Thomas J. and Dalrymple, Stacie A., "Targeting B cells for the treatment of rheumatoid arthritis," Arthirits Res Ther 5(Suppl. 4):S7-S11 (2002).

Pan, Z. et al., "Discovery of Selectable Irreversible Inhibitors for Bruton's Tyrosine Kinase," ChemMedChem 2006, 1, 1-5.

Quek, L.S. et al., "A role for Bruton's tyrosine kinase (Btk) in platelet activation by collagen," Curr. Biol. 8(20):1137-1140 (1998).

Sada, Kiyonao and Yamamura, Hirohei, "Protein-Tyrosine Kinases and Adaptor Proteins in FceRI-Mediated Signaling in Mast Cells," Curr. Mol. Med. 3(1):85-94 (2003).

Schaeffer, Edward M. and Schwartzberg, Pamela L., "Tec family kinases in lymphocyte signaling and function," Curr. Op. Imm. 12:282-288 (2000).

Science IP CAS Search, Sep. 5, 2006.

Science IP CAS Search, Mar. 16, 2006.

Merged Markush Service Search, Jun. 27, 2005.

Shaffer, A.L. et al., Lymphoid malignancies: the dark side of B-cell differentiation, Nature Reviews/Immunology, vol. 2, Dec. 2002, pp. 920-932.

Smith, C.I. Edvard et al., "The Tec family of cytoplasmic tyrosine kinases: mammalian Btk, Bmx, Itk, Tec, Txk and homologs in other species," BioEssays 23:436-446 (2001).

Smolen, Josef S. And Steiner, Gunter, "Therapeutic Strategies for Rheumatoid Arthritis," Nature Reviews 2:473-488 (2003).

Uckun, Fatih. M. et al., "The Anti-leukemic Bruton's Tyrosin Kinase Inhibitor α-cyano-β-hydroxy-β-mehyl-N-(2,5-dibromophenyl)Propenamide (LFM-A13)Prevents Fatal Thromboembolism," Leuk. Lymphoma 44(9):1569-1577 (2003).

Uckun, Fatih M. et al., "In Vivo Pharmacokinetic Features, Toxicity Profile, and Chemosensitizing Activity of α-Cyano-β-hydroxy-β-methyl-N-(2,5-dibromophenyl)propenamide (LFM-A13), a Novel Antileukemic Agent Targeting Bruton's Tyrosine Kinase," Clin. Cancer Res. 8:1224-1233 (2002).

Uckun, F.M., "Bruton's Tyrosin Kinase (BTK) as a Dual-Function Regulator of Apoptosis," Biochem. Pharmacology, vol. 56, pp. 683-691, 1998.

Uckun, Fatih M. et al., "BTK as a Mediator of Radiation-Induced Apoptosis in DT-40 Lymphoma B Cells,"Science vol. 273 No. 5278, pp. 1096-1100 (1996).

Vassilev, A.O. And Uckun, F.M., "Therapeutic Potential of Inhibiting Bruton's Tyrosine Kinase, (BTK)," Current Pharmaceutical Design, 2004, 10, 1757-1766.

Vassilev,Alexei et al., "Bruton's Tyrosine Kinase as an Inhibitor of the Fas/CD95 Death-inducing Signaling Complex," J. Biol. Chem. 274(3):1646-1656 (1999).

Yamamoto, Noriyuki et al., "The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents," J. Pharma. And Exp. Therapeutics 306(3):1174-1181 (2003).

Luskova, P. And Draber, P., "Modulation of the Fce Receptor I Signaling by Tyrosin Kinase Inhibitors: Search for Therapeutic Targets of Inflammatory and Allergy Diseases," Curr. Pharmaceutical Design 10:1727-1737 (2004).

Arnold, L.D. et al., "Pyrrolo[2,3-d]pyrimidines Containing an Extended 5-Substituent as Potent and Selective Inhibitors of lck 1," Bioorg. Med. Chem. Ltrs. 10:2167-2170 (2000).

Burchat et al., "Pyrazolo[3,4-d]pyrimidines Containing an Extended 3-Substituent as Potent Inhibitors of Lck—a Selectivity Insight," Bioorg. Med. Chem. Ltrs. 12:1687-1690 (2002).

Nisitani, S. et al., "In situ detection of activated Bruton's tyrosine kinase in the Ig signaling complex by phosphopeptide-specific monoclonal antibodies," PNAS USA 96:2221-2226 (1999).

Smaill, J.B. et al., "Tyrosine Kinase Inhibitors. 15. 4-(Phenylamino)quinazoline and 4-(Phenylamino)prido[d]pyrimidine Acrylamides as Irresversible Inhibitors of the ATP Binding Site of the Epidermal Growth Factor Receptor," J. Med. Chem. 42(10):1803-1815 (1999).

* cited by examiner

INHIBITORS OF TYROSINE KINASES AND USES THEREOF

RELATED APPLICATIONS

This application claims benefit of U.S. Provisional Application No. 60/758,617 entitled "INHIBITORS OF TYROSINE KINASES" filed Jan. 13, 2006, which is herein incorporated by reference.

FIELD OF THE INVENTION

Described herein are compounds, methods of making such compounds, pharmaceutical compositions and medicaments containing such compounds, and methods of using such compounds and compositions to inhibit the activity of tyrosine kinases.

BACKGROUND OF THE INVENTION

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival (Kurosaki, *Curr Op Imm*, 2000, 276-281; Schaeffer and Schwartzberg, *Curr Op Imm* 2000, 282-288). In addition, Btk plays a role in a number of other hematopoetic cell signaling pathways, e.g., Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See, e.g., C. A. Jeffries, et al., (2003), *Journal of Biological Chemistry* 278:26258-26264; N. J. Horwood, et al., (2003), *The Journal of Experimental Medicine* 197:1603-1611; Iwaki et al. (2005), *Journal of Biological Chemistry* 280(48):40261-40270; Vassilev et al. (1999), *Journal of Biological Chemistry* 274(3):1646-1656, and Quek et al. (1998), *Current Biology* 8(20):1137-1140.

SUMMARY OF THE INVENTION

Compounds, compositions and methods for inhibiting the activity of a subset of tyrosine kinases (such as Btk) are provided. In one embodiment, compounds provided herein are used to inhibit Bruton's tyrosine kinase (Btk), and are thus inhibitors of Btk. Processes for the preparation of compounds that inhibit the activity of certain tyrosine kinases, compositions that include the compounds, as well as methods of use thereof are provided.

Compounds provided herein include those that have a structure of Formula (Ia), Formula (Ib), Formula (Ic), Formula (II), Formula (III), Formula (IIIa), Formula (IIIb), Formula (IIIc), Formula (IV), Formula (V), and/or Formula (VI), and pharmaceutically acceptable salts, solvates, esters, acids and prodrugs thereof. In certain embodiments, isomers and chemically protected forms of compounds having a structure represented by Formula (Ia), Formula (Ib), Formula (Ic), Formula (II), Formula (III), Formula (IIIa), Formula (IIIb), Formula (IIIc), Formula (IV), Formula (V), and/or Formula (VI), are also provided.

In one aspect, provided herein are compounds of Formula (III):

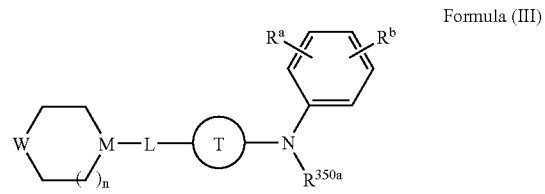

Formula (III)

wherein:
$R^a$ and $R^b$ are each independently selected from among H, halogen, CN, $NO_2$, $C_1$-$C_4$alkyl, $C_1$-$C_4$haloalkyl, and $C_1$-$C_4$alkoxy;
T is 1,6-dimethyl-9-oxo-8,9-dihydro-1H-imidazo[4,5-h]isoquinolin-2,7-ylene, or 1,7-dimethyl-9-oxo-8,9-dihydro-1H-imidazo[4,5-h]isoquinolin-2,6-ylene;
L is $-X^{250a}-Y^{250}-$ or $-Y^{250}-X^{250a}-$, wherein,
$X^{250a}$ is a substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;
$Y^{250}$ is a bond, $-O-$, $-S(=O)-$, $-S(=O)_2-$, $-C(=O)-$, $-NR^{45}-$, $-NH-$, $-NHC(=O)-$, $-NR^{45}C(=O)-$, $-NR^{45}C(=O)NR^{45}-$, $-C(=O)NH-$, $-C(=O)NR^{45}-$, $-OC(=O)-$, $-C(=O)O-$, $-NHSO_2-$, $-NR^{45}SO_2-$, $-SO_2NH-$, $-SO_2NR^{45}-$, $-C(R^{45})=NO-$, $-CH=NO-$, $-ON=CH-$, heteroaryl, aryl, $-NHC(=O)O-$, $-OC(=O)NH-$, $-NR^{45}C(=O)O-$, or $-OC(=O)NR^{45}-$;
where each $R^{45}$ is independently selected from among hydrogen, substituted or unsubstituted $C_1$-$C_6$alkyl, substituted or unsubstituted $C_3$-$C_8$cycloalkyl, substituted or unsubstituted $C_2$-$C_6$alkenyl, substituted or unsubstituted $C_2$-$C_6$alkynyl;
M is N or CH;
W is

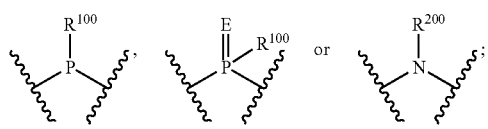

E is oxygen or sulfur;
$R^{100}$ is halogen, $-OH$, or an optionally substituted group selected from among $C_1$-$C_6$alkyl, $C_2$-$C_6$alkenyl, $C_2$-$C_6$alkynyl, phenyl, $C_1$-$C_4$alkyl (phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), heteroaryl, $C_1$-$C_4$alkyl (heteroaryl), $C_1$-$C_6$alkoxy, $C_1$-$C_6$alkenyloxy, $C_1$-$C_6$alkynyloxy, or $-NR^{102a}R^{102b}$;
$R^{102a}$ and $R^{102b}$ are independently hydrogen, or an optionally substituted group selected from among $C_1$-$C_6$alkyl, $C_2$-$C_6$alkenyl, $C_2$-$C_6$alkynyl, aryl, aralkyl, heteroaryl, heteroaralkyl, $C_3$-$C_8$cycloalkyl, $C_1$-$C_4$alkyl($C_3$-$C_8$cycloalkyl), $C_2$-$C_8$heterocycloalkyl, and $C_1$-$C_4$alkyl($C_2$-$C_8$heterocycloalkyl);

$R^{200}$ is an optionally substituted group selected from among $C_2$-$C_{10}$acyl, $C_2$-$C_6$alkenyl, $C_2$-$C_6$alkynyl, $C_3$-$C_6$cycloalkyl, $C_1$-$C_4$alkyl($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, di($C_1$-$C_6$alkyl)aminosulfonyl, and $C_1$-$C_6$alkylsulfonylamino;

$R^{350a}$ is hydrogen, a substituted or unsubstituted $C_1$-$C_6$alkyl, a substituted or unsubstituted $C_2$-$C_6$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl;

n is 0, 1, or 2; and pharmaceutically active metabolites, pharmaceutically acceptable solvates, pharmaceutically acceptable salts, or pharmaceutically acceptable prodrugs thereof.

For any and all of the embodiments, substituents can be selected from among from a subset of the listed alternatives. For example, in some embodiments, T is 1,6-dimethyl-9-oxo-8,9-dihydro-1H-imidazo[4,5-h]isoquinolin-2,7-ylene. In other embodiments, T is 1,7-dimethyl-9-oxo-8,9-dihydro-1H-imidazo[4,5-h]isoquinolin-2,6-ylene.

In some embodiments, T is 1,6-dimethyl-9-oxo-8,9-dihydro-1H-imidazo[4,5-h]isoquinolin-2,7-ylene substituted at the 2 position with

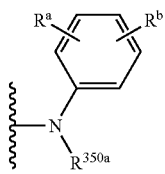

and substituted at the 7 position with

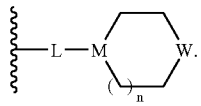

In other embodiment, $Y^{250}$ is a bond, —O—, —S(=O)—, —S(=O)$_2$—, —C(=O)—, —NH—, —NHC(=O)—, —NHC(=O)NH—, —C(=O)NH—, —OC(=O)—, —C(=O)O—, —NHSO$_2$—, —SO$_2$NH—, —NHC(=O)O—, or —OC(=O)NH—; E is O; and $R^{350a}$ is hydrogen, a substituted or unsubstituted $C_1$-$C_6$alkyl, or a substituted or unsubstituted $C_1$-$C_6$haloalkyl.

In some embodiments, $R^{350a}$ is hydrogen or a substituted or unsubstituted $C_1$-$C_6$alkyl. In yet other embodiments, $R^{350a}$ is hydrogen or a $C_1$-$C_6$alkyl. In yet other embodiments, $R^{350a}$ is hydrogen.

In some other embodiments, $X^{250a}$ is a substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl; and n is 1. In other embodiments, $X^{250a}$ is a substituted or unsubstituted $C_1$-$C_6$alkyl, or a substituted or unsubstituted $C_2$-$C_6$alkenyl.

In some embodiments, compounds provided herein have a structure selected from among:

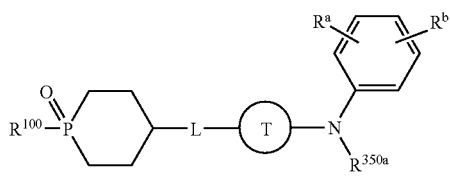

Formula (IIIa)

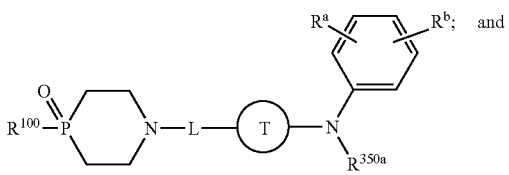

Formula (IIIb)

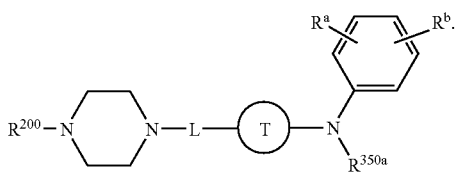

Formula (IIIc)

In certain embodiments, $R^{100}$ is halogen, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), heteroaryl, and $C_1$-$C_4$alkyl(heteroaryl); $R^{200}$ is an optionally substituted group selected from among $C_2$-$C_{10}$acyl, $C_2$-$C_6$alkenyl, $C_2$-$C_6$alkynyl, $C_3$-$C_6$cycloalkyl, $C_1$-$C_4$alkyl($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In some embodiments, $R^{350a}$ is hydrogen; $Y^{250}$ is a bond, —C(=O)—, —NHC(=O)—, —C(=O)NH—.

In other embodiments, L is selected from among:

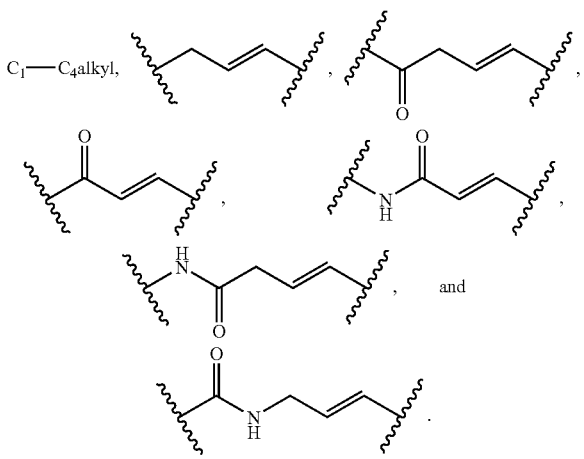

In yet other embodiments, L is selected from among: $C_1$-$C_4$alkyl,

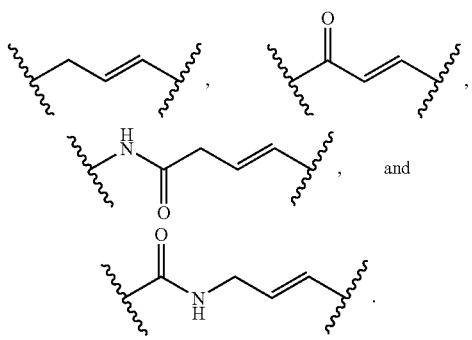

In one embodiment, compounds provided herein have a structure of Formula (IIIc). In other embodiments, compounds provided herein have a structure of Formula (IIIa). In yet other embodiments, compounds provided herein have a structure of Formula (IIIb).

In some embodiments, L is $C_1$-$C_4$ alkyl or

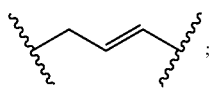

and $R^{200}$ is an optionally substituted group selected from among $C_2$-$C_{10}$acyl, aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In other embodiments, $R^{200}$ is an optionally substituted group selected from among $C_2$-$C_{10}$acyl, aryl, heteroaryl, heteroaralkyl, $C_1$-$C_6$alkylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In one aspect, L is selected from among $C_1$-$C_4$ alkyl,

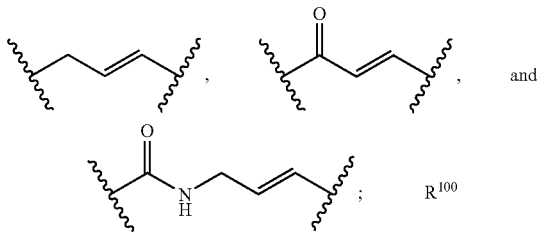

is an optionally substituted group selected from among $C_1$-$C_6$alkyl, $C_2$-$C_6$alkenyl, $C_2$-$C_6$alkynyl, phenyl, $C_1$-$C_4$alkyl (phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), heteroaryl, and $C_1$-$C_4$alkyl(heteroaryl); $R^{200}$ is an optionally substituted group selected from among $C_2$-$C_{10}$acyl, aryl, heteroaryl, heteroaralkyl, $C_1$-$C_6$alkylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In some embodiments, T is 1,7-dimethyl-9-oxo-8,9-dihydro-1H-imidazo[4,5-h]isoquinolin-2,6-ylene substituted at the 2 position with

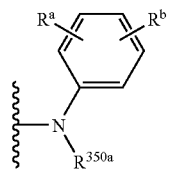

and substituted at the 6 position with

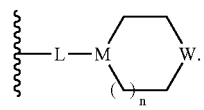

In yet other embodiments, $Y^{250}$ is a bond, —O—, —S(=O)—, —S(=O)$_2$—, —C(=O)—, —NH—, —NHC(=O)—, —NHC(=O)NH—, —C(=O)NH—, —OC(=O)—, —C(=O)O—, —NHSO$_2$—, —SO$_2$NH—, —NHC(=O)O—, or —OC(=O)NH—; E is O; and $R^{350a}$ is hydrogen, or a substituted or unsubstituted $C_1$-$C_6$alkyl.

In certain embodiments, $X^{250a}$ is a substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl; and n is 1.

In some embodiments, $R^{100}$ is halogen, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), heteroaryl, and $C_1$-$C_4$alkyl(heteroaryl); $R^{200}$ is an optionally substituted group selected from among $C_2$-$C_{10}$acyl, $C_2$-$C_6$alkenyl, $C_2$-$C_6$alkynyl, $C_3$-$C_6$cycloalkyl, $C_1$-$C_4$alkyl ($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In other embodiments, $R^{350a}$ is hydrogen; $Y^{250}$ is —C(=O)—; and $X^{250a}$ is a substituted or unsubstituted $C_1$-$C_6$alkyl.

In certain embodiments, L is

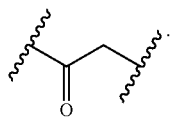

In some embodiments, compounds provided herein have a structure of Formula (IIIb). In other embodiments compounds provided herein have a structure of Formula (IIIa). In yet other embodiments, compounds provided herein have a structure of Formula (IIIc).

In another embodiment, provided herein are compounds of Formula (IV):

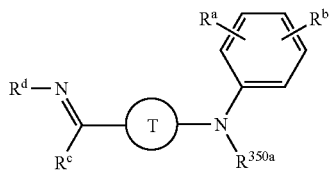

Formula (IV)

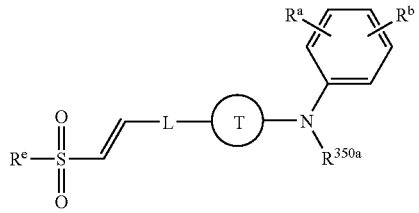

Formula (V)

wherein:
  $R^a$ and $R^b$ are each independently selected from among H, halogen, CN, $NO_2$, $C_1$-$C_4$alkyl, $C_1$-$C_4$haloalkyl, and $C_1$-$C_4$alkoxy;
  T is 1,6-dimethyl-9-oxo-8,9-dihydro-1H-imidazo[4,5-h]isoquinolin-2,7-ylene;
  $R^d$ is —OH, or —NH—C(O)—$R^e$;
  $R^c$ is H or $C_1$-$C_4$alkyl, halogen, or $C_1$-$C_4$haloalkyl;
  $R^e$ is a substituted or unsubstituted group selected from among $C_1$-$C_6$ alkyl, aryl, or heteroaryl; and
pharmaceutically active metabolites, pharmaceutically acceptable solvates, pharmaceutically acceptable salts, or
pharmaceutically acceptable prodrugs thereof In some embodiments, T is 1,6-dimethyl-9-oxo-8,9-dihydro-1H-imidazo[4,5-h]isoquinolin-2,7-ylene, substituted at the 2 position with

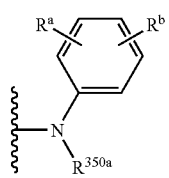

and substituted at the 7 position with

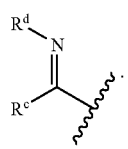

In certain embodiments, $R^c$ is H; and $R^e$ is a substituted or unsubstituted group selected from among aryl, and heteroaryl. In yet other embodiments, $R^e$ is a substituted or unsubstituted group selected from among phenyl, and heteroaryl containing 1 or 2 N atoms.

In another embodiment, provided herein are compounds of Formula (V):

wherein:
  $R^a$ and $R^b$ are each independently selected from among H, halogen, CN, $NO_2$, $C_1$-$C_4$alkyl, $C_1$-$C_4$haloalkyl, and $C_1$-$C_4$alkoxy;
  T is 1,6-dimethyl-9-oxo-8,9-dihydro-1H-imidazo[4,5-h]isoquinolin-2,7-ylene, or 1,7-dimethyl-9-oxo-8,9-dihydro-1H-imidazo[4,5-h]isoquinolin-2,6-ylene;
  L is —$X^{250a}$—$Y^{250}$—$X^{250b}$— or —$X^{250b}$—$Y^{250}$—$X^{250a}$—, wherein,
    $X^{250a}$ is a bond, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;
    $Y^{250}$ is a bond, —O—, —S(=O)—, —S(=O)$_2$—, —C(=O)—, —$NR^{45}$—, —NH—, —NHC(=O)—, —$NR^{45}$C(=O)—, —$NR^{45}$C(=O)$NR^{45}$—, —C(=O)NH—, —C(=O)$NR^{45}$—, —OC(=O)—, —C(=O)O—, —NHSO$_2$—, —$NR^{45}$SO$_2$—, —SO$_2$NH—, —$_{SO2}NR^{45}$—, —C($R^{45}$)=NO—, 13 CH=NO—, —ON=CH—, heteroaryl, aryl, —NHC(=O)O—, —OC(=O)NH—, —$NR^{45}$C(=O)O—, or —OC(=O)$NR^{45}$—;
    $X^{250b}$ is a bond, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;
    where each $R^{45}$ is independently selected from among hydrogen, substituted or unsubstituted $C_1$-$C_6$alkyl, substituted or unsubstituted $C_3$-$C_8$cycloalkyl, substituted or unsubstituted $C_2$-$C_6$alkenyl, substituted or unsubstituted $C_2$-$C_6$alkynyl;
  $R^e$ is a substituted or unsubstituted group selected from among $C_1$-$C_6$ alkyl, aryl, or heteroaryl;
  $R^{350a}$ is hydrogen, a substituted or unsubstituted $C_1$-$C_6$alkyl, a substituted or unsubstituted $C_2$-$C_6$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl; and pharmaceutically active metabolites, pharmaceutically acceptable solvates, pharmaceutically acceptable salts, or pharmaceutically acceptable prodrugs thereof.

In certain embodiments, T is 1,6-dimethyl-9-oxo-8,9-dihydro-1H-imidazo[4,5-h]isoquinolin-2,7-ylene substituted at the 2 position with

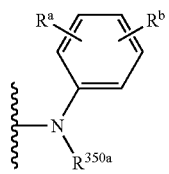

and substituted at the 7 position with

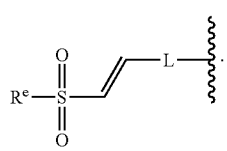

In other embodiments, $Y^{250}$ is a bond; and $R^{350a}$ is hydrogen, a substituted or unsubstituted $C_1$-$C_6$alkyl, a substituted or unsubstituted $C_1$-$C_6$haloalkyl.

In one aspect, $X^{250a}$ is a bond; and $X^{250b}$ is a bond.

In another aspect, T is 1,7-dimethyl-9-oxo-8,9-dihydro-1H-imidazo[4,5-h]isoquinolin-2,7-ylene substituted at the 2 position with

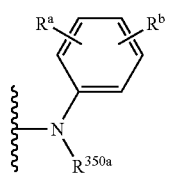

and substituted at the 6 position with

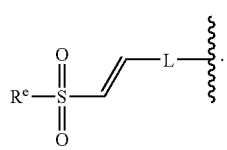

In some embodiments, $X^{250a}$ is a bond, substituted or unsubstituted $C_1$-$C_6$alkyl; $Y^{250}$ is a bond, —O—, —C(=O)—, —NH—, —NHC(=O)—, —NR$^{45}$C(=O)—, —NHC(=O)NH—, —C(=O)NH—, —OC(=O)—, —C(=O)O—, —NHC(=O)O—, or —OC(=O)NH—; and $X^{250b}$ is a bond, substituted or unsubstituted $C_1$-$C_6$alkyl, or substituted or unsubstituted $C_1$-$C_6$haloalkyl.

In some embodiments, $R^{350a}$ is hydrogen, a substituted or unsubstituted $C_1$-$C_6$alkyl, a substituted or unsubstituted $C_1$-$C_6$haloalkyl. In some embodiments, $R^{350a}$ is hydrogen.

In other embodiments, $Y^{250}$ is a bond, —NHC(=O)—, —C(=O)NH—, —OC(=O)—, or —C(=O)O—.

In another aspect, provided herein are compounds of Formula (VI):

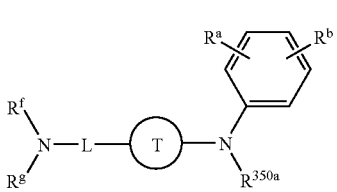

Formula (VI)

wherein:

$R^a$ and $R^b$ are each independently selected from among H, halogen, CN, NO$_2$, $C_1$-$C_4$alkyl, $C_1$-$C_4$haloalkyl, and $C_1$-$C_4$alkoxy;

T is 1,6-dimethyl-9-oxo-8,9-dihydro-1H-imidazo[4,5-h]isoquinolin-2,7-ylene, or 1,7-dimethyl-9-oxo-8,9-dihydro-1H-imidazo[4,5-h]isoquinolin-2,6-ylene;

L is a substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$heteroalkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;

$R^f$ is a substituted or unsubstituted $C_2$-$C_6$alkynyl;

$R^g$ is H, or an optionally substituted group selected from among $C_2$-$C_{10}$acyl, $C_1$-$C_6$alkyl, $C_2$-$C_6$alkenyl, $C_2$-$C_6$alkynyl, $C_3$-$C_6$cycloalkyl, $C_1$-$C_4$alkyl($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl;

$R^{350a}$ is hydrogen, a substituted or unsubstituted $C_1$-$C_6$alkyl, a substituted or unsubstituted $C_2$-$C_6$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl; and pharmaceutically active metabolites, pharmaceutically acceptable solvates, pharmaceutically acceptable salts, or pharmaceutically acceptable prodrugs thereof In some embodiments, T is 1,6-dimethyl-9-oxo-8,9-dihydro-1H-imidazo[4,5-h]isoquinolin-2,7-ylene substituted at the 2 position with

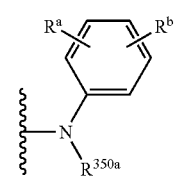

and substituted at the 7 position with

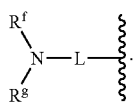

In some embodiments, L is a substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_2$-$C_6$alkenyl, or substituted or unsubstituted $C_2$-$C_6$heteroalkenyl; and $R^{350a}$ is hydrogen, a substituted or unsubstituted $C_1$-$C_6$alkyl. In other embodiments, L is a substituted or unsubstituted $C_1$-$C_6$alkyl, substituted or unsubstituted $C_1$-$C_6$heteroalkyl, substituted or unsubstituted $C_2$-$C_6$alkenyl, or substituted or unsubstituted $C_2$-$C_6$heteroalkenyl.

In other embodiments, $R^g$ is H, or an optionally substituted group selected from among $C_2$-$C_{10}$acyl, $C_1$-$C_6$alkyl, $C_2$-$C_6$alkenyl, $C_2$-$C_6$alkynyl, $C_1$-$C_6$alkylsulfonyl, $C_2$-$C_6$alkenylsulfonyl, arylsulfonyl, heteroarylsulfonyl, or $C_1$-$C_{10}$alkoxycarbonyl.

In some embodiments, L is a substituted or unsubstituted $C_1$-$C_6$alkyl, or substituted or unsubstituted $C_2$-$C_6$alkenyl; and $R^g$ is H, or an optionally substituted $C_1$-$C_6$alkyl.

In some embodiments, L is selected from among a substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl,

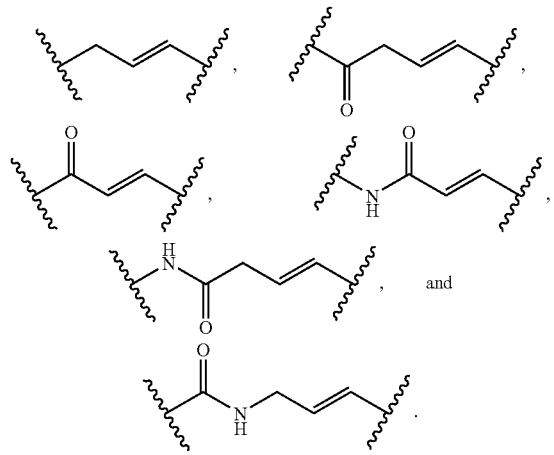

In other embodiments, L is selected from among a substituted or unsubstituted $C_1$-$C_6$alkyl, or substituted or unsubstituted $C_2$-$C_6$alkenyl,

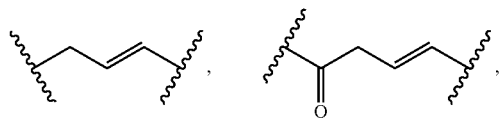

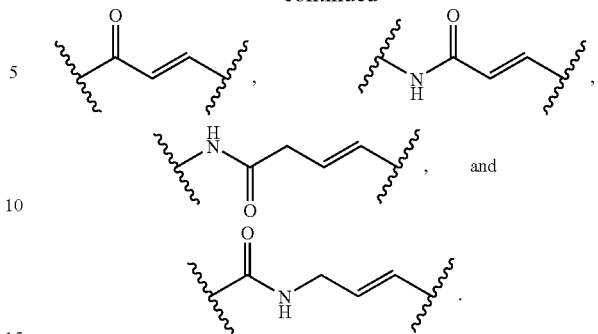

In yet other embodiments, L is selected from among a substituted or unsubstituted $C_1$-$C_6$alkyl, substituted or unsubstituted $C_2$-$C_6$alkenyl,

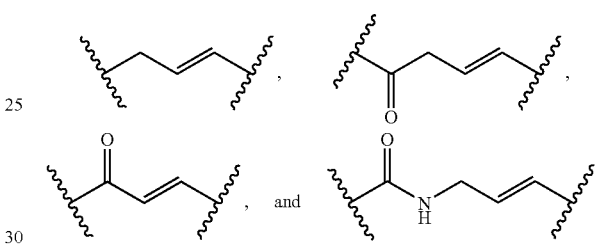

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In one aspect, provided herein is a compound selected from among:

2-(4-fluoro-2-methylphenylamino)-1,6-dimethyl-7-[3-(4-methyl-4-oxo-4$\lambda^5$[1,4]azaphosphinan-1-yl)-propenyl]-1,8-dihydro-imidazo[4,5-h]isoquinolin-9-one (Compound 1); 2-(2,6-dichloro-phenylamino)-1,6-dimethyl-7-[3-(4-methyl-4-oxo-4$\lambda^5$[1,4]azaphosphinan-1-yl)-propenyl]-1,8-dihydro-imidazo[4,5-h]isoquinolin-9-one (Compound 2); 2-(4-fluoro-2-methylphenylamino)-1,6-dimethyl-7-[3-(4-oxo-4-phenyl-4$\lambda^5$-[1,4]azaphosphinan-1-yl)-propenyl]-1,8-dihydro-imidazo[4,5-h]isoquinolin-9-one (Compound 3); 2-(3-fluoro-6-methylphenylamino)-1,6-dimethyl-7-[3-(4-oxo-4-phenyl-4$\lambda^5$-[1,4]azaphosphinan-1-yl)-propenyl]-1,8-dihydro-imidazo[4,5-h]isoquinolin-9-one (Compound 4); 2-(2,6-dichlorophenylamino)-1,6-dimethyl-7-[3-(4-oxo-4-phenyl-4$\lambda^5$-[1,4]azaphosphinan-1-yl)-propenyl]-1,8-dihydro-imidazo[4,5-h]isoquinolin-9-one (Compound 5); 2-(2,4-dichloro-6-methylphenylamino)-1,6-dimethyl-7-[3-(4-oxo-4-phenyl-4$\lambda^5$-[1,4]azaphosphinan-1-yl)-propenyl]-1,8-dihydro-imidazo[4,5-h]isoquinolin-9-one (Compound 6); 2-(3-fluoro-6-methylphenylamino)-1,6-dimethyl-7-{2-[(4-oxo-4-phenyl-4$\lambda^5$-[1,4]azaphosphinan-1-yl)-carbonyl]ethenyl}-1,8-dihydro-imidazo[4,5-h]isoquinolin-9-one (Compound 7); 2-(2,4-dichloromethylphenylamino)-1,6-dimethyl-7-[3-(4-oxo-4-phenyl-4$\lambda^5$-[1,4]azaphosphinan-1-yl)-propyl]-1,8-dihydro-imidazo[4,5-h]isoquinolin-9-one (Compound 8); 2-(4-fluoro-2-methylphenylamino)-1,6-dimethyl-7-[3-(4-oxo-4-phenyl-4$\lambda^5$-[1,4]azaphosphinan-1-yl)- propyl]-1,8-dihydro-imidazo[4,5-h]isoquinolin-9-one (Compound 9); 2-(4-fluoro-2-methylphenylamino)-1,6-dimethyl-7-[3-(4-oxo-4-(4-fluorophenyl)-4λ$^5$-[1,4]azaphosphinan-1-yl)-propenyl]-1,8-dihydro-imidazo[4,5-h]isoquinolin-9-one (Compound 10); 2-(3-fluoro-6-methylphenylamino)-1,6-dimethyl-7-[3-(4-oxo-4-(4-methoxyphenyl)-4λ$^5$-[1,4]azaphosphinan-1-yl)-propenyl]-1,8-dihydro-imidazo[4,5-h]isoquinolin-9-one (Compound 11); 2-(4-fluoro-2-methylphenylamino)-1,6-dimethyl-7-{3-[4-(4-fluorophenylmethyl)-4-oxo-4λ$^5$-[1,4]azaphosphinan-1-yl]-propenyl}-1,8-dihydro-imidazo[4,5-h]isoquinolin-9-one (Compound 12); 2-(4-fluoro-2-methylphenylamino)-1,6-dimethyl-7-{3-[4-(cyclopropylmethyl)-4-oxo-4λ$^5$-[1,4]azaphosphinan-1-yl]-propenyl}-1,8-dihydro-imidazo[4,5-h]isoquinolin-9-one (Compound 13); 2-(4-fluoro-2-methylphenylamino)-1,6-dimethyl-7-{3-[4-(cyclopropyl)-4-oxo-4λ$^5$-[1,4]azaphosphinan-1-yl]-propenyl}-1,8-dihydro-imidazo[4,5-h]isoquinolin-9-one (Compound 14); 2-(4-fluoro-2-methylphenylamino)-1,6-dimethyl-7-{3-[(1-oxo-1-methyl-1λ$^5$-phosphinan-4-yl)-carbonylamino]propenyl}-1,8-dihydro-imidazo[4,5-h]isoquinolin-9-one (Compound 15); 2-(4-fluoro-2-methylphenylamino)-1,6-dimethyl-7-{3-[(1-oxo-1-trans-phenyl-1λ$^5$-phosphinan-4-yl)-carbonylamino]propenyl}-1,8-dihydro-imidazo[4,5-h]isoquinolin-9-one (Compound 16); 2-(4-fluoro-2-methylphenylamino)-1,6-dimethyl-7-{3-[(1-oxo-1-cis-phenyl-1λ$^5$-phosphinan-4-yl)-carbonylamino]propenyl}-1,8-dihydro-imidazo[4,5-h]isoquinolin-9-one (Compound 17); 2-(2,6-dichlorophenylamino)-1,6-dimethyl-7-[3-(N-phenylpiperazin-1-yl)-propenyl]-1,8-dihydro-imidazo[4,5-h]isoquinolin-9-one (Compound 18); 2-(4-fluoro-2-methylphenylamino)-1,6-dimethyl-7-[3-(N-phenylpiperazin-1-yl)-propenyl]-1,8-dihydro-imidazo[4,5-h]isoquinolin-9-one (Compound 19); 2-(4-fluoro-2-methylphenylamino)-1,6-dimethyl-7-[3-(N-(4-chlorophenyl)-piperazin-1-yl)-propenyl]-1,8-dihydro-imidazo[4,5-h]isoquinolin-9-one (Compound 20); 2-(4-fluoro-2-methylphenylamino)-1,6-dimethyl-7-[3-(N-methylcarbonylpiperazin-1-yl)-propenyl]-1,8-dihydro-imidazo[4,5-h]isoquinolin-9-one (Compound 21); 2-(4-fluoro-2-methylphenylamino)-1,6-dimethyl-7-[3-(N-phenylcarbonylpiperazin-1-yl)-propenyl]-1,8-dihydro-imidazo[4,5-h]isoquinolin-9-one (Compound 22); 2-(4-fluoro-2-methylphenylamino)-1,6-dimethyl-7-[3-(N-(pyridin-4-yl)-piperazin-1-yl)-propenyl]-1,8-dihydro-imidazo[4,5-h]isoquinolin-9-one (Compound 23); 2-(4-fluoro-2-methylphenylamino)-1,6-dimethyl-7-[3-(N-methylsulfonylpiperazin-1-yl)-propenyl]-1,8-dihydro-imidazo[4,5-h]isoquinolin-9-one (Compound 24); 2-(3-fluoro-2-methylphenylamino)-1,6-dimethyl-7-[3-(N-methylsulfonylpiperazin-1-yl)-propenyl]-1,8-dihydro-imidazo[4,5-h]isoquinolin-9-one (Compound 25); 2-(4-fluoro-2-methylphenylamino)-1,6-dimethyl-7-[3-(N-(pyridin-2-yl)-piperazin-1-yl)-propenyl]-1,8-dihydro-imidazo[4,5-h]isoquinolin-9-one (Compound 26); 2-(4-fluoro-2-methylphenylamino)-1,6-dimethyl-7-[3-(N-(pyrimidin-2-yl)-piperazin-1-yl)-propenyl]-1,8-dihydro-imidazo[4,5-h]isoquinolin-9-one (Compound 27); 2-(4-fluoro-2-methylphenylamino)-1,6-dimethyl-7-[3-(N-(2,6-dichlorophenylmethyl)-piperazin-1-yl)-propenyl]-1,8-dihydro-imidazo[4,5-h]isoquinolin-9-one (Compound 28); 2-(4-fluoro-2-methylphenylamino)-1,6-dimethyl-7-[3-(N-phenylsulfonylpiperazin-1-yl)-propenyl]-1,8-dihydro-imidazo[4,5-h]isoquinolin-9-one (Compound 29); 2-(4-fluoro-2-methylphenylamino)-1,6-dimethyl-7-[3-(N-(4-fluorophenyl)-piperazin-1-yl)-propenyl]-1,8-dihydro-imidazo[4,5-h]isoquinolin-9-one (Compound 30); 2-(4-fluoro-2-methylphenylamino)-1,6-dimethyl-7-[3-(N-tert-butyloxycarbonylpiperazin-1-yl)-propenyl]-1,8-dihydro-imidazo[4,5-h]isoquinolin-9-one (Compound 31); 2-(4-fluoro-2-methylphenylamino)-1,6-dimethyl-7-[3-(N-(N,N-dimethylaminosulfonyl)-piperazin-1-yl)-propenyl]-1,8-dihydro-imidazo[4,5-h]isoquinolin-9-one (Compound 32); 2-(4-fluoro-2-methylphenylamino)-1,6-dimethyl-7-[3-(N-ethylcarbonylpiperazin-1-yl)-propenyl]-1,8-dihydro-imidazo[4,5-h]isoquinolin-9-one (Compound 33); 2-(4-fluoro-2-methylphenylamino)-1,6-dimethyl-7-[3-(N-(isopropylsulfonyl)-piperazin-1-yl)-propenyl]-1,8-dihydro-imidazo[4,5-h]isoquinolin-9-one (Compound 34); 2-(4-fluoro-2-methylphenylamino)-1,6-dimethyl-7-[3-(N-(ethylsulfonyl)-piperazin-1-yl)-propenyl]-1,8-dihydro-imidazo[4,5-h]isoquinolin-9-one (Compound 35); 2-(4-fluoro-2-methylphenylamino)-1,6-dimethyl-7-[3-(N-isopropylcarbonylpiperazin-1-yl)-propenyl]-1,8-dihydro-imidazo[4,5-h]isoquinolin-9-one (Compound 36); 2-(2,6-dichlorophenylamino)-1,6-dimethyl-7-[2-(phenylsulfonyl)-ethenyl]-1,8-dihydro-imidazo[4,5-h]isoquinolin-9-one (Compound 37); 2-(2,6-dichlorophenylamino)-1,6-dimethyl-7-[1-(phenylcarbonyloxy)-prop-2-enyl]-1,8-dihydro-imidazo[4,5-h]isoquinolin-9-one (Compound 38); 2-(2,6-dichlorophenylamino)-1,6-dimethyl-7-[1-(phenylcarbonyloxy)-2,2-difluorobutynyl]-1,8-dihydro-imidazo[4,5-h]isoquinolin-9-one (Compound 39); 2-(2,6-dichlorophenylamino)-1,6-dimethyl-7-[2,2-difluoro-1-hydroxy-2-(N-phenylmethyl-[1,2,3]triazol-4-yl)-ethyl]-1,8-dihydro-imidazo[4,5-h]isoquinolin-9-one (Compound 40); 2-(2,6-dichlorophenylamino)-1,6-dimethyl-7-(1-hydroxy-3-phenylprop-2-yn-1-yl)-1,8-dihydro-imidazo[4,5-h]isoquinolin-9-one (Compound 41); 2-(2,6-dichlorophenylamino)-1,6-dimethyl-7-[3-(N-methyl-N-(prop-2-ynyl)amino)prop-1-enyl]-1,8-dihydro-imidazo[4,5-h]isoquinolin-9-one (Compound 42); 2-(4-fluoro-2-methylphenylamino)-1,6-dimethyl-7-[3-(N-methyl-N-(prop-2-ynyl)amino)prop-1-enyl]-1,8-dihydro-imidazo[4,5-h]isoquinolin-9-one (Compound 43); 2-(2,6-dichlorophenylamino)-1,6-dimethyl-9-oxo-8,9-dihydro-1H-imidazo[4,5-h]isoquinoline-7-carbaldehyde oxime (Compound 44); benzoic acid [2-(2,6-dichlorophenylamino)-1,6-dimethyl-9-oxo-8,9-dihydro-1H-imidazo[4,5-h]isoquinolin-7-ylmethylene]-hydrazide (Compound 45); 4-(N,N-dimethylamino)-benzoic acid [2-(2,6-dichlorophenylamino)-1,6-dimethyl-9-oxo-8,9-dihydro-1H-imidazo[4,5-h]isoquinolin-7-ylmethylene]-hydrazide (Compound 46); pyridine-2-carboxylic acid [2-(2,6-dichlorophenylamino)-1,6-dimethyl-9-oxo-8,9-dihydro-1H-imidazo[4,5-h]isoquinolin-7-ylmethylene]-hydrazide (Compound 47); pyridine-3-carboxylic acid [2-(2,6-dichlorophenylamino)-1,6-dimethyl-9-oxo-8,9-dihydro-1H-imidazo[4,5-h]isoquinolin-7-ylmethylene]-hydrazide (Compound 48); 2-methoxybenzoic acid [2-(2,6-dichlorophenylamino)-1,6-dimethyl-9-oxo-8,9-dihydro-1H-imidazo[4,5-h]isoquinolin-7-ylmethylene]-hydrazide (Compound 49); 2-(4-fluoro-2-methylphenylamino)-1,7-dimethyl-6-{2-[4-(4-flourophenyl)-4-oxo-4λ$^5$[1,4]azaphosphinan-1-yl]-2-oxoethyl}-1,8-dihydro-imidazo[4,5-h]isoquinolin-9-one (Compound 50); and (S)-2-(4-fluoro-2-methylphenylamino)-1,7-dimethyl-6-{N-[1-(phenylsulfonyl)hex-1-en-3-yl]-amino-2-oxoethyl}-1,8-dihydro-imidazo[4,5-h]isoquinolin-9-one (Compound 51).

In a further aspect are provided pharmaceutical compositions, which include a therapeutically effective amount of at least one of any of the compounds herein, or a pharmaceutically acceptable salt, pharmaceutically active metabolite, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

In certain embodiments, provided herein is a pharmaceutical composition containing: i) a physiologically acceptable carrier, diluent, and/or excipient; and ii) one or more compounds provided herein.

In another aspect, provided herein is a method for inhibiting Bruton's tyrosine kinase or a homolog thereof in a subject in need thereof by administering to the subject a composition containing a therapeutically effective amount of any of the above-mentioned compounds.

Articles of manufacture containing packaging material, a compound or composition or pharmaceutically acceptable derivative thereof provided herein, which is effective for inhibiting the activity of certain tyrosine kinase(s), such as Btk, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of tyrosine kinase(s), such as Btk, are provided.

In a further aspect, provided herein is a method for inhibiting Bruton's tyrosine kinase in a subject in need thereof by administering to the subject thereof a composition containing a therapeutically effective amount of at least one reversible inhibitor of Btk, including any of the above-mentioned compounds, which are described herein. In some embodiments, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In other embodiments, the subject in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In certain embodiments, the subject in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD 184352, PD0325901, ARRY-142886, SB239063, SP600125, BAY 43-9006, wortmannin, or LY294002; Syk inhibitors; PKC-beta inhibitors; PI3K inhibitors; mTOR inhibitors; or an antibody effective for treating cancer (e.g., rituxan).

In further embodiments, the subject in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoirunune disease by administering to a subject in need thereof a composition containing a therapeutically effective amount of at least one reversible inhibitor of Btk, including any of the above-mentioned compounds. In one embodiment, the autoimmune disease is arthritis. In another embodiment, the autoimmune disease is lupus. In some embodiments, the autoimmune disease is rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In a further aspect, provided herein is a method for treating a heteroimmune condition or disease by administering to a subject in need thereof a composition containing a therapeutically effective amount of at least one reversible inhibitor of Btk, including any of the above-mentioned compounds. In some embodiments, the heteroimmune conditioin or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one reversible inhibitor of Btk, including any of the above-mentioned compounds. In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one reversible inhibitor of Btk, including any of the above-mentioned compounds. In one embodiment, the cancer is a B-cell proliferative disorder, e.g., difiuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one reversible inhibitor of Btk, including any of the above-mentioned compounds. In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

Any of the combinations of the groups described above for the various variables is contemplated herein.

The terms "inhibits, inhibiting, or inhibitor" of a kinase, as used herein, refer to inhibition of enzymatic phosphotransferase activity.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. All references cited herein, including patents, patent applications, and publications, are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The appended claims particularly point out features set forth herein. A better understanding of the features and advantages of the present disclosure will be obtained by reference to the following detailed description that sets forth illustrative embodiments, in which the principles described herein are utilized.

Disclosed herein are compounds that inhibit the activity the activity of a subset of tyrosine kinase(s), compositions that include the compounds, and methods of their use. Compounds disclosed herein are inhibitors of certain tyrosine kinase(s) (e.g., Btk), and are useful in the treatment of diseases, disorders, or conditions that would benefit from the inhibition of these tyrosine kinase(s). In some embodiments, compounds provided herein are used to inhibit the activity of Bruton's tyrosine kinase (Btk).

The term "Bruton's tyrosine kinase," as used herein, refers to Bruton's tyrosine kinase from Homo sapiens, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Acession No. AAB47246), dog (GenBank Acession No. XP_549139.), rat (GenBank Acession No. NP_001007799), chicken (GenBank Acession No. NP_989564), or zebra fish (GenBank Acession No. XP_698117), and fusion proteins of any of the foregoing that exhibit kinase activity towards one or more substrates of Bruton's tyrosine kinase (e.g. a peptide substrate having the amino acid sequence "AVLESEEELYSSARQ").

Btk is involved in abnormal levels of cell proliferation, apoptosis, cell migration and invasion, and angiogenesis associated with tumor growth. Btk is a key regulator of B-cell development, activation, signaling, and survival. In addition, Btk plays a role in collagen-stimulated platelet aggregation. Btk's function as both a regulator of apoptosis and its involvement in a number of developmental processes makes Btk a desirable target for anti-cancer agents, anti-inflammatory agents, and anti-viral agents, anti-thromboembolic agents, as well as for treating autoimmune disease and acute inflammatory reactions.

Btk may have a role in infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agamnaglobulinemia—an immune deficiency disease characterized by defects in B cell maturation and function, psoriasis, allergy, Crohn's disease, irrtiable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's diesease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenström macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves disease.

Btk-associated lymphomas and include B-cell lymphoma, Hodgkin's and non-Hodgkin's lymphoma, hairy cell leukemia, chronic and acute mylelogenous leukemia, multiple myeloma, EBV lymphomia, acute lymphoblastic leukemia, and chronic lymphocytic leukemia.

Accordingly, while not being bound by theory, it is believed that inhibiting the activity of Btk is useful for treating any of the following conditions.

In some embodiments, the methods described herein can be used to treat an autoimmnune disease, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

In some embodiments, the methods described herein can be used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or coclroach calyx), type I hypersensitivity, allergic conjunctivitis, allergic rhinitis, and atopic dermatitis.

In further embodiments, the methods described herein can be used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Symptoms, diagnostic tests, and prognostic tests for each of the above-mentioned conditions are known in the art. See, e.g., *Harrison's Principles of Internal Medicine©,*" 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of the compounds described herein for treating any of the foregoing diseases.

For example, dosing of the compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837., L. Svensson, R. Holmdahl, *Am. J. Pathol.* 2003, 163, 1827).

In another example, dosing of the compounds for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866.

Animal models for treatment of thromboembolic disorders are also known.

While not wishing to be bound to theory, phosphatases can also play a role in a "disease, disorder, or syndrome responsive to the inhibition of tyrosine kinases" as cognates of tyrosine kinases; that is, tyrosine kinases phosphorylate and phosphatases dephosphorylate, for example, protein substrates. Therefore, compounds of the invention, while modulating tyrosine kinase activity as described herein, may also modulate, either directly or indirectly, phosphatase activity. This additional modulation, if present, may be synergistic (or not) to activity of compounds of the invention toward a related or otherwise interdependent kinase or kinase family. As previously stated, the compounds of the invention are useful for treating diseases characterized in part by abnormal levels of cell proliferation (i.e. tumor growth), programmed cell death (apoptosis), cell migration and invasion, and angiogenesis associated with tumor growth.

The therapeutic efficacy of the compound for treating any of the foregoing diseases can be optimized during a course of treatment. For example, a subject being treated can undergo a diagnostic evaluation to correlate the relief of disease symptoms or pathologies to inhibition of the relevant tyrosine kinase in vivo by administering a given dose of any of the compounds described herein. Cellular assays for determining in vivo tyrosine kinase are available. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the compound that is administered to a subject can be increased or decreased as needed so as to maintain a level of inhibition of the target tyrosine kinase (e.g., Btk) optimal for treating the subject's disease state.

Generally, the compounds used in the methods described herein are identified or characterized in an in vitro assay, e.g., an acellular biochemical assay or a cellular functional assay. Such assays are useful to determine an in vitro $IC_{50}$ for a compound.

For example, an acellular kinase assay can be used to determine, e.g., Btk activity after incubation of the kinase in the absence or presence of a range of concentrations of a candidate tyrosine kinase inhibitor compound. Many acellular kinase assays are available. See, e.g., see Kuzmic et al. (2000) *Anal. Biochem,* 286, 45-50.

Cellular functional assays for tyrosine kinase inhibition include measuring one or more cellular endpoints in response to stimulating a signaling pathway that is mediated by the tyrosine kinase (e.g., BCR activation in Ramos cells) in the absence or presence of a range of concentrations of a candidate tyrosine inhibitor compounds. For example, in the case of Btk, useful endpoints include, e.g., autophosphorylation of Btk, phosphorylation of a Btk target protein (e.g., PLC-γ), and cytoplasmic calcium flux, in response to BCR activation.

High throughput assays for many acellular biochemical assays (e.g., kinase assays) and cellular functional assays (e.g., calcium flux) are available. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of tyrosine kinase inhibitor compounds without undue effort.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there are a plurality of definitions for terms herein, those in this section prevail. Where reference is made to a URI or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, may be branched, straight chain, or cyclic. Depending on the structure, an alkyl group can be a monoradical or a diradical (i.e., an alkylene group).

As used herein, $C_1$-$C_x$ includes $C_1$-$C_2$, $C_1$-$C_3$ ... $C_1$-$C_x$.

The "alkyl" moiety may have 1 to 10 carbon atoms (whenever it appears herein, a numerical range such as "1 to 10" refers to each integer in the given range; e.g., "1 to 10 carbon atoms" means that the alkyl group may have 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups can be substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

As used herein, the term "non-cyclic alkyl" refers to an alkyl that is not cyclic (i.e., a straight or branched chain containing at least one carbon atom). Non-cyclic alkyls can be fully saturated or can contain non-cyclic alkenes and/or alkynes. Non-cyclic alkyls can be optionally substituted.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which may be the same or different. The alkenyl moiety may be branched, straight chain, or cyclic (in which case, it would also be known as a "cycloalkenyl" group). Depending on the structure, an alkenyl group can be a monoradical or a diradical (i.e., an alkenylene group). Alkenyl groups can be optionally substituted. Non-limiting examples of an alkenyl group include —CH=CH$_2$, —C(CH$_3$)=CH$_2$, —CH=CHCH$_3$, —C(CH$_3$)=CHCH$_3$, —CH=CH—, —C(CH$_3$)=CH—, —CH=CHCH$_2$—, —CH=CHCH$_2$CH$_2$— and —C(CH$_3$)=CHCH$_2$—. Alkenyl groups, unless otherwise stated, may have 2 to 10 carbons.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. The "R" portion of the alkynyl moiety may be branched, straight chain, or cyclic. Depending on the structure, an alkynyl group can be a monoradical or a diradical (i.e., an alkynylene group). Alkyl groups can be optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups, unless otherwise stated, may have 2 to 10 carbons.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Alkoxyalkyl" refers to an alkyl radical, as defined herein, substituted with at least one alkoxy group, as defined herein.

An "alkenyloxy" group refers to a (alkenyl)O— group, where alkenyl is as defined herein.

An "amide" is a chemical moiety with the formula —C(O) NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "aromatic" refers to a planar ring having a delocalized π-electron system containing 4n+2π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

"Aralkyl" or "arylalkyl" means an alkyl radical, as defined herein, substituted with an aryl group. Non-limiting aralkyl groups include, benzyl, phenethyl, and the like.

"Aralkenyl" means an alkenyl radical, as defined herein, substituted with at least one aryl group, as defined herein.

The term "bond" or "single bond" refers to a chemical bond between two atoms, or two moieties when the atoms joined by the bond are considered to be part of larger substructure.

The term "carbocyclic" or "carbocycle" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. Carbocycles include cycloalkyls and aryls.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

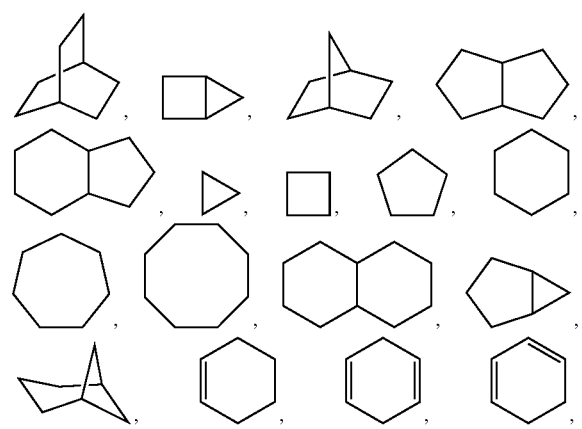

-continued

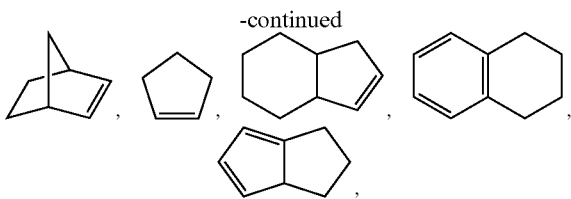

and the like. Depending on the structure, an cycloalkyl group can be a monoradical or a diradical (e.g., an cycloalkylene group).

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylethyl, cyclohexylmethyl, and the like.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "halo" or, alternatively, "halogen" or "halide" means fluoro, chloro, bromo or iodo.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

As used herein, the terms "heteroalkyl" "heteroalkenyl" and "heteroalkynyl" include optionally substituted alkyl, alkenyl and alkynyl radicals in which one or more skeletal chain atoms are selected from an atom other than carbon, e.g., oxygen, nitrogen, sulfur, silicon, phosphorus or combinations thereof.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "fused" refers to structures in which two or more rings share one or more bonds.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

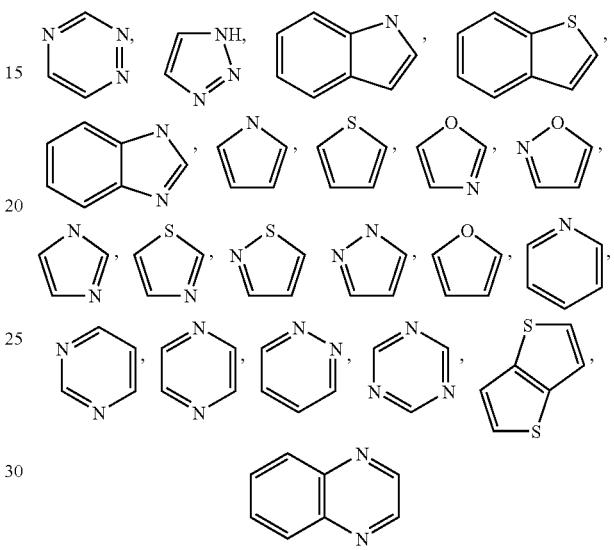

and the like. Depending on the structure, a heteroaryl group can be a monoradical or a diradical (i.e., a heteroarylene group).

"Heteroarylalkyl" or "heteroaralkyl" refers to an alkyl group, as defined herein, substituted with a heteroaryl, as defined herein.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imnidazoline, irnidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

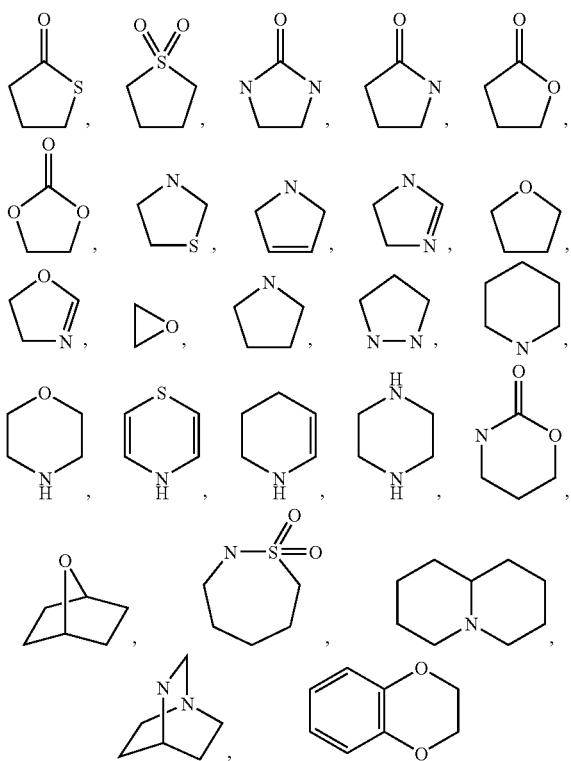

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heterocycloalkylalkyl" refers to an alkyl group, as defined herein, substituted with a heterocycloalkyl, as defined herein.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuiranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, iniudazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofuirazanyl, benzothiophenyl, benzothiazolyl, benzoxazolyl, quinazolinyl, quinoxalinyl, naphthyridinyl, and fuiropyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group). Phosphorous-containing rings include, but are not limited to, 1-oxo-phospholanyl, 1-methyl-1-oxo-phosphinan-4-yl, 1-phenyl-1-oxo-phosphinan-4-yl, 1-(cyclopropylmethyl)-1-oxo-phosphinan-4-yl, 4-methyl-4-oxo-[1,4]azaphosphinan-1-yl, 4-phenyl-4-oxo-[1,4]azaphosphinan-1-yl, and 4-(cyclopropylmethyl)-4-oxo-[1,4]azaphosphinan-1-yl.

As used herein, "1,6-dimethyl-9-oxo-8,9-dihydro-1H-imidazo[4,5-h]isoquinolin-2,7-ylene" refers to the following structure:

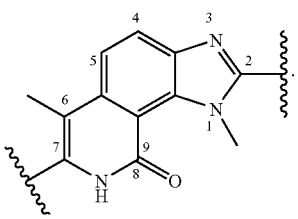

As used herein, "1,7-dimethyl-9-oxo-8,9-dihydro-1H-imidazo[4,5-h]isoquinolin-2,6-ylene" refers to the following structure:

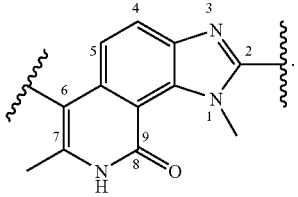

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

An "isocyanato" group refers to a —NCO group.

An "isothiocyanato" group refers to a —NCS group.

The term "moiety" refers to a specific segment or functional group of a molecule. Chemical moieties are often recognized chemical entities embedded in or appended to a molecule.

A "sulfinyl" group refers to a —S(=O)—R.

A "sulfonyl" group refers to a —S(=O)$_2$—R.

A "thioalkoxy" or "alkylthio" group refers to a —S-alkyl group.

As used herein, the term "O-carboxy" or "acyloxy" refers to a group of formula RC(=O)O—.

"Alkylcarbonyloxy" refers to a (alkyl)-C(=O)O— group.

As used herein, the term "alkoxycarbonyl" refers to a group of formula —C(=O)OR.

"Carboxy" means a —C(O)OH radical.

As used herein, the term "acetyl" refers to a group of formula —C(=O)CH$_3$.

"Acyl" refers to the group —C(O)R.

As used herein, the term "trihalomethanesulfonyl" refers to a group of formula X$_3$CS(=O)$_2$— where X is a halogen.

As used herein, the term "cyano" refers to a group of formula —CN.

"Cyanoalkyl" means an alkyl radical, as defined herein, substituted with at least one cyano group.

As used herein, the term "alkylaminosulfonyl" refers to a group of formula —S(=O)$_2$NH(alkyl).

As used herein, the term "dialkylaminosulfonyl" refers to a group of formula —S(=O)$_2$N(alkyl)$_2$.

As used herein, the term "aminosulfonyl" refers to a group of formula —S(=O)$_2$NH$_2$.

As used herein, the term "N-sulfonamido" or "sulfonylamino" refers to a group of formula RS(=O)$_2$NH—.

As used herein, the term "O-carbamyl" refers to a group of formula —OC(=O)NR$_2$.

As used herein, the term "alkylarinocarbonyloxy" refers to a —OC(O)NH(alkyl) group.

As used herein, the term "dialkylaminocarbonyloxy" refers to a —OC(O)N(alkyl)$_2$ group.

"Aminocarbonyloxy" refers to a —OC(O)NH$_2$ group.

As used herein, the term "N-carbamyl" refers to a group of formula ROC(=O)NH—.

As used herein, the term "O-thiocarbamyl" refers to a group of formula —OC(=S)NR$_2$.

As used herein, the term "N-thiocarbamyl" refers to a group of formula ROC(=S)NH—.

As used herein, the term "C-arido" refers to a group of formula —C(=O)NR$_2$.

As used herein, the term "alkylaminocarbonyl" refers to a group of formula —C(=O)NH(alkyl).

As used herein, the term "dialkylaminocarbonyl" refers to a group of formula —C(=O)N(alkyl)$_2$.

"Aminocarbonyl" refers to a —CONH$_2$ radical.

As used herein, the term "N-amido" refers to a group of formula RC(=O)NH—.

"Alkylcarbonylamino" refers to (alkyl)C(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, carbonyl, isocyanato, thiocyanato, isothiocyanato, nitro, perhaloalkyl, fluoroalkyl, silyl, and amino, including mono- and di-substituted amino groups, and the protected derivatives thereof. By way of example an optional substituents may be L$_s$R$_s$, wherein each L$_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each R$_s$ is independently selected from H, (substituted or unsubstituted C$_1$-C$_4$alkyl), (substituted or unsubstituted C$_3$-C$_6$cycloalkyl), heteroaryl, or heteroalkyl. The protecting groups that may form the protective derivatives of the above substituents are known to those of skill in the art and may be found in references such as Greene and Wuts, above.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Throughout the specification, groups and substituents thereof can be chosen by one skilled in the field to provide stable moieties and compounds.

Compounds

Compounds that inhibit the activity of tyrosine kinase(s) can play a role in restoring or promoting health. In certain embodiments, tyrosine kinase inhibitor compounds provided herein are useful in treating any of a variety of diseases, disorders or conditions. In certain embodiments, compounds provided herein are Btk inhibitor compounds.

Described herein are compounds that inhibit the activity of tyrosine kinase(s), such as Btk. Also described herein are pharmaceutically acceptable salts, pharmaceutically acceptable solvates, pharmaceutically active metabolites, and pharmaceutically acceptable prodrugs of such compounds.

Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art.

Compounds provided herein are inhibitors of tyrosine kinase activity, such as Btk. In one embodiment, provided herein is a compound of Formula (Ia). Formula (Ia) is as follows:

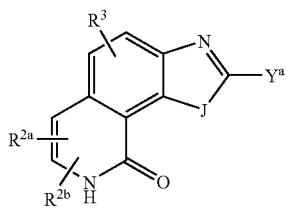

Formula (Ia)

wherein:
- J is —O—, —S—, or —$NR^5$—; where $R^5$ is hydrogen, hydroxy, alkoxy, alkenyloxy, acyl, optionally substituted alkyl, optionally substituted alkenyl, optionally substituted alkynyl, alkoxycarbonyl, aminocarbonyl, alkylaminocarbonyl, dialkylaminocarbonyl, alkylsulfonyl, alkylaminosulfonyl, or dialkylaminosulfonyl; and where alkyl, alkenyl, alkynyl, and alkylene, either alone or as part of another group within J, are independently optionally substituted with one, two, three, four, or five halo;
- $Y^a$ is —$NR^{1a}R^{1b}$, —$OR^{1c}$, or —$SR^{1d}$ where
  - $R^{1a}$ is hydrogen, optionally substituted alkyl, optionally substituted alkenyl, optionally substituted alkynyl, hydroxy, alkoxy, alkenyloxy, acyl, —C(O)N($R^7$)$_2$, —($A^1$)—C(O)$NR^{8a}R^{8b}$, —$SO_2R^6$, -($A^1$)-$SO_2R^6$, —$SO_2N(R^7)_2$, -($A^1$)-$SO_2N(R^7)_2$, —C(O)$OR^6$, -($A^1$)-C(O)$OR^{33}$, cycloalkyl, cycloalkylalkyl, heterocycloalkyl, or heterocycloalkylalkyl;
  - where each $R^7$ is independently selected from among hydrogen, optionally substituted alkyl, optionally substituted alkenyl, optionally substituted alkynyl, cycloalkyl, cycloalkylalkyl, heterocycloalkyl, and heterocycloalkylalkyl;
  - $A^1$ is alkylene, alkenylene, or alkynylene;
  - $R^{8a}$ is substituted alkyl, substituted alkenyl, substituted alkynyl, cycloalkyl, cycloalkylalkyl, heterocycloalkyl, or heterocycloalkylalkyl;
  - $R^{8b}$ is hydrogen or $R^{8a}$;
  - $R^6$ is optionally substituted alkyl, cycloalkyl, cycloalkylalkyl, heterocycloalkyl, or heterocycloalkylalkyl;
  - $R^{33}$ is substituted alkyl, substituted alkenyl, substituted alkynyl, cycloalkyl, cycloalkylalkyl, heterocycloalkyl, or heterocycloalkylalkyl; and
  - where alkyl, alkenyl, alkynyl, and alkylene, either alone or as part of another group within $R^{1a}$, are independently optionally substituted with one, two, three, four, or five halo;
  - $R^{1b}$ is aryl, aralkyl, cycloalkyl, cycloalkylalkyl, heteroaryl, heteroaralkyl, heterocycloalkyl, or heterocycloalkylalkyl or —$X^{1a}$—$Y^1$—$X^{1b}$-$Q^1$ where
    - $X^{1a}$ is a bond, alkylene, alkenylene, alkynylene, cycloalkylene, or heterocycloalkylene where the alkylene, alkenylene, and alkynylene are optionally substituted with one, two, three, four, or five halo or one or two hydroxy;
    - $Y^1$ is a bond, —O—, —S(O)$_{n1}$— (where n1 is 0, 1, or 2), —C(O)—, —$NR^{18}$—, —$NR^{18}$C(O)—, —$NR^{18}$C(O)$NR^8$—, —$NR^{18}$C(=$NR^{18}$)$NR^{18}$—, —C(O)$NR^{18}$—, —OC(O)—, —C(O)O—, —C(O)N($R^{18}$)N=$CR^{27}$—, —$NR^{18}SO_2$—, —$SO_2NR^{18}$—, —C($R^{27}$)(=NO)—, —C($R^{27}$)=$NNR^{18}$—, —C($R^{27}$)=$NNR^{18}$C(O)—, —C($R^{27}$)=$NNR^{18}$C(O)$NR^{18}$—, —$NR^{18}$C(O)O—, or —OC(O)$NR^{18}$—;
      - where $R^{18}$ is hydrogen, optionally substituted alkyl, optionally substituted alkenyl, optionally substituted alkynyl, hydroxy, alkoxy, or alkenyloxy;
      - $R^{27}$ is hydrogen, optionally substituted alkyl, optionally substituted alkenyl, optionally substituted alkynyl; and
      - where alkyl, alkenyl, and alkynyl, either alone or as part of another group within $Y^1$, are independently optionally substituted with one, two, three, four, or five halo;
    - $X^{1b}$ is a bond, alkylene, alkenylene, alkynylene, cycloalkylene, or heterocycloalkylene where the alkylene, alkenylene, and alkynylene are optionally substituted with one, two, three, four, or five halo or one or two hydroxy;
    - $Q^1$ is Z where Z is —P(=E)($Y^{10a}R^{60a}$)($Y^{10b}R^{60b}$), —P($Y^{10a}R^{60a}$)($Y^{10b}R^{60b}$), —P(=E)($Y^{10e}R^{60a}$)($Z^{10}R^{61}$), or an optionally substituted ring system where one ring member is —P(=E)($R^{100}$)—;
    - E is oxygen or sulfur;
    - $Y^{10a}$ and $Y^{10b}$ are independently a single bond, —O—, —S—, or —$NR^{62a}$— where $R^{62a}$ is hydrogen, hydroxy, alkoxy, alkenyloxy, optionally substituted alkyl, optionally substituted alkenyl, or optionally substituted alkynyl;
    - $R^{60a}$ and $R^{60b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is —O—, —S—, or —$NR^{62a}$—;
    - $R^{60a}$ and $R^{60b}$ are independently optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is a single bond;
    - $Y^{10e}$ is —O—, —S—, or —$NR^{62a}$—;
    - $Z^{10}$ is alkylene, alkenylene, alkynylene, —O—, —S—, or —$NR^{62a}$—;
    - $R^{61}$ is hydrogen, acyl, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl; or $R^{61}$ is —P(=E)($Y^{10a}R^{60a}$)($Y^{10b}R^{60b}$);
    - $R^{100}$ is a single bond from the phosphorous atom to $X^{1b}$, or $R^{100}$ is halo, optionally substituted alkyl, optionally substituted alkenyl, optionally substituted alkynyl, optionally substituted phenyl, optionally substituted phenylalkyl, cycloalkyl, cycloalkylalkyl, heterocycloalkyl, heterocycloalkylalkyl, heteroaryl, heteroaralkyl, —$OR^{101}$, or —$NR^{102a}R^{102b}$; and where the alkyl, alkenyl, and alkynyl within $R^{100}$, either alone or as part of another substituent, are independently optionally substituted with one, two, three, four, or five halo;

$R^{101}$ is hydrogen, optionally substituted alkyl, optionally substituted alkenyl, or optionally substituted alkynyl;

$R^{102a}$ and $R^{102b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl;

$R^{1c}$ and $R^{1d}$ are —$X^{1a}$—Z where $X^{1a}$ and Z are as defined above;

$R^{2a}$ is hydrogen, optionally substituted alkyl, optionally substituted alkenyl, optionally substituted alkynyl, hydroxy, alkoxy, alkenyloxy, optionally substituted phenyl, cyano, optionally substituted phenyl, heteroaryl, —$NR^{14a}R^{14b}$, -($A^1$)-$NR^{12a}R^{12b}$, $NR^{13a}C(O)R^{13b}$, -($A^1$)—$NR^{13a}C(O)R^{13b}$, —$C(O)NR^{14a}R^{14b}$, or -($A^1$)—$C(O)NR^{12a}R^{12b}$; and where alkyl, alkenyl, alkynyl, and alkylene, either alone or as part of another group within $R^{2a}$, are independently optionally substituted with one, two, three, four, or five halo;

$R^{12a}$ is substituted alkyl, substituted alkenyl, substituted alkynyl, hydroxy, cyanoalkyl, alkoxy, or alkenyloxy; and $R^{12b}$ is hydrogen or $R^{12a}$;

$R^{14a}$ and $R^{14b}$ are independently hydrogen, optionally substituted alkyl, optionally substituted alkenyl, optionally substituted alkynyl, hydroxy, cyanoalkyl, alkoxy, or alkenyloxy;

$R^{13a}$ is hydrogen, optionally substituted alkyl, optionally substituted alkenyl, optionally substituted alkynyl, hydroxy, cyanoalkyl, alkoxy, alkenyloxy, cycloalkyl, aryl, aralkyl, heteroaryl, or heteroaralkyl and $R^{13b}$ is optionally substituted alkyl, optionally substituted alkenyl, optionally substituted alkynyl, cyanoalkyl, alkoxy, alkenyloxy, or cycloalkyl;

$R^{2b}$ is —$X^{2a}$—$Y^2$—$X^{2b}$-$Q^2$ where $X^{2a}$ is a bond, alkylene, alkenylene, or alkynylene where the alkylene, alkenylene, and alkynylene are optionally substituted with one, two, three, four, or five halo or one or two hydroxy;

$Y^2$ is a bond, —O—, —S(O)$_{1a}$— (where n1 is 0, 1, or 2), —C(O)—, —$NR^{45}$—, —$NR^{45}C(O)$—, —$NR^{45}C(O)NR^{45}$—, —$NR^{45}C(=NR^{45})NR^{45}$—, —$C(O)NR^{45}$—, —OC(O)—, —C(O)O—, —$C(O)N(R^{45})N=CR^{74}$—, —$NR^{45}SO_2$—, —$SO_2NR^{45}$—, —$C(R^{74})(=NO)$—, —$C(R^{74})=NNR^{45}$—, —$C(R^{74})=NNR^{45}C(O)$—, —$C(R^{74})=NNR^{45}C(O)NR^{45}$—, —$NR^{45}C(O)O$—, or —$OC(O)NR^{45}$;

where $R^{45}$ is hydrogen, optionally substituted alkyl, optionally substituted alkenyl, optionally substituted alkynyl, hydroxy, alkoxy, or alkenyloxy;

$R^{74}$ is hydrogen, optionally substituted alkyl, optionally substituted alkenyl, or optionally substituted alkynyl; and where alkyl, alkenyl, and alkynyl, either alone or as part of another group within $Y^2$, are independently optionally substituted with one, two, three, four, or five halo;

$X^{2b}$ is a bond; and $Q^2$ is hydrogen, cyano, optionally substituted alkyl, optionally substituted alkenyl, optionally substituted alkynyl, haloalkyl, haloalkenyl, haloalkynyl, aryl, cycloalkyl, heterocycloalkyl, or heteroaryl; Or $R^{2a}$ and $R^{2b}$ together form cycloalkyl, heterocycloalkyl, aryl, or heteroaryl; and $R^3$ is hydrogen, halo, acyl, acylamino, acyloxy, alkyl, alkenyl, alkynyl, cycloalkyl, cycloalkylalkyl, heterocycloalkyl, heterocycloalkylalkyl, aryl, aralkyl, heteroaryl, heteroaralkyl, -($A^5$)-S(O)$_{0-2}R^{53}$, -($A^5$)-$N(R^{54})_2$, -($A^5$)-$OR^{55}$, -($A^5$)-$OC(O)R^{53}$, -($A^5$)-$C(O)R^{53}$, -($A^5$)-$C(O)OR^{55}$, -($A^5$)-$C(O)N(R^{54})_2$, -($A^5$)-$NR^{54}C(O)R^{53}$, -($A^5$)-$S(O)_2N(R^{54})_2$, -($A^5$)-$NR^{54}S(O)_2R^{53}$, -($A^5$)-$OC(O)N(R^{54})_2$, -($A^5$)-$NR^{54}C(O)OR^{55}$, or -($A^5$)-$NR^{54}C(O)N(R^{54})_2$;

$A^5$ is a bond, alkylene, alkenylene, or alkynylene;

$R^{53}$ is optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl;

$R^{54}$ is hydrogen, optionally substituted alkyl, optionally substituted alkenyl, optionally substituted alkynyl, hydroxy, alkoxy, alkenyloxy, aryl, aralkyl, cycloalkyl, cycloalkylalkyl, heterocycloalkyl, heterocycloalkylalkyl, heteroaryl, or heteroaralkyl;

$R^{55}$ is hydrogen or $R^{53}$; and where alkyl, alkenyl, alkynyl, alkylene, alkenylene, and alkynylene, either alone or as part of another group within $R^3$, are independently optionally substituted with one, two, three, four, or five halo; and pharmaceutically acceptable salts, pharmaceutically acceptable solvates, pharmaceutically acceptable metabolites or pharmaceutically acceptable prodrugs thereof.

In one embodiment, provided herein are compounds of Formula (Ia), wherein $R^3$ is hydrogen and J is —$NR^5$— where $R^5$ is hydrogen or an optionally substituted alkyl. In another embodiment, J is -N(methyl)-.

In another embodiment, $Q^1$ is an optionally substituted ring system where one ring member is —P(=E)($R^{100}$)-.

In some embodiments, $R^{1b}$ is —$X^{1a}$—$Y^1$—$X^{1b}$-$Q^1$. In other embodiments, $Y^a$ is —$NR^{1a}R^{1b}$ where $R^{1a}$ is hydrogen, optionally substituted alkyl, optionally substituted alkenyl, optionally substituted alkynyl, hydroxy, alkoxy, alkenyloxy, or acyl; and $R^{1b}$ is aryl, aralkyl, cycloalkyl, cycloalkylalkyl, heteroaryl, heteroaralkyl, heterocycloalkyl, or heterocycloalkylalkyl. In yet other embodiments, $Y^a$ is —$NR^{1a}R^{1b}$ where $R^{1a}$ is hydrogen and $R^{1b}$ is aryl.

In another embodiment, provided herein is a compound of Formula (Ib). Formula (Ib) is as follows:

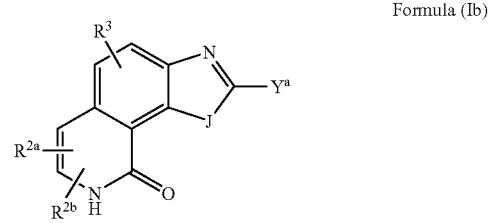

Formula (Ib)

wherein:

J is —O—, —S—, or —$NR^5$—; where $R^5$ is hydrogen, hydroxy, alkoxy, alkenyloxy, acyl, optionally substituted alkyl, optionally substituted alkenyl, optionally substituted alkynyl, alkoxycarbonyl, aminocarbonyl, alkylaminocarbonyl, dialkylaminocarbonyl, alkylsulfonyl, alkylamninosulfonyl, or dialkylamninosulfonyl; and where alkyl, alkenyl, alkynyl, and alkylene, either alone or as part of another group within J, are independently optionally substituted with one, two, three, four, or five halo;

$Y^1$ is —$NR^{1a}R^{1b}$, —$OR^{1c}$, or —$SR^{1d}$ where $R^{1a}$ is hydrogen, optionally substituted alkyl, optionally substituted alkenyl, optionally substituted alkynyl, hydroxy, alkoxy, alkenyloxy, acyl, —$C(O)N(R^7)_2$, -($A^1$)-$C(O)NR^{8a}R^{8b}$, —$SO_2R^6$, -($A^1$)-$SO_2R^6$, —$SO_2N(R^7)_2$, -($A^1$)-$SO_2N(R^7)_2$, —$C(O)OR^6$, -($A^1$)-$C(O)OR^{33}$, cycloalkyl, cycloalkylalkyl, heterocycloalkyl, or heterocycloalkylalkyl;

where each $R^7$ is independently selected from among hydrogen, optionally substituted alkyl, optionally substituted alkenyl, optionally substituted alkynyl, cycloalkyl, cycloalkylalkyl, heterocycloalkyl, and heterocycloalkylalkyl;

$A^1$ is alkylene, alkenylene, or alkynylene;

$R^{8a}$ is substituted alkyl, substituted alkenyl, substituted alkynyl, cycloalkyl, cycloalkylalkyl, heterocycloalkyl, or heterocycloalkylalkyl;

$R^{8b}$ is hydrogen or $R^{8a}$;

$R^6$ is optionally substituted alkyl, cycloalkyl, cycloalkylalkyl, heterocycloalkyl, or heterocycloalkylalkyl;

$R^{33}$ is substituted alkyl, substituted alkenyl, substituted alkynyl, cycloalkyl, cycloalkylalkyl, heterocycloalkyl, or heterocycloalkylalkyl; and where alkyl, alkenyl, alkynyl, and alkylene, either alone or as part of another group within $R^{1a}$, are independently optionally substituted with one, two, three, four, or five halo;

$R^{1b}$ is aryl, aralkyl, cycloalkyl, cycloalkylalkyl, heteroaryl, heteroaralkyl, heterocycloalkyl, or heterocycloalkylalkyl; or $R^{1a}$ and $R^{1b}$ together with the nitrogen to which they are attached form heterocycloalkyl or heteroaryl;

$R^{1c}$ and $R^{1d}$ are independently hydrogen, optionally substituted alkyl, optionally substituted alkenyl, acyl, cycloalkyl, cycloalkylalkyl, heterocycloalkyl, heterocycloalkylalkyl, aryl, aralkyl, heteroaryl, heteroaralkyl, or -($A^{18}$)-$C(O)NR^{50a}R^{50b}$;

$A^{18}$ is alkylene, alkenylene, or alkynylene; and $R^{50a}$ and $R^{50b}$ are independently hydrogen, optionally substituted alkyl, aryl, aralkyl, heteroaryl, heteroaralkyl, cycloalkyl, cycloalkylalkyl, heterocycloalkyl, or heterocycloalkylalkyl); and where alkyl, alkenyl, and alkylene either alone or as part of another group within $R^{1a}$, $R^{1b}$, $R^{1c}$ and $R^{1d}$, are independently optionally substituted with one, two, three, four, or five halo;

$R^{2a}$ is hydrogen, optionally substituted alkyl, optionally substituted alkenyl, optionally substituted alkynyl, hydroxy, alkoxy, alkenyloxy, optionally substituted phenyl, cyano, optionally substituted phenyl, heteroaryl, —$NR^{14a}R^{14b}$, -($A^1$)-$NR^{12a}R^{1b}$, —$NR^{13a}C(O)R^{13b}$, -($A^1$)-$NR^{13a}C(O)R^{13b}$, —$C(O)NR^{14a}R^{14b}$, or -($A^1$)-$C(O)NR^{12a}R^{12b}$; and where alkyl, alkenyl, alkynyl, and alkylene, either alone or as part of another group within $R^{2a}$, are independently optionally substituted with one, two, three, four, or five halo;

$R^{12a}$ is substituted alkyl, substituted alkenyl, substituted alkynyl, hydroxy, cyanoalkyl, alkoxy, or alkenyloxy; and $R^{12b}$ is hydrogen or $R^{12a}$;

$R^{14a}$ and $R^{14b}$ are independently hydrogen, optionally substituted alkyl, optionally substituted alkenyl, optionally substituted alkynyl, hydroxy, cyanoalkyl, alkoxy, or alkenyloxy;

$R^{13a}$ is hydrogen, optionally substituted alkyl, optionally substituted alkenyl, optionally substituted alkynyl, hydroxy, cyanoalkyl, alkoxy, alkenyloxy, cycloalkyl, aryl, aralkyl, heteroaryl, or heteroaralkyl and $R^{13b}$ is optionally substituted alkyl, optionally substituted alkenyl, optionally substituted alkynyl, cyanoalkyl, alkoxy, alkenyloxy, or cycloalkyl;

$R^{2b}$ is —$X^{2a}$—$Y^2$—$X^{2b}$-$Q^3$ where $X^{2a}$ is a bond, alkylene, alkenylene, or alkynylene where the alkylene, alkenylene, and alkynylene are optionally substituted with one, two, three, four, or five halo or one or two hydroxy;

$Y^2$ is a bond, —O—, —$S(O)_{n1}$— (where n1 is 0, 1, or 2), —C(O)—, —$NR^{45}$—, —$NR^{45}C(O)$—, —$NR^{45}C(O)NR^{45}$—, —$NR^{45}C(=NR^{45})NR^{45}$—, —$C(O)NR^{45}$—, —OC(O)—, —C(O)O—, —$C(O)N(R^{45})N=CR^{74}$—, —$NR^{45}SO_2$—, —$SO_2NR^{45}$—, —$C(R^{74})(=NO)$—, —$C(R^{74})=NNR^{45}$—, —$C(R^{74})=NNR^{45}C(O)$—, —$C(R^{74})=NNR^{45}C(O)NR^{45}$—, —$NR^{45}C(O)O$—, or —$OC(O)NR^{45}$—;

where $R^{45}$ is hydrogen, optionally substituted alkyl, optionally substituted alkenyl, optionally substituted alkynyl, hydroxy, alkoxy, or alkenyloxy;

$R^{74}$ is hydrogen, optionally substituted alkyl, optionally substituted alkenyl, or optionally substituted alkynyl; and where alkyl, alkenyl, and alkynyl, either alone or as part of another group within $Y^2$, are independently optionally substituted with one, two, three, four, or five halo;

$X^{2b}$ is a bond, alkylene, alkenylene, alkynylene, cycloalkylene, or heterocycloalkylene where alkylene, alkenylene, and alkynylene are independently optionally substituted with one, two, three, four, or five halo or one or two hydroxy; and $Q^3$ is Z where Z is —$P(=E)(Y^{10a}—R^{60a})(Y^{10b}R^{60b})$, —$P(Y^{10a}R^{60a})(Y^{10b}R^{60b})$, —$P(=E)(Y^{10e}R^{60a})(Z^{10}R^{61})$, or an optionally substituted ring system where one ring member is —$P(=E)(R^{100})$-;

E is oxygen or sulfur;

$Y^{10a}$ and $Y^{10b}$ are independently a single bond, —O—, —S—, or —$NR^{62a}$— where $R^{62a}$ is hydrogen, hydroxy, alkoxy, alkenyloxy, optionally substituted alkyl, optionally substituted alkenyl, or optionally substituted alkynyl;

$R^{60a}$ and $R^{60b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is —O—, —S—, or —$NR^{62a}$—;

$R^{60a}$ and $R^{60b}$ are independently optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is a single bond;

$Y^{10e}$ is —O—, —S—, or —NR$^{62a}$—;

$Z^{10}$ is alkylene, alkenylene, alkynylene, —O—, —S—, or —NR$^{62a}$—;

$R^{61}$ is hydrogen, acyl, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl; or $R^{61}$ is —P(=E)(Y$^{10a}$R$^{60a}$)(Y$^{10b}$R$^{60b}$);

$R^{100}$ is a single bond from the phosphorous atom to X$^{1b}$, or R$^{100}$ is halo, optionally substituted alkyl, optionally substituted alkenyl, optionally substituted alkynyl, optionally substituted phenyl, optionally substituted phenylalkyl, cycloalkyl, cycloalkylalkyl, heterocycloalkyl, heterocycloalkylalkyl, heteroaryl, heteroaralkyl, —OR$^{101}$, or —NR$^{102a}$R$^{102b}$; and where the alkyl, alkenyl, and alkynyl within R$^{100}$, either alone or as part of another substituent, are independently optionally substituted with one, two, three, four, or five halo;

$R^{101}$ is hydrogen, optionally substituted alkyl, optionally substituted alkenyl, or optionally substituted alkynyl;

$R^{102a}$ and $R^{102b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl;

$R^3$ is hydrogen, halo, acyl, acylamino, acyloxy, alkyl, alkenyl, alkynyl, cycloalkyl, cycloalkylalkyl, heterocycloalkyl, heterocycloalkylalkyl, aryl, aralkyl, heteroaryl, heteroaralkyl, -(A$^5$)-S(O)$_{0-2}$R$^{53}$, -(A$^5$)-N(R$^{54}$)$_2$, -(A$^5$)-OR$^{55}$, -(A$^5$)-OC(O)R$^{53}$, -(A$^5$)-C(O)R$^{53}$, -(A$^5$)-C(O)OR$^{55}$, -(A$^5$)-C(O)N(R$^{54}$)$_2$, -(A$^5$)-NR$^{54}$C(O)R$^{53}$, -(A$^5$)-S(O)$_2$N(R$^{54}$)$_2$, -(A$^5$)-NR$^{54}$S(O)$_2$R$^{53}$, -(A$^5$)-OC(O)N(R$^{54}$)$_2$, -(A$^5$)-NR$^{54}$C(O)OR$^{55}$, or -(A$^5$)-NR$^{54}$C(O)N(R$^{54}$)$_2$;

$A^5$ is a bond, alkylene, alkenylene, or alkynylene;

$R^{53}$ is optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl;

$R^{54}$ is hydrogen, optionally substituted alkyl, optionally substituted alkenyl, optionally substituted alkynyl, hydroxy, alkoxy, alkenyloxy, aryl, aralkyl, cycloalkyl, cycloalkylalkyl, heterocycloalkyl, heterocycloalkylalkyl, heteroaryl, or heteroaralkyl;

$R^{55}$ is hydrogen or R$^{53}$; and where alkyl, alkenyl, alkynyl, alkylene, alkenylene, and alkynylene, either alone or as part of another group within R$^3$, are independently optionally substituted with one, two, three, four, or five halo; and pharmaceutically acceptable salts, pharmaceutically acceptable solvates, pharmaceutically acceptable metabolites or pharmaceutically acceptable prodrugs thereof.

In another embodiment, provided herein are compounds of Formula (Ib), wherein R$^3$ is hydrogen and J is —NR$^5$— where R$^5$ is hydrogen or an optionally substituted alkyl. In another embodiment, J is —N(methyl)-.

In some other embodiments, Y$^a$ is —NR$^{1a}$R$^{1b}$ where R$^{1a}$ is hydrogen, optionally substituted alkyl, optionally substituted alkenyl, optionally substituted alkynyl, hydroxy, alkoxy, alkenyloxy, or acyl; and R$^{1b}$ is aryl, aralkyl, cycloalkyl, cycloalkylalkyl, heteroaryl, heteroaralkyl, heterocycloalkyl, or heterocycloalkylalkyl. In another embodiment, Y$^a$ is —NR$^{1a}$R$^{1b}$ where R$^{1a}$ is hydrogen or alkyl and R$^{1b}$ is aryl or heteroaryl. In some other embodiments, Y$^a$ is —NR$^{1a}$R$^{1b}$ where R$^{1a}$ is hydrogen and R$^{1b}$ is aryl. In yet some other embodiments, Y$^a$ is —NH(aryl). In further embodiments, Y$^a$ is 4-fluoro-2-methylphenylamino or 2,6-dichlorophenylamino.

In other embodiments, Q$^3$ is an optionally substituted ring system where one ring member is —P(=E)(R$^{100}$)—.

In other embodiments, R$^{2a}$ is optionally substituted alkyl. In some other embodiments, R$^{2a}$ is methyl; and R$^{2b}$ is —X$^{2a}$—Y$^2$—X$^{2b}$-Q$^2$ where X$^{2a}$ is alkenylene. In yet other embodiments, R$^{2a}$ is methyl; and R$^{2b}$ is —X$^{2a}$—Y$^2$—X$^{2b}$-Q$^2$ where X$^{2a}$ is —CH$_2$CH=CH—. In some other embodiments, Y$^2$ is a bond, —C(O)NR$^{45}$—, or —C(O)NH—. In other embodiments, X$^{2b}$ is a bond, and Q$^2$ is an optionally substituted ring system where one ring member is —P(=E)(R$^{100}$)-. In some other embodiments, R$^{2a}$ is methyl; and R$^{2b}$ is —X$^{2a}$—Y$^2$—X$^{2b}$-Q$^2$ where X$^{2a}$ is —CH$_2$CH=CH—, Y$^2$ is a bond, or —C(O)NH—; X$^{2b}$ is a bond, and Q$^2$ is an optionally substituted ring system where one ring member is —P(=E)(R$^{100}$)—.

In some embodiments, R$^{2a}$ is located at the 6-position and R$^{2b}$ is located at the 7-position.

In some embodiments, Y$^2$ is a bond and Q$^2$ is a saturated, monocyclic group of 6 ring atoms in which one of the ring atoms is nitrogen and another ring member is —P(=O)(R$^{100}$)— and where the nitrogen is the point of attachment to X$^{2b}$. In other embodiments, R$^{100}$ is alkyl, aryl, aralkyl, cycloalkyl, or cycloalkylalkyl. In further embodiments, Q$^2$ is 4-methyl-4-oxo-4λ$^5$-[1,4]azaphosphinan-1-yl; 4-oxo-4-phenyl-4λ$^5$-[1,4]azaphosphinan-1-yl; 4-(4-fluorophenylmethyl)-4-oxo-4λ$^5$-[1,4]azaphosphinan-1-yl; 4-(cyclopropylmethyl)-4-oxo-4λ$^5$-[1,4]azaphosphinan-1-yl; or 4-(cyclopropyl)-4-oxo-4λ$^5$-[1,4]azaphosphinan-1-yl.

In some other embodiments, Y$^2$ is —C(O)NH— and Q$^2$ is a saturated monocyclic hydrocarbon radical of 6 ring atoms where one ring member is —P(=O)(R$^{100}$)—. In other embodiments, R$^{100}$ is alkyl or aryl. In other embodiments, Y$^2$ is —C(O)NH— and Q$^2$ is a saturated monocyclic hydrocarbon radical of 6 ring atoms where one ring member is —P(=O)(R$^{100}$)—; and R$^{100}$ is alkyl or aryl. In yet other embodiments, Q$^2$ is 1-oxo-1-methyl-1λ$^5$-phosphinan-4-yl, 1-oxo-1-trans-phenyl-1λ$^5$-phosphinan-4-yl, or 1-oxo-1-cis-phenyl-1λ$^5$-phosphinan-4-yl.

In another embodiment, J is —NR$^5$—; where R$^5$ is hydrogen; R$^{2a}$ is optionally substituted alkyl; R$^3$ is hydrogen; Y$^a$ is —NR$^{1a}$R$^{1b}$ where R$^{1a}$ is hydrogen or alkyl and R$^{1b}$ is aryl or heteroaryl; R$^{2b}$ is —X$^{2a}$—Y$^2$—X$^{2b}$-Q$^3$ where X$^{2a}$ is alkenylene, Y$^2$ is a bond or —C(O)NH—, X$^{2b}$ is a bond, and Q$^3$ is an optionally substituted ring system where one ring member is —P(=E)(R$^{100}$)— and E is oxygen and R$^{100}$ is alkyl, aryl, aralkyl, cycloalkyl, or cycloalkylalkyl.

In another embodiment, R$^{2a}$ is optionally substituted alkyl; and R$^{2b}$ is —X$^{2a}$—Y$^2$—X$^{2b}$-Q$^2$ where X$^{2a}$ is alkenylene, Y$^2$ is a bond or —C(O)NR$^{45}$—, X$^{2b}$ is a bond, and Q$^2$ is an optionally substituted ring system where one ring member is —P(=E)(R$^{100}$)—.

In another embodiment, provided herein is a compound of Formula (Ic). Formula (Ic) is as follows:

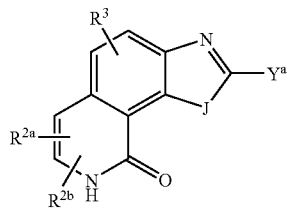

Formula (Ic)

wherein:
- J is —O—, —S—, or —NR$^5$—; where R$^5$ is hydrogen, hydroxy, alkoxy, alkenyloxy, acyl, optionally substituted alkyl, optionally substituted alkenyl, optionally substituted alkynyl, alkoxycarbonyl, aminocarbonyl, alkylaminocarbonyl, dialkylaninocarbonyl, alkylsulfonyl, alkylaminosulfonyl, or dialkylaminosulfonyl; and where alkyl, alkenyl, alkynyl, and alkylene, either alone or as part of another group within J, are independently optionally substituted with one, two, three, four, or five halo;
- Y$^a$ is —NR$^{1a}$R$^{1b}$, —OR$^{1c}$, or —SR$^{1d}$ where
  - R$^{1a}$ is hydrogen, optionally substituted alkyl, optionally substituted alkenyl, optionally substituted alkynyl, hydroxy, alkoxy, alkenyloxy, acyl, —C(O)N(R$^7$)$_2$, -(A$^1$)-C(O)NR$^{8a}$R$^{8b}$, —SO$_2$R$^6$, -(A$^1$)-SO$_2$R$^6$, —SO$_2$N(R$^7$)$_2$, -(A$^1$)-SO$_2$N(R$^7$)$_2$, —C(O)OR$^6$, -(A$^1$)-C(O)OR$^{33}$, cycloalkyl, cycloalkylalkyl, heterocycloalkyl, or heterocycloalkylalkyl;
  - where each R$^7$ is independently selected from among hydrogen, optionally substituted alkyl, optionally substituted alkenyl, optionally substituted alkynyl, cycloalkyl, cycloalkylalkyl, heterocycloalkyl, and heterocycloalkylalkyl;
  - A$^1$ is alkylene, alkenylene, or alkynylene;
  - R$^{8a}$ is substituted alkyl, substituted alkenyl, substituted alkynyl, cycloalkyl, cycloalkylalkyl, heterocycloalkyl, or heterocycloalkylalkyl;
  - R$^{8b}$ is hydrogen or R$^{8a}$;
  - R$^6$ is optionally substituted alkyl, cycloalkyl, cycloalkylalkyl, heterocycloalkyl, or heterocycloalkylalkyl;
  - R$^{33}$ is substituted alkyl, substituted alkenyl, substituted alkynyl, cycloalkyl, cycloalkylalkyl, heterocycloalkyl, or heterocycloalkylalkyl; and
  - where alkyl, alkenyl, alkynyl, and alkylene, either alone or as part of another group within R$^{1a}$, are independently optionally substituted with one, two, three, four, or five halo;
  - R$^{1b}$ is aryl, aralkyl, cycloalkyl, cycloalkylalkyl, heteroaryl, heteroaralkyl, heterocycloalkyl, or heterocycloalkylalkyl; or
  - R$^{1a}$ and R$^{1b}$ together with the nitrogen to which they are attached form heterocycloalkyl or heteroaryl;
  - R$^{1c}$ and R$^{1d}$ are independently hydrogen, optionally substituted alkyl, optionally substituted alkenyl, acyl, cycloalkyl, cycloalkylalkyl, heterocycloalkyl, heterocycloalkylalkyl, aryl, aralkyl, heteroaryl, heteroaralkyl, or -(A$^{18}$)-C(O)NR$^{50a}$R$^{50b}$;
  - A$^{18}$ is alkylene, alkenylene, or alkynylene; and
  - R$^{50a}$ and R$^{50b}$ are independently hydrogen, optionally substituted alkyl, aryl, aralkyl, heteroaryl, heteroaralkyl, cycloalkyl, cycloalkylalkyl, heterocycloalkyl, or heterocycloalkylalkyl); and
  - where alkyl, alkenyl, and alkylene either alone or as part of another group within R$^{1a}$, R$^{1b}$, R$^{1c}$ and R$^{1d}$, are independently optionally substituted with one, two, three, four, or five halo;
- R$^{2a}$ is hydrogen, optionally substituted alkyl, optionally substituted alkenyl, optionally substituted alkynyl, hydroxy, alkoxy, alkenyloxy, optionally substituted phenyl, cyano, optionally substituted phenyl, heteroaryl, —NR$^{14a}$R$^{14b}$, -(A$^1$)-NR$^{12a}$R$^{12b}$, —NR$^{13a}$C(O)R$^{13b}$, -(A$^1$)-NR$^{13a}$C(O)R$^{13b}$, —C(O)NR$^{14a}$R$^{14b}$, or -(A$^1$)-C(O)NR$^{12a}$R$^{12b}$; and
- where alkyl, alkenyl, alkynyl, and alkylene, either alone or as part of another group within R$^{2a}$, are independently optionally substituted with one, two, three, four, or five halo;
- R$^{12a}$ is substituted alkyl, substituted alkenyl, substituted alkynyl, hydroxy, cyanoalkyl, alkoxy, or alkenyloxy; and R$^{12b}$ is hydrogen or R$^{12a}$;
- R$^{14a}$ and R$^{14b}$ are independently hydrogen, optionally substituted alkyl, optionally substituted alkenyl, optionally substituted alkynyl, hydroxy, cyanoalkyl, alkoxy, or alkenyloxy; R$^{13a}$ is hydrogen, optionally substituted alkyl, optionally substituted alkenyl, optionally substituted alkynyl, hydroxy, cyanoalkyl, alkoxy, alkenyloxy, cycloalkyl, aryl, aralkyl, heteroaryl, or heteroaralkyl and R$^{13b}$ is optionally substituted alkyl, optionally substituted alkenyl, optionally substituted alkynyl, cyanoalkyl, alkoxy, alkenyloxy, or cycloalkyl;
- R$^{2b}$ is —X$^{2a}$—Y$^2$—X$^{2b}$-Q$^2$ where
  - X$^{2a}$ is a bond, alkylene, alkenylene, or alkynylene where the alkylene, alkenylene, and alkynylene are optionally substituted with one, two, three, four, or five halo or one or two hydroxy;
  - Y$^2$ is a bond, —O—, —S(O)$_{n1}$— (where n1 is 0, 1, or 2), —C(O)—, —NR$^{45}$—, —NR$^{45}$C(O)—, —NR$^{45}$C(O)NR$^{45}$—, —NR$^{45}$C(=NR$^{45}$)NR$^{45}$—, —C(O)NR$^{45}$—, —OC(O)—, —C(O)O—, —C(O)N(R$^{45}$)N=CR$^{74}$—, —NR$^{45}$O$_2$—, —SO$_2$NR$^{45}$—, —C(R$^{74}$)(=NO)—, —C(R$^{74}$)=NNR$^{45}$—, —C(R$^{74}$)=NNR$^{45}$C(O)—, —C(R$^{74}$)=NNR$^{45}$C(O)NR$^{45}$—, —NR$^{45}$C(O)O—, or —OC(O)NR$^{45}$—;
  - where R$^{45}$ is hydrogen, optionally substituted alkyl, optionally substituted alkenyl, optionally substituted alkynyl, hydroxy, alkoxy, or alkenyloxy;
  - R$^{74}$ is hydrogen, optionally substituted alkyl, optionally substituted alkenyl, or optionally substituted alkynyl; and
  - where alkyl, alkenyl, and alkynyl, either alone or as part of another group within Y$^2$, are independently optionally substituted with one, two, three, four, or five halo;
  - X$^{2b}$ is a bond; and
  - Q$^2$ is hydrogen, cyano, optionally substituted alkyl, optionally substituted alkenyl, optionally substituted alkynyl, haloalkyl, haloalkenyl, haloalkynyl, aryl, cycloalkyl, heterocycloalkyl, or heteroaryl;
- R$^3$ is X$^{3a}$—Y$^3$—X$^{3b}$-Q$^4$ where
  - X$^3$a is a bond, alkylene, alkenylene, or alkynylene where alkylene, alkenylene, and alkynylene are independently optionally substituted with one, two, three, four, or five halo or one or two hydroxy,
  - Y$^3$ is —C(O)—, or —NR$^{51}$— where R$^{51}$ is hydrogen, optionally substituted alkyl, optionally substituted alkenyl, optionally substituted alkynyl, cycloalkyl, cycloalkylalkyl, heterocycloalkyl, or heterocycloalkylalkyl and where alkyl, alkenyl, and alkynyl, either alone or as part of another group within $Y^3$, are independently optionally substituted with one, two, three, four, or five halo, $X^{3b}$ is a bond, alkylene, alkenylene, alkynylene, cycloalkylene, or heterocycloalkylene where alkylene, alkenylene, and alkynylene are independently optionally substituted with one, two, three, four, or five halo or one or two hydroxy, and $Q^4$ is Z where Z is $-P(=E)(Y^{10a}R^{60a})(Y^{10b}R^{60b})$, $-P(Y^{10a}R^{60a})(Y^{10b}R^{60b})$, $-P(=E)(Y^{10e}R^{60a})(Z^{10}R^{61})$, or an optionally substituted ring system where one ring member is $-P(=E)(R^{100})-$;

E is oxygen or sulfur;

$Y^{10a}$ and $Y^{10b}$ are independently a single bond, $-O-$, $-S-$, or $-NR^{62a}-$ where $R^{62a}$ is hydrogen, hydroxy, alkoxy, alkenyloxy, optionally substituted alkyl, optionally substituted alkenyl, or optionally substituted alkynyl;

$R^{60a}$ and $R^{60b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is $-O-$, $-S-$, or $-NR^{62a}-$;

$R^{60a}$ and $R^{60b}$ are independently optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is a single bond; $Y^{10e}$ is $-O-$, $-S-$, or $-NR^{62a}-$;

$Z^{10}$ is alkylene, alkenylene, alkynylene, $-O-$, $-S-$, or $-NR^{62a}-$;

$R^{61}$ is hydrogen, acyl, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl; or $R^{61}$ is $-P(=E)(Y^{10a}R^{60a})(Y^{10b}R^{60b})$;

$R^{100}$ is a single bond from the phosphorous atom to $X^{1b}$, or $R^{100}$ is halo, optionally substituted alkyl, optionally substituted alkenyl, optionally substituted alkynyl, optionally substituted phenyl, optionally substituted phenylalkyl, cycloalkyl, cycloalkylalkyl, heterocycloalkyl, heterocycloalkylalkyl, heteroaryl, heteroaralkyl, $-OR^{101}$, or $-NR^{102a}R^{102b}$; and where the alkyl, alkenyl, and alkynyl within $R^{100}$, either alone or as part of another substituent, are independently optionally substituted with one, two, three, four, or five halo;

$R^{101}$ is hydrogen, optionally substituted alkyl, optionally substituted alkenyl, or optionally substituted alkynyl;

$R^{102a}$ and $R^{102b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl; and pharmaceutically acceptable salts, pharmaceutically acceptable solvates, pharmaceutically acceptable metabolites or pharmaceutically acceptable prodrugs thereof.

In some embodiments, provided herein is a compound of Formula (Ic), wherein J is $-NR^5-$ where $R^5$ is hydrogen or optionally substituted alkyl. In other embodiments, J is $-N(methyl)-$.

In another embodiment, $Y^a$ is $-NR^{1a}R^{1b}$ where $R^{1a}$ is hydrogen, optionally substituted alkyl, optionally substituted alkenyl, optionally substituted alkynyl, hydroxy, alkoxy, alkenyloxy, or acyl; and $R^{1b}$ is aryl, aralkyl, cycloalkyl, cycloalkylalkyl, heteroaryl, heteroaralkyl, heterocycloalkyl, or heterocycloalkylalkyl. In other embodiments, $Y^a$ is $-NR^{1a}R^{1b}$ where $R^{1b}$ is hydrogen or alkyl; and $R^{1b}$ is aryl or heteroaryl. In other embodiments, $Y^a$ is $-NH(aryl)$. In some other embodiments, $Y^a$ is 4-fluoro-2-methylphenylamino or 2,6-dichlorophenylamino.

In another embodiment, $Q^4$ is an optionally substituted ring system where one ring member is $-P(=E)(R^{100})-$.

In one embodiment, provided herein is a compound that has a structure of Formula (II). Formula (II) is as follows:

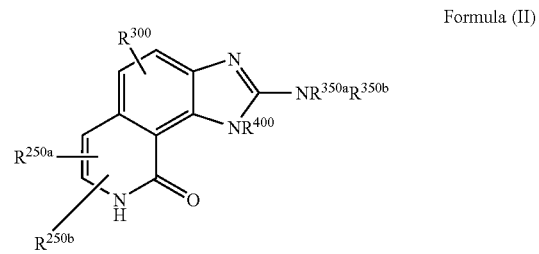

Formula (II)

wherein:

$R^{250a}$ is hydrogen, optionally substituted alkyl, optionally substituted alkenyl, or optionally substituted alkynyl and where alkyl, alkenyl, and alkynyl, are independently optionally substituted with one, two, three, four, or five halo;

$R^{250b}$ is $-CH(=NOH)$, $-C(H)=N-NHC(Q)-Q^{250}$, or $-X^{250a}-Y^{250}-X^{250b}-Q^{250}$ where $X^{250a}$ is alkylene, alkenylene, or alkynylene and where alkylene, alkenylene, and alkynylene are independently optionally substituted with one, two, three, four, or five halo or with one or two hydroxy;

$Y^{250}$ is a bond, $-S-$, $-S(O)-$, $-S(O)_2-$, $-C(O)O-$, or $-OC(O)-$;

$X^{250b}$ is a bond, alkylene, alkenylene, or alkynylene and where alkylene, alkenylene, and alkynylene are independently optionally substituted with one, two, three, four, or five halo or with one or two hydroxy;

$Q^{250}$ is aryl or heteroaryl or $Q^{250}$ is heterocycloalkyl substituted with one or two groups selected from aryl, acyl, heteroaryl, alkylsulfonyl, alkenylsulfonyl, arylsulfonyl, alkoxycarbonyl, alkylaminosulfonyl, dialkylaminosulfonyl, alkylaminocarbonyl, dialkylaminocarbonyl, and $-(alkylene)-R^{251}$;

$R^{251}$ is phenyl substituted with one, two, or three groups selected from among halo, hydroxy, alkoxy, cyano, alkylamino, dialkylamino, acyl, optionally substituted alkyl, optionally substituted alkenyl, optionally substituted alkynyl, alkylsulfonyl, alkenylsulfonyl, alkoxycarbonyl, alkylaminosulfonyl, dialkylaminosulfonyl, alkylaminocarbonyl, and dialkylaminocarbonyl;

and where alkylene, alkyl, alkenyl, and alkynyl, either alone or as part of another group within $R^{250}$, are independently optionally substituted with one, two, three, four, or five halo;

$R^{350a}$ is hydrogen, hydroxy, alkoxy, optionally substituted alkyl, optionally substituted alkenyl, or optionally substituted alkynyl and where alkyl, alkenyl, and alkynyl, are independently optionally substituted with one, two, three, four, or five halo;

$R^{350b}$ is aryl, aralkyl, cycloalkyl, cycloalkylalkyl, heteroaryl, heteroaralkyl, heterocycloalkyl, or heterocycloalkylalkyl and where the alkyl in aralkyl, cycloalkylalkyl, heteroaralkyl, or heterocycloalkylalkyl;

$R^{300}$ is hydrogen, halo, acyl, acylamino, acyloxy, alkyl, alkenyl, alkynyl, cycloalkyl, cycloalkylalkyl, heterocycloalkyl, heterocycloalkylalkyl, aryl, aralkyl, heteroaryl, heteroaralkyl, alkylsulfonyl, alkenylsulfonyl, arylsulfonyl, alkylamino, dialkylamino, alkoxy, acyl, acyloxy, alkoxycarbonyl, alkylaminocarbonyl, dialkylaminocarbonyl, alkylcarbonylamino, aminosulfonyl, alkylaminosulfonyl, dialkylaminosulfonyl, alkylsulfonylamino, or -$A^{100}$-$R^{301}$;

$A^{100}$ is alkylene or alkenylene; and $R^{301}$ is hydrogen, halo, acyl, acylamino, acyloxy, alkyl, alkenyl, alkynyl, cycloalkyl, cycloalkylalkyl, heterocycloalkyl, heterocycloalkylalkyl, aryl, aralkyl, heteroaryl, heteroaralkyl, alkylsulfonyl, alkenylsulfonyl, arylsulfonyl, alkylamino, dialkylamino, alkoxy, acyl, acyloxy, alkoxycarbonyl, alkylaminocarbonyl, dialkylaminocarbonyl, alkylcarbonylamino, aminosulfonyl, alkylaminosulfonyl, dialkylaminosulfonyl, or alkylsulfonylamino; and where alkyl, alkenyl, alkynyl, alkylene, alkenylene, and alkynylene, either alone or as part of another group within $R^{300}$, are independently optionally substituted with one, two, three, four, or five halo; and $R^{400}$ is hydrogen, optionally substituted alkyl, optionally substituted alkenyl, optionally substituted alkynyl, hydroxy, or alkoxy and where alkyl, alkenyl, and alkynyl, either alone or as part of another group within $R^{400}$, are independently optionally substituted with one, two, three, four, or five halo; and pharmaceutically acceptable salts, pharmaceutically acceptable solvates, pharmaceutically acceptable metabolites or pharmnaceutically acceptable prodrugs thereof.

In another embodiment, provided herein is a compound of Formula (II), wherein:

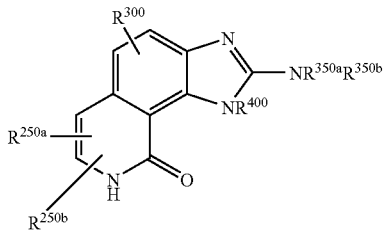

Formula (II)

wherein $R^{250a}$ is hydrogen, optionally substituted alkyl, optionally substituted alkenyl, or optionally substituted alkynyl and where alkyl, alkenyl, and alkynyl, are independently optionally substituted with one, two, three, four, or five halo;

$R^{250b}$ is —$X^{250a}$—$Y^{250}$—$X^{250b}$-$Q^{250}$ where $X^{250a}$ is alkylene, alkenylene, or alkynylene and where alkylene, alkenylene, and alkynylene are independently optionally substituted with one, two, three, four, or five halo or with one or two hydroxy;

$Y^{250}$ is a bond, —S—, —S(O)—, —S(O)$_2$—, —C(O)O—, or —OC(O)—;

$X^{250b}$ is a bond, alkylene, alkenylene, or alkynylene and where alkylene, alkenylene, and alkynylene are independently optionally substituted with one, two, three, four, or five halo or with one or two hydroxy;

$Q^{250}$ is aryl or heteroaryl or $Q^{250}$ is heterocycloalkyl substituted with one or two groups selected from aryl, acyl, heteroaryl, alkylsulfonyl, alkenylsulfonyl, arylsulfonyl, alkoxycarbonyl, alkylaminosulfonyl, dialkylaminosulfonyl, alkylaminocarbonyl, and dialkylaminocarbonyl, and where alkylene, alkyl, alkenyl, and alkynyl, either alone or as part of another group within $R^{250}$, are independently optionally substituted with one, two, three, four, or five halo;

$R^{350a}$ is hydrogen, hydroxy, alkoxy, optionally substituted alkyl, optionally substituted alkenyl, or optionally substituted alkynyl and where alkyl, alkenyl, and alkynyl, are independently optionally substituted with one, two, three, four, or five halo;

$R^{350b}$ is aryl, aralkyl, cycloalkyl, cycloalkylalkyl, heteroaryl, heteroaralkyl, heterocycloalkyl, or heterocycloalkylalkyl and where the alkyl in aralkyl, cycloalkylalkyl, heteroaralkyl, or heterocycloalkylalkyl;

$R^{300}$ is hydrogen, halo, acyl, acylamino, acyloxy, alkyl, alkenyl, alkynyl, cycloalkyl, cycloalkylalkyl, heterocycloalkyl, heterocycloalkylalkyl, aryl, aralkyl, heteroaryl, heteroaralkyl, alkylsulfonyl, alkenylsulfonyl, arylsulfonyl, alkylamino, dialkylamino, alkoxy, acyl, acyloxy, alkoxycarbonyl, alkylaminocarbonyl, dialkylaminocarbonyl, alkylcarbonylamino, aminosulfonyl, alkylaminosulfonyl, dialkylaminosulfonyl, alkylsulfonylamino, or -$A^{100}$-$R^{301}$ (where $A^{100}$ is alkylene or alkenylene and $R^{301}$ is hydrogen, halo, acyl, acylamino, acyloxy, alkyl, alkenyl, alkynyl, cycloalkyl, cycloalkylalkyl, heterocycloalkyl, heterocycloalkylalkyl, aryl, aralkyl, heteroaryl, heteroaralkyl, alkylsulfonyl, alkenylsulfonyl, arylsulfonyl, alkylamino, dialkylamino, alkoxy, acyl, acyloxy, alkoxycarbonyl, alkylaminocarbonyl, dialkylaminocarbonyl, alkylcarbonylamino, aminosulfonyl, alkylaminosulfonyl, dialkylaminosulfonyl, or alkylsulfonylamino) and where alkyl, alkenyl, alkynyl, alkylene, alkenylene, and alkynylene, either alone or as part of another group within $R^{300}$, are independently optionally substituted with one, two, three, four, or five halo; and $R^{400}$ is hydrogen, optionally substituted alkyl, optionally substituted alkenyl, optionally substituted alkynyl, hydroxy, or alkoxy and where alkyl, alkenyl, and alkynyl, either alone or as part of another group within $R^{400}$, are independently optionally substituted with one, two, three, four, or five halo; and pharmaceutically acceptable salts, pharmaceutically acceptable solvates, pharmaceutically acceptable metabolites or pharmaceutically acceptable prodrugs thereof.

In another embodiment, $R^{250a}$ is optionally substituted alkyl; $R^{250b}$ is —CH(=NOH), —C(H)=N—NHC(O)-$Q^{250}$, or —$X^{250a}$—$Y^{250}$—$X^{250b}$-$Q^{250}$ where $X^{250a}$ is alkylene, alkenylene, or alkynylene and where alkylene, alkenylene, and alkynylene are independently optionally substituted with one, two, three, four, or five halo or with one or two hydroxy; $Y^{250}$ is a bond, $-S(O)_2-$, or $-C(O)O-$; $X^{250b}$ is a bond; $Q^{250}$ is aryl or heteroaryl or $Q^{250}$ is heterocycloalkyl substituted with aryl, acyl, heteroaryl, alkylsulfonyl, arylsulfonyl, alkoxycarbonyl, dialkylaminosulfonyl, alkylaminocarbonyl, or -(alkylene)-$R^{251}$ (where $R^{251}$ is phenyl substituted with halo); $R^{350a}$ is hydrogen; $R^{110b}$ is aryl; $R^{300}$ is hydrogen; and $R^{400}$ is optionally substituted alkyl.

In some other embodiments, $R^{350a}$ is hydrogen and $R^{350b}$ is aryl.

In yet some other embodiments, $R^{300}$ is hydrogen and $R^{250a}$ and $R^{400}$ are optionally substituted alkyl.

In some other embodiments, $R^{250b}$ is $R^{250b}$ is $-X^{250a}-Y^{250}-X^{250b}-Q^{250}$ where $X^{250a}$ is $-CH_2CH=CH-$, $Y^{250}$ is a bond, $X^{250b}$ is a bond, and $Q^{250}$ is heterocycloalkyl substituted with one or two groups selected from aryl, acyl, heteroaryl, alkylsulfonyl, alkenylsulfonyl, arylsulfonyl, alkoxycarbonyl, alkylaminosulfonyl, dialkylaminosulfonyl, alkylaminocarbonyl, dialkylaminocarbonyl, and -(alkylene)-$R^{251}$ (where $R^{251}$ is phenyl substituted with one, two, or three groups selected from halo, hydroxy, alkoxy, cyano, alkylamino, dialkylamino, acyl, optionally substituted alkyl, optionally substituted alkenyl, optionally substituted alkynyl, alkylsulfonyl, alkenylsulfonyl, alkoxycarbonyl, alkylaminosulfonyl, dialkylaminosulfonyl, alkylaminocarbonyl, and dialkylaminocarbonyl) and where alkylene, alkyl, alkenyl, and alkynyl, either alone or as part of another group within $R^{250}$, are independently optionally substituted with one, two, three, four, or five halo; and $R^{250b}$ is located at the 7-position. In yet other embodiments, $Q^{250}$ is heterocycloalkyl substituted with one or two groups selected from aryl, acyl, heteroaryl, alkylsulfonyl, alkenylsulfonyl, arylsulfonyl, alkoxycarbonyl, alkylaminosulfonyl, dialkylaminosulfonyl, and -(alkylene)-$R^{251}$ (where $R^{251}$ is phenyl substituted with one, two, or three groups selected from halo, hydroxy, alkoxy, cyano, alkylamino, dialkylamino, acyl, optionally substituted alkyl, optionally substituted alkenyl, optionally substituted alkynyl, alkylsulfonyl, alkenylsulfonyl, alkoxycarbonyl, alkylaminosulfonyl, dialkylaminosulfonyl, alkylaminocarbonyl, and dialkylaminocarbonyl).

In some other embodiments, $Q^{250}$ is piperazin-1-yl substituted at the 4-position of the piperazin-1-yl ring with one group selected from among aryl, acyl, heteroaryl, alkylsulfonyl, arylsulfonyl, alkoxycarbonyl, alkylaminocarbonyl, and alkylaminosulfonyl. In yet other embodiments, $Q^{250}$ is piperazin-1-yl substituted at the 4-position of the piperazin-1-yl ring with one group selected from among aryl, acyl, heteroaryl, alkylsulfonyl, arylsulfonyl, alkoxycarbonyl, and alkylaminosulfonyl.

In one aspect, provided herein are compounds of Formula (III):

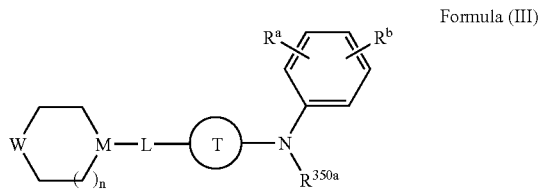

Formula (III)

wherein:

$R^a$ and $R^b$ are each independently selected from among H, halogen, CN, $NO_2$, $C_1$-$C_4$alkyl, $C_1$-$C_4$haloalkyl, and $C_1$-$C_4$alkoxy;

T is 1,6-dimethyl-9-oxo-8,9-dihydro-1H-imidazo[4,5-h]isoquinolin-2,7-ylene, or 1,7-dimethyl-9-oxo-8,9-dihydro-1H-imidazo[4,5-h]isoquinolin-2,6-ylene;

L is $-X^{250a}-Y^{250}-$ or $-Y^{250}-X^{250a}-$, wherein, $X^{250a}$ is a substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;

$Y^{250}$ is a bond, $-O-$, $-S(=O)-$, $-S(=O)_2-$, $-C(=O)-$, $-NR^{45}-$, $-NH-$, $-NHC(=O)-$, $-NR^{45}C(=O)-$, $-NR^{45}C(=O)NR^{45}-$, $-C(=O)NH-$, $-C(=O)NR^{45}-$, $-OC(=O)-$, $-C(=O)O-$, $-NHSO_2-$, $-NR^{45}SO_2-$, $-SO_2NH-$, $-SO_2NR^{45}-$, $-C(R^{45})=NO-$, $-CH=NO-$, $-ON=CH-$, heteroaryl, aryl, $-NHC(=O)O-$, $-OC(=O)NH-$, $-NR^{45}C(=O)O-$, or $-OC(=O)NR^{45}-$;

where each $R^{45}$ is independently selected from among hydrogen, substituted or unsubstituted $C_1$-$C_6$alkyl, substituted or unsubstituted $C_3$-$C_8$cycloalkyl, substituted or unsubstituted $C_2$-$C_6$alkenyl, substituted or unsubstituted $C_2$-$C_6$alkynyl;

M is N or CH;

W is

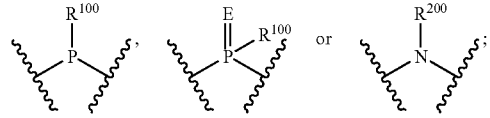

E is oxygen or sulfur;

$R^{100}$ is halogen, $-OH$, or an optionally substituted group selected from among $C_1$-$C_6$alkyl, $C_2$-$C_6$alkenyl, $C_2$-$C_6$alkynyl, phenyl, $C_1$-$C_4$alkyl (phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl ($C_2$-$C_8$heterocycloalkyl), heteroaryl, $C_1$-$C_4$alkyl (heteroaryl), $C_1$-$C_6$alkoxy, $C_1$-$C_6$alkenyloxy, $C_1$-$C_6$alkynyloxy, or $-NR^{102a}R^{102b}$;

$R^{102a}$ and $R^{102b}$ are independently hydrogen, or an optionally substituted group selected from among $C_1$-$C_6$alkyl, $C_2$-$C_6$alkenyl, $C_2$-$C_6$alkynyl, aryl, aralkyl, heteroaryl, heteroaralkyl, $C_3$-$C_8$cycloalkyl, $C_1$-$C_4$alkyl($C_3$-$C_8$cycloalkyl), $C_2$-$C_8$heterocycloalkyl, and $C_1$-$C_4$alkyl($C_2$-$C_8$heterocycloalkyl);

$R^{200}$ is an optionally substituted group selected from among $C_2$-$C_{10}$acyl, $C_2$-$C_6$alkenyl, $C_2$-$C_6$alkynyl, $C_3$-$C_6$cycloalkyl, $C_1$-$C_4$alkyl($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, di($C_1$-$C_6$alkyl)aminosulfonyl, and $C_1$-$C_6$alkylsulfonylamino;

$R^{350a}$ is hydrogen, a substituted or unsubstituted $C_1$-$C_6$alkyl, a substituted or unsubstituted $C_2$-$C_6$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl;

n is 0, 1, or 2; and pharmaceutically active metabolites, pharmaceutically acceptable solvates, pharmaceutically acceptable salts, or pharmaceutically acceptable prodrugs thereof.

For any and all of the embodiments, substituents can be selected from among from a subset of the listed alternatives. For example, in some embodiments, T is 1,6-dimethyl-9-oxo-8,9-dihydro-1H-imidazo[4,5-h]isoquinolin-2,7-ylene. In other embodiments, T is 1,7-dimethyl-9-oxo-8,9-dihydro-1H-imidazo[4,5-h]isoquinolin-2,6-ylene.

In some embodiments, T is 1,6-dimethyl-9-oxo-8,9-dihydro-1H-imidazo[4,5-h]isoquinolin-2,7-ylene substituted at the 2 position with

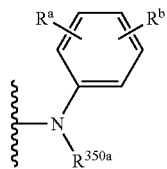

and substituted at the 7 position with

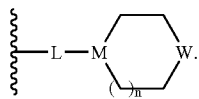

In other embodiment, $Y^{250}$ is a bond, —O—, —S(=O)—, —S(=O)$_2$—, —C(=O)—, —NH—, —NHC(=O)—, —NHC(=O)NH—, —C(=O)NH—, —OC(=O)—, —C(=O)O—, —NHSO$_2$—, —SO$_2$NH—, —NHC(=O)O—, or —OC(=O)NH—; E is O; and $R^{350a}$ is hydrogen, a substituted or unsubstituted $C_1$-$C_6$alkyl, or a substituted or unsubstituted $C_1$-$C_6$haloalkyl.

In some embodiments, $R^{350a}$ is hydrogen or a substituted or unsubstituted $C_1$-$C_6$alkyl. In yet other embodiments, $R^{350a}$ is hydrogen or a $C_1$-$C_6$alkyl. In yet other embodiments, $R^{350a}$ is hydrogen.

In some other embodiments, $X^{250a}$ is a substituted or unsubstituted $C_1$-$C_6$alkyl, substituted or unsubstituted $C_1$-$C_6$baloalkyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl; and n is 1. In other embodiments, $X^{250a}$ is a substituted or unsubstituted $C_1$-$C_6$alkyl, or a substituted or unsubstituted $C_2$-$C_6$alkenyl.

In some embodiments, compounds provided herein have a structure selected from among:

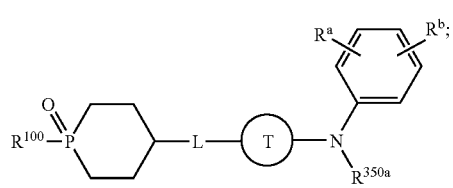

Formula (IIIa)

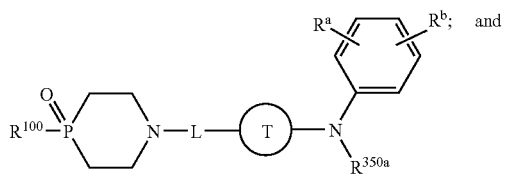

Formula (IIIb)

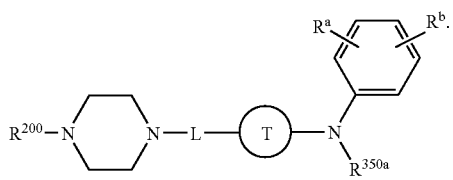

Formula (IIIc)

In certain embodiments, $R^{100}$ is halogen, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), heteroaryl, and $C_1$-$C_4$alkyl(heteroaryl); $R^{200}$ is an optionally substituted group selected from among $C_2$-$C_{10}$acyl, $C_2$-$C_6$alkenyl, $C_2$-$C_6$alkynyl, $C_3$-$C_6$cycloalkyl, $C_1$-$C_4$alkyl ($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In some embodiments, $R^{350a}$ is hydrogen; $Y^{250}$ is a bond, —C(=O)—, —NHC(=O)—, —C(=O)NH—.

In other embodiments, L is selected from among:

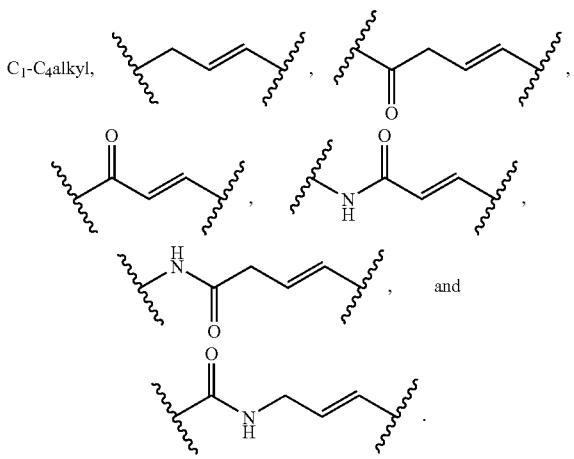

In yet other embodiments, L is selected from among:

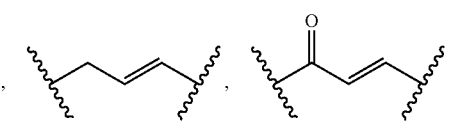

-continued

[chemical structure]

In one embodiment, compounds provided herein have a structure of Formula (IIIc). In other embodiments, compounds provided herein have a structure of Formula (IIIa). In yet other embodiments, compounds provided herein have a structure of Formula (IIIb).

In some embodiments, L is $C_1$-$C_4$ alkyl or

[chemical structure]

and $R^{200}$ is an optionally substituted group selected from among $C_2$-$C_{10}$acyl, aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In other embodiments, $R^{200}$ is an optionally substituted group selected from among $C_2$-$C_{10}$acyl, aryl, heteroaryl, heteroaralkyl, $C_1$-$C_6$alkylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In one aspect, L is selected from among $C_1$-$C_4$ alkyl,

[chemical structures], and

[chemical structure];

$R^{100}$ is an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), heteroaryl, and $C_1$-$C_4$alkyl(heteroaryl); $R^{200}$ is an optionally substituted group selected from among $C_2$-$C_{10}$acyl, aryl, heteroaryl, heteroaralkyl, $C_1$-$C_6$alkylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In some embodiments, T is 1,7-dimethyl-9-oxo-8,9-dihydro-1H-imidazo[4,5-h]isoquinolin-2,6-ylene substituted at the 2 position with

[chemical structure]

and substituted at the 6 position with

[chemical structure]

In yet other embodiments, $Y^{250}$ is a bond, —O—, —S(=O)—, —S(=O)$_2$—, —C(=O)—, —NH—, —NHC(=O)—, —NHC(=O)NH—, —C(=O)NH—, —OC(=O)—, —C(=O)O—, —NHSO$_2$—, —SO$_2$NH—, —NHC(=O)O—, or —OC(=O)NH—; E is O; and $R^{350a}$ is hydrogen, or a substituted or unsubstituted $C_1$-$C_6$alkyl.

In certain embodiments, $X^{250a}$ is a substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl; and n is 1.

In some embodiments, $R^{100}$ is halogen, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), heteroaryl, and $C_1$-$C_4$alkyl(heteroaryl); $R^{200}$ is an optionally substituted group selected from among $C_2$-$C_{10}$acyl, $C_2$-$C_6$alkenyl, $C_2$-$C_6$alkynyl, $C_3$-$C_6$cycloalkyl, $C_1$-$C_4$alkyl($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

In other embodiments, $R^{350a}$ is hydrogen; $Y^{250}$ is —C(=O)—; and $X^{250a}$ is a substituted or unsubstituted $C_1$-$C_6$alkyl.

In certain embodiments, L is

[chemical structure]

In some embodiments, compounds provided herein have a structure of Formula (IIIb). In other embodiments compounds provided herein have a structure of Formula (IIIa). In yet other embodiments, compounds provided herein have a structure of Formula (IIIc).

In another embodiment, provided herein are compounds of Formula (IV):

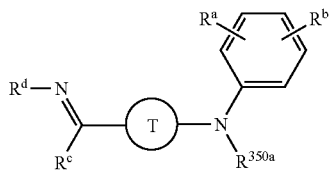

Formula (IV)

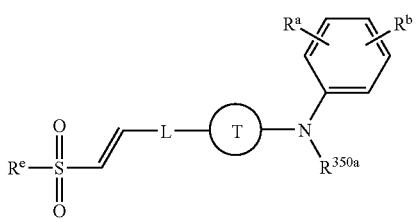

Formula (V)

wherein:

$R^a$ and $R^b$ are each independently selected from among H, halogen, CN, $NO_2$, $C_1$-$C_4$alkyl, $C_1$-$C_4$haloalkyl, and $C_1$-$C_4$alkoxy;

T is 1,6-dimethyl-9-oxo-8,9-dihydro-1H-imidazo[4,5-h]isoquinolin-2,7-ylene;

$R^d$ is —OH, or —NH—C(O)—$R^e$;

$R^c$ is H or $C_1$-$C_4$alkyl, halogen, or $C_1$-$C_4$haloalkyl;

$R^e$ is a substituted or unsubstituted group selected from among $C_1$-$C_6$ alkyl, aryl, or heteroaryl; and pharmaceutically active metabolites, pharmaceutically acceptable solvates, pharmaceutically acceptable salts, or pharmaceutically acceptable prodrugs thereof.

In some embodiments, T is 1,6-dimethyl-9-oxo-8,9-dihydro-1H-imidazo[4,5-h]isoquinolin-2,7-ylene, substituted at the 2 position with

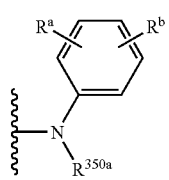

and substituted at the 7 position with

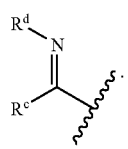

In certain embodiments, $R^c$ is H; and $R^e$ is a substituted or unsubstituted group selected from among aryl, and heteroaryl. In other embodiments, $R^e$ is a substituted or unsubstituted group selected from among phenyl, and heteroaryl containing 1 or 2 N atoms.

In another embodiment, provided herein are compounds of Formula (V):

wherein:

$R^a$ and $R^b$ are each independently selected from among H, halogen, CN, $NO_2$, $C_1$-$C_4$alkyl, $C_1$-$C_4$haloalkyl, and $C_1$-$C_4$alkoxy;

T is 1,6-dimethyl-9-oxo-8,9-dihydro-1H-inidazo[4,5-h]isoquinolin-2,7-ylene, or 1,7-dimethyl-9-oxo-8,9-dihydro-1H-imidazo[4,5-h]isoquinolin-2,6-ylene;

L is —$X^{250a}$—$Y^{250}$—$X^{250b}$— or —$X^{250b}$—$Y^{250}$—$X^{250a}$—, wherein, $X^{250a}$ is a bond, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;

$Y^{250}$ is a bond, —O—, -S(=O)—, —S(=O)$_2$—, —C(=O)—, —$NR^{45}$—, —NH—, —NHC(=O)—, —$NR^{45}$C(=O)—, —$NR^{45}$C(=O)$NR^{45}$—, —C(=O)NH—, —C(=O)$NR^{45}$—, —OC(=O)—, —C(=O)O—, —NHSO$_2$—, —$NR^{45}$SO$_2$—, —SO$_2$NH—, —SO$_2$$NR^{45}$—, —C($R^{45}$)=NO—, —CH=NO—, —ON=CH—, heteroaryl, aryl, —NHC(=O)O—, —OC(=O)NH—, —$NR^{45}$C(=O)O—, or —OC(=O)$NR^{45}$—;

$X^{250b}$ is a bond, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;

where each $R^{45}$ is independently selected from among hydrogen, substituted or unsubstituted $C_1$-$C_6$alkyl, substituted or unsubstituted $C_3$-$C_8$cycloalkyl, substituted or unsubstituted $C_2$-$C_6$alkenyl, substituted or unsubstituted $C_2$-$C_6$alkynyl;

$R^e$ is a substituted or unsubstituted group selected from among $C_1$-$C_6$ alkyl, aryl, and heteroaryl;

$R^{350a}$ is hydrogen, a substituted or unsubstituted $C_1$-$C_6$alkyl, a substituted or unsubstituted $C_2$-$C_6$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl; and pharmaceutically active metabolites, pharmaceutically acceptable solvates, pharmaceutically acceptable salts, or pharmaceutically acceptable prodrugs thereof.

In certain embodiments, T is 1,6-dimethyl-9-oxo-8,9-dihydro-1H-imidazo[4,5-h]isoquinolin-2,7-ylene substituted at the 2 position with

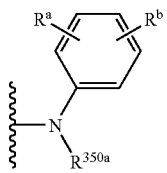

and substituted at the 7 position with

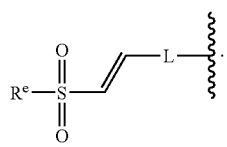

In other embodiments, $Y^{250}$ is a bond; and $R^{350a}$ is hydrogen, a substituted or unsubstituted $C_1$-$C_6$alkyl, a substituted or unsubstituted $C_1$-$C_6$haloalkyl.

In one aspect, $X^{250a}$ is a bond; and $X^{250b}$ is a bond.

In another aspect, T is 1,7-dimethyl-9-oxo-8,9-dihydro-1H-imidazo[4,5-h]isoquinolin-2,7-ylene substituted at the 2 position with

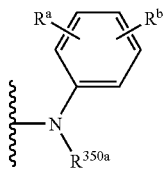

and substituted at the 6 position with

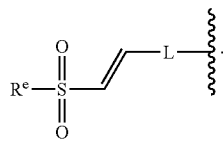

In some embodiments, $X^{250a}$ is a bond, substituted or unsubstituted $C_1$-$C_6$alkyl; $Y^{250}$ is a bond, —O—, —C(=O)—, —NH—, —NHC(=O)—, —NR$^{45}$C(=O)—, —NHC(=O)NH—, —C(=O)NH—, —OC(=O)—, —C(=O)O—, —NHC(=O)O—, or —OC(=O)NH—; and $X^{250b}$ is a bond, substituted or unsubstituted $C_1$-$C_6$alkyl, or substituted or unsubstituted $C_1$-$C_6$haloalkyl.

In some embodiments, $R^e$ is a substituted or unsubstituted group selected from among $C_1$-$C_6$ alkyl, phenyl, and heteroaryl containing 1 or 2 N atoms.

In some embodiments, $R^{350}$, is hydrogen, a substituted or unsubstituted $C_1$-$C_6$alkyl, a substituted or unsubstituted $C_1$-$C_6$haloalkyl.

In other embodiments, $Y^{250}$ is a bond, —NHC(=O)—, —C(=O)NH—, —OC(=O)—, or —C(=O)O—.

In another aspect, provided herein are compounds of Formula (VI):

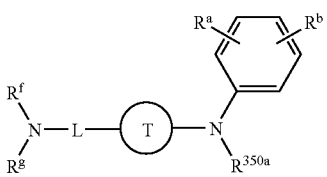

Formula (VI)

wherein:

$R^a$ and $R^b$ are each independently selected from among H, halogen, CN, NO$_2$, $C_1$-$C_4$alkyl, $C_1$-$C_4$haloalkyl, and $C_1$-$C_4$alkoxy;

T is 1,6-dimethyl-9-oxo-8,9-dihydro-1H-imidazo[4,5-h]isoquinolin-2,7-ylene, or 1,7-dimethyl-9-oxo-8,9-dihydro-1H-imidazo[4,5-h]isoquinolin-2,6-ylene;

L is a substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$heteroalkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;

$R^f$ is a substituted or unsubstituted $C_2$-$C_6$alkynyl;

$R^g$ s H, or an optionally substituted group selected from among $C_2$-$C_{10}$acyl, $C_1$-$C_6$alkyl, $C_2$-$C_6$alkenyl, $C_2$-$C_6$alkynyl, $C_3$-$C_6$cycloalkyl, $C_1$-$C_4$alkyl($C_3$-$C_6$cycloalkyl), aryl, heteroaryl, heteroaralkyl, $C_1$-$C_6$alkylsulfonyl, $C_2$-$C_6$alkenylsulfonyl, arylsulfonyl, heteroarylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl;

$R^{350a}$ is hydrogen, a substituted or unsubstituted $C_1$-$C_6$alkyl, a substituted or unsubstituted $C_2$-$C_6$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl; and pharmaceutically active metabolites, pharmaceutically acceptable solvates, pharmaceutically acceptable salts, or pharmaceutically acceptable prodrugs thereof In some embodiments, T is 1,6-dimethyl-9-oxo-8,9-dihydro-1H-imidazo[4,5-h]isoquinolin-2,7-ylene substituted at the 2 position with

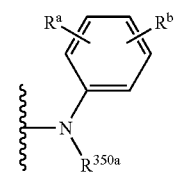

and substituted at the 7 position with

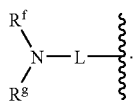

In some embodiments, L is a substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_2$-$C_6$alkenyl, or substituted or unsubstituted $C_2$-$C_6$heteroalkenyl; and $R^{350a}$ is hydrogen, a substituted or unsubstituted $C_1$-$C_6$alkyl. In other embodiments, L is a substituted or unsubstituted $C_1$-$C_6$alkyl, substituted or unsubstituted $C_1$-$C_6$heteroalkyl, substituted or unsubstituted $C_2$-$C_6$alkenyl, or substituted or unsubstituted $C_2$-$C_6$heteroalkenyl.

In other embodiments, $R^g$ is H, or an optionally substituted group selected from among $C_2$-$C_{10}$acyl, $C_1$-$C_6$alkyl, $C_2$-$C_6$alkenyl, $C_2$-$C_6$alkynyl, $C_1$-$C_6$alkylsulfonyl, $C_2$-$C_6$alkenylsulfonyl, arylsulfonyl, heteroarylsulfonyl, or $C_1$-$C_{10}$ alkoxycarbonyl.

In some embodiments, L is a substituted or unsubstituted $C_1$-$C_6$alkyl, or substituted or unsubstituted $C_2$-$C_6$alkenyl; and $R^g$ is H, or an optionally substituted $C_1$-$C_6$alkyl.

In some embodiments, L is selected from among a substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl,

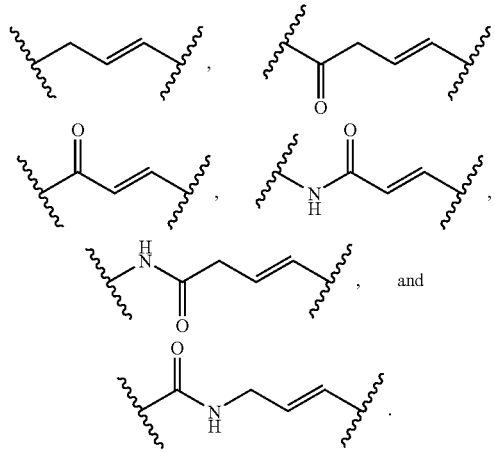

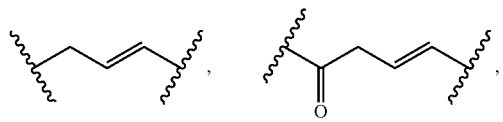

In other embodiments, L is selected from among a substituted or unsubstituted $C_1$-$C_6$alkyl, substituted or unsubstituted $C_2$-$C_6$alkenyl,

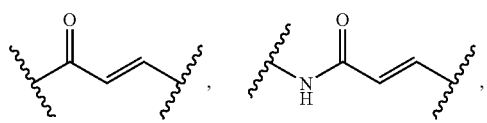

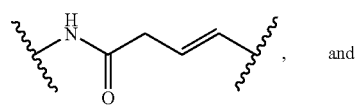

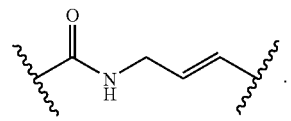

In yet other embodiments, L is selected from among a substituted or unsubstituted $C_1$-$C_6$alkyl, substituted or unsubstituted $C_2$-$C_6$alkenyl,

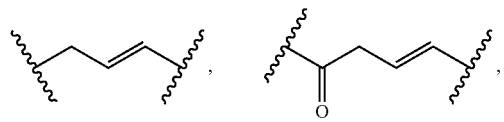

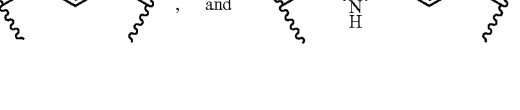

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further embodiments of compounds of Formula (Ia), Formula (Ib), Formula (Ic), Formula (II), Formula (III), (IIIa), Formula (IIIb), Formula (IIIc), Formula (IV), Formula (V), and Formula (VI), include, but are not limited to, compounds shown in Tables 1-6.

TABLE 1

| Cmpd. No. | Q | $X^b$ | Y | $X^a$ | $R^b$ |
|---|---|---|---|---|---|
| 1 | 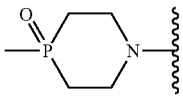 | bond | bond | —CH₂CH=CH— | 4-fluoro-2-methylphenyl |
| 2 |  | bond | bond | —CH₂CH=CH— | 2,6-dichlorophenyl |
| 3 | 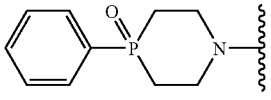 | bond | bond | —CH₂CH=CH— | 4-fluoro-2-methylphenyl |
| 4 | 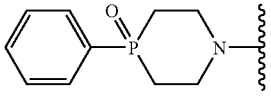 | bond | bond | —CH₂CH=CH— | 3-fluoro-6-methylphenyl |
| 5 | 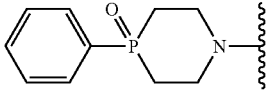 | bond | bond | —CH₂CH=CH— | 2,6-dichlorophenyl |
| 6 | 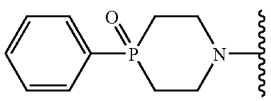 | bond | bond | —CH₂CH=CH— | 2,4-dichloro-6-methylphenyl |
| 7 | 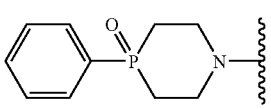 | bond | —C(O)— | —CH=CH— | 3-fluoro-6-methylphenyl |
| 8 | 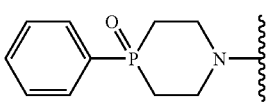 | bond | bond | —CH₂CH₂CH₂— | 2,4-dichloro-6-methylphenyl |
| 9 | 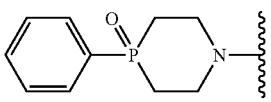 | bond | bond | —CH₂CH₂CH₂— | 4-fluoro-2-methylphenyl |

TABLE 1-continued

[Structure: imidazo[4,5-h]isoquinolin-9-one core with Q—X^b—Y—X^a— substituent and —NHR^b group]

| Cmpd. No. | Q | X^b | Y | X^a | R^b |
|---|---|---|---|---|---|
| 10 | [4-fluorophenyl-phosphinane-oxo-piperazinyl group] | bond | bond | —CH₂CH=CH— | 4-fluoro-2-methylphenyl |
| 11 | [4-methoxyphenyl-phosphinane-oxo-piperazinyl group] | bond | bond | —CH₂CH=CH— | 3-fluoro-6-methylphenyl |

2-(2,4-dichloro-6-methylphenylamino)-1,6-dimethyl-7-[3-(4-oxo-4-phenyl-4λ⁵-[1,4]azaphosphinan-1-yl)-propyl]-1,8-dihydro-imidazo[4,5-h]isoquinolin-9-one (Compound 8);
2-(4-fluoro-2-methylphenylamino)-1,6-dimethyl-7-[3-(4-oxo-4-phenyl-4λ⁵-[1,4]azaphosphinan-1-yl)-propyl]-1,8-dihydro-imidazo[4,5-h]isoquinolin-9-one (Compound 9);
2-(4-fluoro-2-methylphenylamino)-1,6-dimethyl-7-[3-(4-oxo-4-(4-fluorophenyl)-4λ⁵-[1,4]azaphosphinan-1-yl)-propenyl]-1,8-dihydro-imidazo[4,5-h]isoquinolin-9-one (Compound 10);
2-(3-fluoro-6-methylphenylamino)-1,6-dimethyl-7-[3-(4-oxo-4-(4-methoxyphenyl)-4λ⁵-[1,4]azaphosphinan-1-yl)-propenyl]-1,8-dihydro-imidazo[4,5-h]isoquinolin-9-one (Compound 11);
2-(4-fluoro-2-methylphenylamino)-1,6-dimethyl-7-{3-[4-(4-fluorophenylmethyl)-4-oxo-4λ⁵-[1,4]azaphosphinan-1-yl]-propenyl}-1,8-dihydro-imidazo[4,5-h]isoquinolin-9-one (Compound 12);
2-(4-fluoro-2-methylphenylamino)-1,6-dimethyl-7-{3-[4-(cyclopropylmethyl)-4-oxo-4λ⁵-[1,4]azaphosphinan-1-yl]-propenyl}-1,8-dihydro-imidazo[4,5-h]isoquinolin-9-one (Compound 13);
2-(4-fluoro-2-methylphenylamino)-1,6-dimethyl-7-{3-[4-(cyclopropyl)-4-oxo-4λ⁵-[1,4]azaphosphinan-1-yl]-propenyl}-1,8-dihydro-imidazo[4,5-h]isoquinolin-9-one (Compound 14);
2-(4-fluoro-2-methylphenylamino)-1,6-dimethyl-7-{3-[(1-oxo-1-methyl-1λ⁵-phosphinan-4-yl)-carbonylamino]propenyl}-1,8-dihydro-imidazo[4,5-h]isoquinolin-9-one (Compound 15);
2-(4-fluoro-2-methylphenylamino)-1,6-dimethyl-7-{3-[(1-oxo-1-trans-phenyl-1λ⁵-phosphinan-4-yl)-carbonylamino]propenyl}-1,8-dihydro-imidazo[4,5-h]isoquinolin-9-one (Compound 16); and
2-(4-fluoro-2-methyl-phenylamino)-1,6-dimethyl-7-{3-[(1-oxo-1-cis-phenyl-1λ⁵-phosphinan-4-yl)-carbonylamino]propenyl}-1,8-dihydro-imidazo[4,5-h]isoquinolin-9-one (Compound 17).

TABLE 2

[Structure: imidazo[4,5-h]isoquinolin-9-one core with Q—X^b—Y—X^a— substituent and —NHR^b group]

| Cmpd. No. | Q | X^b | Y | X^a | R^b |
|---|---|---|---|---|---|
| 18 | N-phenylpiperazin-1-yl | bond | bond | —CH₂CH=CH— | 2,6-dichlorophenyl |
| 19 | N-phenylpiperazin-1-yl | bond | bond | —CH₂CH=CH— | 4-fluoro-2-methyl-phenyl |
| 20 | N-(4-chlorophenyl)-piperazin-1-yl | bond | bond | —CH₂CH=CH— | 4-fluoro-2-methyl-phenyl |
| 21 | N-(methylcarbonyl)-piperazin-1-yl | bond | bond | —CH₂CH=CH— | 4-fluoro-2-methyl-phenyl |
| 22 | N-(phenylcarbonyl)-piperazin-1-yl | bond | bond | —CH₂CH=CH— | 4-fluoro-2-methyl-phenyl |
| 23 | N-(pyridin-4-yl)-piperazin-1-yl | bond | bond | —CH₂CH=CH— | 4-fluoro-2-methyl-phenyl |
| 24 | N-(methylsulfonyl)-piperazin-1-yl | bond | bond | —CH₂CH=CH— | 4-fluoro-2-methyl-phenyl |
| 25 | N-(methylsulfonyl)-piperazin-1-yl | bond | bond | —CH₂CH=CH— | 3-fluoro-2-methyl-phenyl |
| 26 | N-(pyridin-2-yl)-piperazin-1-yl | bond | bond | —CH₂CH=CH— | 4-fluoro-2-methyl-phenyl |
| 27 | N-(pyrimidin-2-yl)-piperazin-1-yl | bond | bond | —CH₂CH=CH— | 4-fluoro-2-methyl-phenyl |
| 28 | N-(2,6-dichlorophenylmethyl)-piperazin-1-yl | bond | bond | —CH₂CH=CH— | 4-fluoro-2-methyl-phenyl |
| 29 | N-(phenylsulfonyl)-piperazin-1-yl | bond | bond | —CH₂CH=CH— | 4-fluoro-2-methyl-phenyl |
| 30 | N-(4-fluorophenyl)-piperazin-1-yl | bond | bond | —CH₂CH=CH— | 4-fluoro-2-methyl-phenyl |
| 31 | N-(tert-butyloxycarbonyl)-piperazin-1-yl | bond | bond | —CH₂CH=CH— | 4-fluoro-2-methyl-phenyl |
| 32 | N-(N,N-dimethylaminosulfonyl)-piperazin-1-yl | bond | bond | —CH₂CH=CH— | 4-fluoro-2-methyl-phenyl |
| 33 | N-(ethylcarbonyl)-piperazin-1-yl | bond | bond | —CH₂CH=CH— | 4-fluoro-2-methyl-phenyl |
| 34 | N-(isopropylsulfonyl)-piperazin-1-yl | bond | bond | —CH₂CH=CH— | 4-fluoro-2-methyl-phenyl |
| 35 | N-(ethylsulfonyl)-piperazin-1-yl | bond | bond | —CH₂CH=CH— | 4-fluoro-2-methyl-phenyl |

TABLE 2-continued

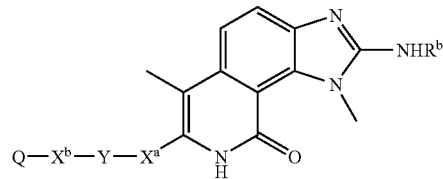

| Cmpd. No. | Q | $X^b$ | Y | $X^a$ | $R^b$ |
|---|---|---|---|---|---|
| 36 | N-(isopropylcarbonyl)-piperazin-1-yl | bond | bond | —CH$_2$CH═CH— | 4-fluoro-2-methyl-phenyl |
| 52 | N-(methylsulfonyl)-piperazin-1-yl | bond | bond | —CH$_2$CH═CH— | 5-fluoro-2-methyl-phenyl |

Compounds in Table 2 are named:

2-(2,6-dichlorophenylamino)-1,6-dimethyl-7-[3-(N-phenylpiperazin-1-yl)-propenyl]-1,8-dihydro-imidazo[4,5-h]isoquinolin-9-one (Compound 18);

2-(4-fluoro-2-methylphenylamino)-1,6-dimethyl-7-[3-(N-phenylpiperazin-1-yl)-propenyl]-1,8-dihydro-inidazo[4,5-h]isoquinolin-9-one (Compound 19);

2-(4-fluoro-2-methylphenylamino)-1,6-dimethyl-7-[3-(N-(4-chlorophenyl)-piperazin-1-yl)-propenyl]-1,8-dihydro-imidazo[4,5-h]isoquinolin-9-one (Compound 20);

2-(4-fluoro-2-methylphenylamino)-1,6-dimethyl-7-[3-(N-methylcarbonylpiperazin-1-yl)-propenyl]-1,8-dihydro-imidazo[4,5-h]isoquinolin-9-one (Compound 21);

2-(4-fluoro-2-methylphenylamino)-1,6-dimethyl-7-[3-(N-phenylcarbonylpiperazin-1-yl)-propenyl]-1,8-dihydro-imidazo[4,5-h]isoquinolin-9-one (Compound 22);

2-(4-fluoro-2-methylphenylamino)-1,6-dimethyl-7-[3-(N-(pyridin-4-yl)-piperazin-1-yl)-propenyl]-1,8-dihydro-inidazo[4,5-h]isoquinolin-9-one (Compound 23);

2-(4-fluoro-2-methylphenylamino)-1,6-dimethyl-7-[3-(N-methylsulfonylpiperazin-1-yl)-propenyl]-1,8-dihydro-inidazo[4,5-h]isoquinolin-9-one (Compound 24);

2-(3-fluoro-2-methylphenylamino)-1,6-dimethyl-7-[3-(N-methylsulfonylpiperazin-1-yl)-propenyl]-1,8-dihydro-imidazo[4,5-h]isoquinolin-9-one (Compound 25);

2-(4-fluoro-2-methylphenylamino)-1,6-dimethyl-7-[3-(N-(pyridin-2-yl)-piperazin-1-yl)-propenyl]-1,8-dihydro-imidazo[4,5-h]isoquinolin-9-one (Compound 26);

2-(4-fluoro-2-methylphenylamino)-1,6-dimethyl-7-[3-(N-(pyrimidin-2-yl)-piperazin-1-yl)-propenyl]-1,8-dihydro-imidazo[4,5-h]isoquinolin-9-one (Compound 27);

2-(4-fluoro-2-methylphenylamino)-1,6-dimethyl-7-[3-(N-(2,6-dichlorophenylmethyl)-piperazin-1-yl)-propenyl]-1,8-dihydro-imidazo[4,5-h]isoquinolin-9-one (Compound 28);

2-(4-fluoro-2-methylphenylamino)-1,6-dimethyl-7-[3-(N-phenylsulfonylpiperazin-1-yl)-propenyl]-1,8-dihydro-imidazo[4,5-h]isoquinolin-9-one (Compound 29);

2-(4-fluoro-2-methylphenylamino)-1,6-dimethyl-7-[3-(N-(4-fluorophenyl)-piperazin-1-yl)-propenyl]-1,8-dihydro-imidazo[4,5-h]isoquinolin-9-one (Compound 30);

2-(4-fluoro-2-methylphenylamino)-1,6-dimethyl-7-[3-(N-tert-butyloxycarbonylpiperazin-1-yl)-propenyl]-1,8-dihydro-imidazo[4,5-h]isoquinolin-9-one (Compound 31);

2-(4-fluoro-2-methylphenylamino)-1,6-dimethyl-7-[3-(N-(N,N-dimethylaminosulfonyl)-piperazin-1-yl)-propenyl]-1,8-dihydro-imidazo[4,5-h]isoquinolin-9-one (Compound 32);

2-(4-fluoro-2-methylphenylamino)-1,6-dimethyl-7-[3-(N-ethylcarbonylpiperazin-1-yl)-propenyl]-1,8-dihydro-imidazo[4,5-h]isoquinolin-9-one (Compound 33);

2-(4-fluoro-2-methylphenylamino)-1,6-dimethyl-7-[3-(N-(isopropylsulfonyl)-piperazin-1-yl)-propenyl]-1,8-dihydro-imidazo[4,5-h]isoquinolin-9-one (Compound 34);

2-(4-fluoro-2-methylphenylamino)-1,6-dimethyl-7-[3-(N-(ethylsulfonyl)-piperazin-1-yl)-propenyl]-1,8-dihydro-imidazo[4,5-h]isoquinolin-9-one (Compound 35); and 2-(4-fluoro-2-methylphenylamino)-1,6-dimethyl-7-[3-(N-isopropylcarbonylpiperazin-1-yl)-propenyl]-1,8-dihydro-imidazo[4,5-h]isoquinolin-9-one (Compound 36).

TABLE 3

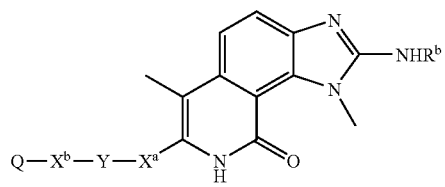

| Cmpd. No. | Q | $X^b$ | Y | $X^a$ | $R^b$ |
|---|---|---|---|---|---|
| 37 | phenyl | bond | —S(O)$_2$— | —CH═CH— | 2,6-dichlorophenyl |
| 38 | phenyl | bond | —C(O)O— | prop-2-en-1,1-diyl | 2,6-dichlorophenyl |
| 39 | phenyl | bond | —C(O)O— | 2,2-difluorobutyn-1,1-diyl | 2,6-dichlorophenyl |

TABLE 3-continued

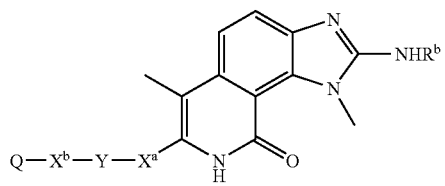

| Cmpd. No. | Q | $X^b$ | Y | $X^a$ | $R^b$ |
|---|---|---|---|---|---|
| 40 | N-phenylmethyl-[1,2,3]triazol-4-yl | bond | bond | —CF$_3$CH(OH)— | 2,6-dichlorophenyl |
| 41 | phenyl | bond | bond | —C≡CCH(OH)— | 2,6-dichlorophenyl |

Compounds in Table 3 are named:

2-(2,6-dichlorophenylamino)-1,6-dimethyl-7-[2-(phenylsulfonyl)-ethenyl]-1,8-dihydro-imidazo[4,5-h]isoquinolin-9-one (Compound 37);

2-(2,6-dichlorophenylamino)-1,6-dimethyl-7-[1-(phenylcarbonyloxy)-prop-2-enyl]-1,8-dihydro-imidazo[4,5-h]isoquinolin-9-one (Compound 38);

2-(2,6-dichlorophenylamino)-1,6-dimethyl-7-[1-(phenylcarbonyloxy)-2,2-difluorobutynyl]-1,8-dihydro-imidazo[4,5-h]isoquinolin-9-one (Compound 39);

2-(2,6-dichlorophenylamino)-1,6-dimethyl-7-[2,2-difluoro-1-hydroxy-2-(N-phenylmethyl-[1,2,3]triazol-4-yl)-ethyl]-1,8-dihydro-imidazo[4,5-h]isoquinolin-9-one (Compound 40);

2-(2,6-dichlorophenylamino)-1,6-dimethyl-7-(1-hydroxy-3-phenylprop-2-yn-1-yl)-1,8-dihydro-imidazo[4,5-h]isoquinolin-9-one (Compound 41);

TABLE 4

| Cmpd. No. | $R^f$ | $R^g$ | L | $R^b$ |
|---|---|---|---|---|
| 42 | prop-1-yn-3-yl | methyl | —CH$_2$CH=CH— | 2,6-dichlorophenyl |
| 43 | prop-1-yn-3-yl | methyl | —CH$_2$CH=CH— | 4-fluoro-2-methylphenyl |

Compounds in Table 4 are named:

2-(2,6-dichlorophenylamino)-1,6-dimethyl-7-[3-(N-methyl-N-(prop-2-ynyl)amino)prop-1-enyl]-1,8-dihydro-imidazo[4,5-h]isoquinolin-9-one (Compound 42); and 2-(4fluoro-2-methylphenylamino)-1,6dimethyl-7-[3-(N-methyl-N-prop-2-ynyl)amino)prop1-enyl]-1,8-dihydro- imidazo[4,5h]isoquinlin-9-one(compound 43);

TABLE 5

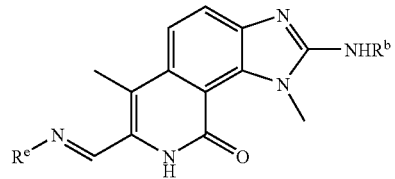

| Cmpd. No. | $R^e$ | $R^b$ |
|---|---|---|
| 44 | —OH | 2,6-dichlorophenyl |
| 45 | phenylamido | 2,6-dichlorophenyl |
| 46 | 4-(N,N-dimethylamino)-phenylamido | 2,6-dichlorophenyl |
| 47 | (pyridin-2-yl)amido | 2,6-dichlorophenyl |
| 48 | (pyridin-3-yl)amido | 2,6-dichlorophenyl |
| 49 | 2-methoxyphenylamido | 2,6-dichlorophenyl |

Compounds in Table 5 are named:

2-(2,6-dichlorophenylamino)-1,6-dimethyl-9-oxo-8,9-dihydro-1H-imidazo[4,5-h]isoquinoline-7-carbaldehyde oxime (Compound 44);

benzoic acid [2-(2,6-dichlorophenylamino)-1,6-dimethyl-9-oxo-8,9-dihydro-1H-imidazo[4,5-h]isoquinolin-7-ylmethylene]-hydrazide (Compound 45);

4-(N,N-dimethylamino)-benzoic acid [2-(2,6-dichlorophenylamino)-1,6-dimethyl-9-oxo-8,9-dihydro-1H-imidazo[4,5-h]isoquinolin-7-ylmethylene]-hydrazide (Compound 46);

pyridine-2-carboxylic acid [2-(2,6-dichlorophenylamino)-1,6-dimethyl-9-oxo-8,9-dihydro-1H-imidazo[4,5-h]isoquinolin-7-ylmethylene]-hydrazide (Compound 47);

pyridine-3-carboxylic acid [2-(2,6-dichlorophenylamino)-1,6-dimethyl-9-oxo-8,9-dihydro-1H-imidazo[4,5-h]isoquinolin-7-ylmethylene]-hydrazide (Compound 48); and 2-methoxy-benzoic acid [2-(2,6-dichlorophenylamino)-1,6-dimethyl-9-oxo-8,9-dihydro-1H-imidazo[4,5-h]isoquinolin-7-ylmethylene]-hydrazide (Compound 49).

TABLE 6

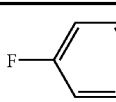

| Cmpd. No. | Q | X^b | Y | X^a | R^b |
|---|---|---|---|---|---|
| 50 | 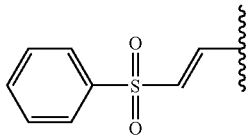 | bond | —C(O)— | —CH$_2$— | 4-fluoro-2-methylphenyl |
| 51 | 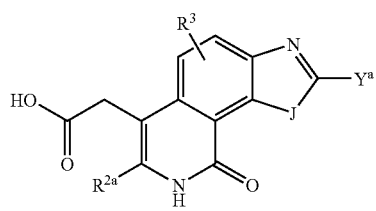 | butan-1-diyl | —NHC(O)— | —CH$_2$— | 4-fluoro-2-methyl-phenyl |

Compounds in Table 6 are named:

2-(4-fluoro-2-methylphenylamino)-1,7-dimethyl-6-{2-[4-(4-flourophenyl)-4-oxo-4λ$^5$[1,4]azaphosphinan-1-yl]-2-oxoethyl}-1,8-dihydro-imidazo[4,5-h]isoquinolin-9-one (Compound 50); and (S)-2-(4-fluoro-2-methylphenylamino)-1,7-dimethyl-6-{N-[1-(phenylsulfonyl)hex-1-en-3-yl]-amino-2-oxoethyl}-1,8-dihydro-imidazo[4,5-h]isoquinolin-9-one (Compound 51).

In one embodiment, provided herein is an optionally substituted ring system, where one ring member is —P(=E)(R$^{100}$)—, of structure 34:

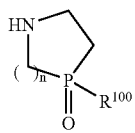

34 wherein:
E is oxygen;
R$^{100}$ is defined herein; and
n is 1, 2, or 3.

In another embodiment, provided herein is an optionally substituted ring system where one ring member is —P(=E)(R$^{100}$)—, of structure 9:

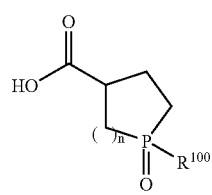

9 wherein
E is oxygen;
R$^{100}$ is defined herein;
and n is 1, 2, or 3.

In another embodiment, provided herein is a process of preparing a compound of Formula (Ia), Formula (Ib) or Formula (Ic), which includes:

(a) reacting an optionally substituted ring system of structure 34:

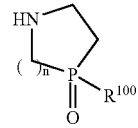

34

(a) with a carboxylic acid (or a salt thereof or an activated acid derivative thereof) of structure I(i):

I(i)

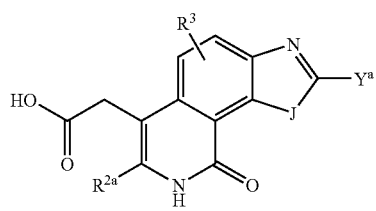

wherein:
J is —O—, —S—, or —NR$^5$—; where R$^5$ is hydrogen, hydroxy, alkoxy, alkenyloxy, acyl, optionally substituted alkyl, optionally substituted alkenyl, optionally substituted alkynyl, alkoxycarbonyl, aminocarbonyl, alkylaminocarbonyl, dialkylaminocarbonyl, alkylsulfonyl, alkylaminosulfonyl, or dialkylaminosulfonyl; and where alkyl, alkenyl, alkynyl, and alkylene, either alone or as part of another group within J, are independently optionally substituted with one, two, three, four, or five halo;

$Y^a$ is —NR$^{1a}$R$^{1b}$, —OR$^{1c}$, or —SR$^{1d}$ where

R$^{1a}$ is hydrogen, optionally substituted alkyl, optionally substituted alkenyl, optionally substituted alkynyl, hydroxy, alkoxy, alkenyloxy, acyl, —C(O)N(R$^7$)$_2$, -(A$^1$)-C(O)NR$^{8a}$R$^{8b}$, —SO$_2$R$^6$, -(A$^1$)-SO$_2$R$^6$, —SO$_2$N(R$^7$)$_2$, -(A$^1$)-SO$_2$N(R$^7$)$_2$, —C(O)OR$^6$, -(A$^1$)-C(O)OR$^{33}$, cycloalkyl, cycloalkylalkyl, heterocycloalkyl, or heterocycloalkylalkyl;

where each R$^7$ is independently selected from among hydrogen, optionally substituted alkyl, optionally substituted alkenyl, optionally substituted alkynyl, cycloalkyl, cycloalkylalkyl, heterocycloalkyl, and heterocycloalkylalkyl;

A$^1$ is alkylene, alkenylene, or alkynylene;

R$^{8a}$ is substituted alkyl, substituted alkenyl, substituted alkynyl, cycloalkyl, cycloalkylalkyl, heterocycloalkyl, or heterocycloalkylalkyl;

R$^{8b}$ is hydrogen or R$^{8a}$;

R$^6$ is optionally substituted alkyl, cycloalkyl, cycloalkylalkyl, heterocycloalkyl, or heterocycloalkylalkyl;

R$^{33}$ is substituted alkyl, substituted alkenyl, substituted alkynyl, cycloalkyl, cycloalkylalkyl, heterocycloalkyl, or heterocycloalkylalkyl; and where alkyl, alkenyl, alkynyl, and alkylene, either alone or as part of another group within R$^{1a}$, are independently optionally substituted with one, two, three, four, or five halo;

R$^{1b}$ is aryl, aralkyl, cycloalkyl, cycloalkylalkyl, heteroaryl, heteroaralkyl, heterocycloalkyl, or heterocycloalkylalkyl; or R$^{1a}$ and R$^{1b}$ together with the nitrogen to which they are attached form heterocycloalkyl or heteroaryl;

R$^{1c}$ and R$^{1d}$ are independently hydrogen, optionally substituted alkyl, optionally substituted alkenyl, acyl, cycloalkyl, cycloalkylalkyl, heterocycloalkyl, heterocycloalkylalkyl, aryl, aralkyl, heteroaryl, heteroaralkyl, or -(A$^{18}$)-C(O)NR$^{50a}$R$^{50b}$;

A$^{18}$ is alkylene, alkenylene, or alkynylene; and

R$^{50a}$ and R$^{50b}$ are independently hydrogen, optionally substituted alkyl, aryl, aralkyl, heteroaryl, heteroaralkyl, cycloalkyl, cycloalkylalkyl, heterocycloalkyl, or heterocycloalkylalkyl); and where alkyl, alkenyl, and alkylene either alone or as part of another group within R$^{1a}$, R$^{1b}$, R$^{1c}$ and R$^{1d}$, are independently optionally substituted with one, two, three, four, or five halo;

R$^{2a}$ is hydrogen, optionally substituted alkyl, optionally substituted alkenyl, optionally substituted alkynyl, hydroxy, alkoxy, alkenyloxy, optionally substituted phenyl, cyano, optionally substituted phenyl, heteroaryl, —NR$^{14a}$R$^{14b}$, -(A$^1$)NR$^{12a}$R$^{12b}$, —NR$^{13a}$C(O)R$^{13b}$, -(A$^1$)-NR$^{13a}$C(O)R$^{13b}$, —C(O)NR$^{14a}$R$^{14b}$, or -(A$^1$)-C(O)NR$^{12a}$R$^{12b}$; and where alkyl, alkenyl, alkynyl, and alkylene, either alone or as part of another group within R$^{2a}$, are independently optionally substituted with one, two, three, four, or five halo;

R$^{12a}$ is substituted alkyl, substituted alkenyl, substituted alkynyl, hydroxy, cyanoalkyl, alkoxy, or alkenyloxy; and R$^{12b}$ is hydrogen or R$^{12a}$;

R$^{14a}$ and R$^{14b}$ are independently hydrogen, optionally substituted alkyl, optionally substituted alkenyl, optionally substituted alkynyl, hydroxy, cyanoalkyl, alkoxy, or alkenyloxy;

R$^{13a}$ is hydrogen, optionally substituted alkyl, optionally substituted alkenyl, optionally substituted alkynyl, hydroxy, cyanoalkyl, alkoxy, alkenyloxy, cycloalkyl, aryl, aralkyl, heteroaryl, or heteroaralkyl and R$^{13b}$ is optionally substituted alkyl, optionally substituted alkenyl, optionally substituted alkynyl, cyanoalkyl, alkoxy, alkenyloxy, or cycloalkyl;

R$^3$ is hydrogen, halo, acyl, acylamino, acyloxy, alkyl, alkenyl, alkynyl, cycloalkyl, cycloalkylalkyl, heterocycloalkyl, heterocycloalkylalkyl, aryl, aralkyl, heteroaryl, heteroaralkyl, -(A$^5$)-S(O)$_{0-2}$R$^{53}$, -(A$^5$)-N(R$^{54}$)$_2$, -(A$^5$)-OR$^{55}$, -(A$^5$)-OC(O)R$^{53}$, -(A$^5$)-C(O)R$^{53}$, -(A$^5$)-C(O)OR$^{55}$, -(A$^5$)-C(O)N(R$^{54}$)$_2$, -(A$^5$)-NR$^{54}$C(O)R$^{53}$, -(A$^5$)-S(O)$_2$N(R$^{54}$)$_2$, -(A$^5$)-NR$^{54}$S(O)$_2$R$^{53}$, -(A$^5$)-OC(O)N(R$^{54}$)$_2$, -(A$^5$)-NR$^{54}$C(O)OR$^{55}$, or -(A$^5$)-NR$^{54}$C(O)N(R$^{54}$)$_2$;

A$^5$ is a bond, alkylene, alkenylene, or alkynylene;

R$^{53}$ is optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl;

R$^{54}$ is hydrogen, optionally substituted alkyl, optionally substituted alkenyl, optionally substituted alkynyl, hydroxy, alkoxy, alkenyloxy, aryl, aralkyl, cycloalkyl, cycloalkylalkyl, heterocycloalkyl, heterocycloalkylalkyl, heteroaryl, or heteroaralkyl;

R$^{55}$ is hydrogen or R$^{53}$; and where alkyl, alkenyl, alkynyl, alkylene, alkenylene, and alkynylene, either alone or as part of another group within R$^3$, are independently optionally substituted with one, two, three, four, or five halo; to give a compound of formula I(b):

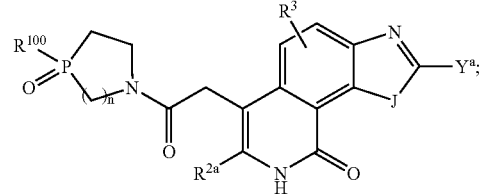

or (b) with an intermediate of formula I(h):

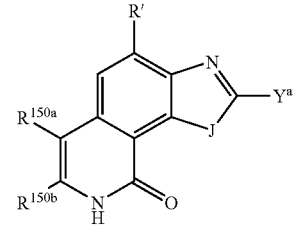

or a salt thereof, where R' is a leaving group such as halo;

J is —O—, —S—, or —NR$^5$—; where R$^5$ is hydrogen, hydroxy, alkoxy, alkenyloxy, acyl, optionally substituted alkyl, optionally substituted alkenyl, optionally substituted alkynyl, alkoxycarbonyl, aminocarbonyl, alkylaminocarbonyl, dialkylaminocarbonyl, alkylsulfonyl, alkylaminosulfonyl, or dialkylaminosulfonyl; and where alkyl, alkenyl, alkynyl, and alkylene, either alone or as part of another group within J, are independently optionally substituted with one, two, three, four, or five halo;

$Y^a$ is $-NR^{1a}R^{1b}$, $-OR^{1c}$, or $-SR^{1d}$ where $R^{1a}$ is hydrogen, optionally substituted alkyl, optionally substituted alkenyl, optionally substituted alkynyl, hydroxy, alkoxy, alkenyloxy, acyl, $-C(O)N(R^7)_2$, $-(A^1)-C(O)NR^{8a}R^{8b}$, $-SO_2R^6$, $-(A^1)-SO_2R^6$, $-SO_2N(R^7)_2$, $-(A^1)-SO_2N(R^7)_2$, $-C(O)OR^6$, $-(A^1)-C(O)OR^{33}$, cycloalkyl, cycloalkylalkyl, heterocycloalkyl, or heterocycloalkylalkyl;

where each $R^7$ is independently selected from among hydrogen, optionally substituted alkyl, optionally substituted alkenyl, optionally substituted alkynyl, cycloalkyl, cycloalkylalkyl, heterocycloalkyl, and heterocycloalkylalkyl;

$A^1$ is alkylene, alkenylene, or alkynylene;

$R^{8a}$ is substituted alkyl, substituted alkenyl, substituted alkynyl, cycloalkyl, cycloalkylalkyl, heterocycloalkyl, or heterocycloalkylalkyl;

$R^{8b}$ is hydrogen or $R^{8a}$;

$R^6$ is optionally substituted alkyl, cycloalkyl, cycloalkylalkyl, heterocycloalkyl, or heterocycloalkylalkyl;

$R^{33}$ is substituted alkyl, substituted alkenyl, substituted alkynyl, cycloalkyl, cycloalkylalkyl, heterocycloalkyl, or heterocycloalkylalkyl; and where alkyl, alkenyl, alkynyl, and alkylene, either alone or as part of another group within $R^{1a}$, are independently optionally substituted with one, two, three, four, or five halo;

$R^{1b}$ is aryl, aralkyl, cycloalkyl, cycloalkylalkyl, heteroaryl, heteroaralkyl, heterocycloalkyl, or heterocycloalkylalkyl; or $R^{1a}$ and $R^{1b}$ together with the nitrogen to which they are attached form heterocycloalkyl or heteroaryl;

$R^{1c}$ and $R^{1d}$ are independently hydrogen, optionally substituted alkyl, optionally substituted alkenyl, acyl, cycloalkyl, cycloalkylalkyl, heterocycloalkyl, heterocycloalkylalkyl, aryl, aralkyl, heteroaryl, heteroaralkyl, or $-(A^1)-C(O)NR^{50a}R^{50b}$;

$A^{18}$ is alkylene, alkenylene, or alkynylene; and $R^{50a}$ and $R^{50b}$ are independently hydrogen, optionally substituted alkyl, aryl, aralkyl, heteroaryl, heteroaralkyl, cycloalkyl, cycloalkylalkyl, heterocycloalkyl, or heterocycloalkylalkyl); and where alkyl, alkenyl, and alkylene either alone or as part of another group within $R^{1a}$, $R^{1b}$, $R^{1c}$ and $R^{1d}$, are independently optionally substituted with one, two, three, four, or five halo;

$R^{150a}$ is $R^{2a}$ and $R^{150b}$ is $R^{2b}$;

or $R^{150a}$ is $R^{2b}$ and $R^{150b}$ is $R^{2a}$;

$R^{2a}$ is hydrogen, optionally substituted alkyl, optionally substituted alkenyl, optionally substituted alkynyl, hydroxy, alkoxy, alkenyloxy, optionally substituted phenyl, cyano, optionally substituted phenyl, heteroaryl, $-NR^{14a}R^{14b}$, $-(A^1)-NR^{12a}R^{12b}$, $-NR^{13a}C(O)R^{13b}$, $-(A^1)-NR^{13a}C(O)R^{13b}$, $-C(O)NR^{14a}R^{14b}$, or $-(A^1)-C(O)NR^{12a}R^{12b}$; and where alkyl, alkenyl, alkynyl, and alkylene, either alone or as part of another group within $R^{2a}$, are independently optionally substituted with one, two, three, four, or five halo;

$R^{12}$ is substituted alkyl, substituted alkenyl, substituted alkynyl, hydroxy, cyanoalkyl, alkoxy, or alkenyloxy; and $R^{12b}$ is hydrogen or $R^{12a}$;

$R^{14a}$ and $R^{14b}$ are independently hydrogen, optionally substituted alkyl, optionally substituted alkenyl, optionally substituted alkynyl, hydroxy, cyanoalkyl, alkoxy, or alkenyloxy;

$R^{13a}$ is hydrogen, optionally substituted alkyl, optionally substituted alkenyl, optionally substituted alkynyl, hydroxy, cyanoalkyl, alkoxy, alkenyloxy, cycloalkyl, aryl, aralkyl, heteroaryl, or heteroaralkyl and $R^{13b}$ is optionally substituted alkyl, optionally substituted alkenyl, optionally substituted alkynyl, cyanoalkyl, alkoxy, alkenyloxy, or cycloalkyl;

$R^{2b}$ is $-X^{2a}-Y^2-X^{2b}-Q^2$ where $X^{2a}$ is a bond, alkylene, alkenylene, or alkynylene where the alkylene, alkenylene, and alkynylene are optionally substituted with one, two, three, four, or five halo or one or two hydroxy;

$Y^2$ is a bond, $-O-$, $-S(O)_{n1}-$ (where n1 is 0, 1, or 2), $-C(O)-$, $-NR^{45}-$, $-NR^{45}C(O)-$, $-NR^{45}C(O)NR^{45}-$, $-NR^{45}C(=NR^{45})NR^{45}-$, $-C(O)NR^{45}-$, $-OC(O)-$, $-C(O)O-$, $-C(O)N(R^{45})N=CR^{74}-$, $-NR^{45}SO_2-$, $-SO_2NR^{45}-$, $-C(R^{74})(=NO)-$, $-C(R^{74})=NNR^{45}-$, $-C(R^{74})=NNR^{45}C(O)-$, $-C(R^{74})=NNR^{45}C(O)NR^{45}-$, $-NR^{45}C(O)O-$, or $-OC(O)NR^{45}$;

where $R^{45}$ is hydrogen, optionally substituted alkyl, optionally substituted alkenyl, optionally substituted alkynyl, hydroxy, alkoxy, or alkenyloxy;

$R^{74}$ is hydrogen, optionally substituted alkyl, optionally substituted alkenyl, or optionally substituted alkynyl; and where alkyl, alkenyl, and alkynyl, either alone or as part of another group within $Y^2$, are independently optionally substituted with one, two, three, four, or five halo;

$X^{2b}$ is a bond; and $Q^2$ is hydrogen, cyano, optionally substituted alkyl, optionally substituted alkenyl, optionally substituted alkynyl, haloalkyl, haloalkenyl, haloalkynyl, aryl, cycloalkyl, heterocycloalkyl, or heteroaryl;

to give a compound of Formula I(e):

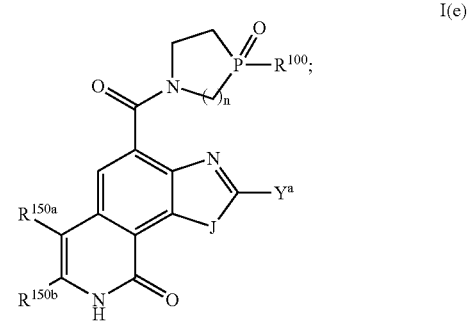

I(e)

or (b) reacting an intermediate of Formula 9:

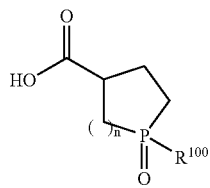

or a salt thereof or an activated acid derivative thereof, where n is 1, 2 or 3 and $R^{100}$ is as defined in (a) with an intermediate of formula I(g):

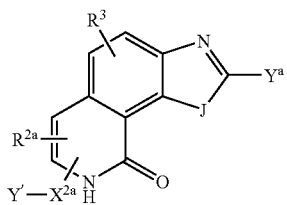

or a salt thereof, where

J is —O—, —S—, or —NR$^5$—; where $R^5$ is hydrogen, hydroxy, alkoxy, alkenyloxy, acyl, optionally substituted alkyl, optionally substituted alkenyl, optionally substituted alkynyl, alkoxycarbonyl, aminocarbonyl, alkylaminocarbonyl, dialkylaminocarbonyl, alkylsulfonyl, alkylaminosulfonyl, or dialkylaminosulfonyl; and where alkyl, alkenyl, alkynyl, and alkylene, either alone or as part of another group within J, are independently optionally substituted with one, two, three, four, or five halo;

$Y^a$ is —NR$^{1a}$R$^{1b}$, —OR$^{1c}$, or —SR$^{1d}$ where $R^{1a}$ is hydrogen, optionally substituted alkyl, optionally substituted alkenyl, optionally substituted alkynyl, hydroxy, alkoxy, alkenyloxy, acyl, —C(O)N(R$^7$)$_2$, -(A$^1$)-C(O)NR$^{8a}$R$^{8b}$, —SO$_2$R$^6$, -(A$^1$)-SO$_2$R$^6$, —SO$_2$N(R$^7$)$_2$, -(A$^1$)-SO$_2$N(R$^7$)$_2$, —C(O)OR$^6$, -(A$^1$)-C(O)OR$^{33}$, cycloalkyl, cycloalkylalkyl, heterocycloalkyl, or heterocycloalkylalkyl;

where each $R^7$ is independently selected from among hydrogen, optionally substituted alkyl, optionally substituted alkenyl, optionally substituted alkynyl, cycloalkyl, cycloalkylalkyl, heterocycloalkyl, and heterocycloalkylalkyl;

$A^1$ is alkylene, alkenylene, or alkynylene;

$R^{8a}$ is substituted alkyl, substituted alkenyl, substituted alkynyl, cycloalkyl, cycloalkylalkyl, heterocycloalkyl, or heterocycloalkylalkyl;

$R^{8b}$ is hydrogen or $R^{8a}$;

$R^6$ is optionally substituted alkyl, cycloalkyl, cycloalkylalkyl, heterocycloalkyl, or heterocycloalkylalkyl;

$R^{33}$ is substituted alkyl, substituted alkenyl, substituted alkynyl, cycloalkyl, cycloalkylalkyl, heterocycloalkyl, or heterocycloalkylalkyl; and where alkyl, alkenyl, alkynyl, and alkylene, either alone or as part of another group within $R^{1a}$, are independently optionally substituted with one, two, three, four, or five halo;

$R^{1b}$ is aryl, aralkyl, cycloalkyl, cycloalkylalkyl, heteroaryl, heteroaralkyl, heterocycloalkyl, or heterocycloalkylalkyl; or $R^{1a}$ and $R^{1b}$ together with the nitrogen to which they are attached form heterocycloalkyl or heteroaryl;

$R^{1c}$ and $R^{1d}$ are independently hydrogen, optionally substituted alkyl, optionally substituted alkenyl, acyl, cycloalkyl, cycloalkylalkyl, heterocycloalkyl, heterocycloalkylalkyl, aryl, aralkyl, heteroaryl, heteroaralkyl, or -(A$^{18}$)-C(O)NR$^{50a}$R$^{50b}$;

$A^{18}$ is alkylene, alkenylene, or alkynylene; and $R^{50a}$ and $R^{50b}$ are independently hydrogen, optionally substituted alkyl, aryl, aralkyl, heteroaryl, heteroaralkyl, cycloalkyl, cycloalkylalkyl, heterocycloalkyl, or heterocycloalkylalkyl); and where alkyl, alkenyl, and alkylene either alone or as part of another group within $R^{1a}$, $R^{1b}$, $R^{1c}$ and $R^{1d}$, are independently optionally substituted with one, two, three, four, or five halo;

$R^{2a}$ is hydrogen, optionally substituted alkyl, optionally substituted alkenyl, optionally substituted alkynyl, hydroxy, alkoxy, alkenyloxy, optionally substituted phenyl, cyano, optionally substituted phenyl, heteroaryl, —NR$^{14a}$R$^{14b}$, -(A$^1$)-NR$^{12a}$R$^{12b}$, —NR$^{13a}$C(O)R$^{13b}$, -(A$^1$)-NR$^{13a}$C(O)R$^{13b}$, —C(O)NR$^{14a}$R$^{14b}$, or -(A$^1$)-C(O)NR$^{12a}$R$^{12b}$; and where alkyl, alkenyl, alkynyl, and alkylene, either alone or as part of another group within $R^{2a}$, are independently optionally substituted with one, two, three, four, or five halo;

$R^{12a}$ is substituted alkyl, substituted alkenyl, substituted alkynyl, hydroxy, cyanoalkyl, alkoxy, or alkenyloxy; and $R^{12b}$ is hydrogen or $R^{12a}$;

$R^{14a}$ and $R^{14b}$ are independently hydrogen, optionally substituted alkyl, optionally substituted alkenyl, optionally substituted alkynyl, hydroxy, cyanoalkyl, alkoxy, or alkenyloxy;

$R^{13a}$ is hydrogen, optionally substituted alkyl, optionally substituted alkenyl, optionally substituted alkynyl, hydroxy, cyanoalkyl, alkoxy, alkenyloxy, cycloalkyl, aryl, aralkyl, heteroaryl, or heteroaralkyl and $R^{13b}$ is optionally substituted alkyl, optionally substituted alkenyl, optionally substituted alkynyl, cyanoalkyl, alkoxy, alkenyloxy, or cycloalkyl;

$R^3$ is —X$^{3a}$—Y$^3$—X$^{3b}$-Q$^4$ where $X^{3a}$ is a bond, alkylene, alkenylene, or alkynylene where alkylene, alkenylene, and alkynylene are independently optionally substituted with one, two, three, four, or five halo or one or two hydroxy, $Y^3$ is —C(O)—, or —NR$^{51}$— where $R^{51}$ is hydrogen, optionally substituted alkyl, optionally substituted alkenyl, optionally substituted alkynyl, cycloalkyl, cycloalkylalkyl, heterocycloalkyl, or heterocycloalkylalkyl and where alkyl, alkenyl, and alkynyl, either alone or as part of another group within $Y^3$, are independently optionally substituted with one, two, three, four, or five halo, $X^{3b}$ is a bond, alkylene, alkenylene, alkynylene, cycloalkylene, or heterocycloalkylene where alkylene, alkenylene, and alkynylene are independently optionally substituted with one, two, three, four, or five halo or one or two hydroxy, and $Q^4$ is Z where Z is —P(=E)($Y^{10a}R^{60a}$)($Y^{10b}R^{60b}$), —P($Y^{10a}R^{60a}$)($Y^{10b}R^{60b}$), —P(=E)($Y^{10e}R^{60a}$)($Z^{10}R^{61}$), or an optionally substituted ring system where one ring member is —P(=E)($R^{100}$)—;

E is oxygen or sulfur;

$Y^{10a}$ and $Y^{10b}$ are independently a single bond, —O—, —S—, or —$NR^{62a}$— where $R^{62a}$ is hydrogen, hydroxy, alkoxy, alkenyloxy, optionally substituted alkyl, optionally substituted alkenyl, or optionally substituted alkynyl;

$R^{60a}$ and $R^{60b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is —O—, —S—, or —$NR^{62}$—;

$R^{60a}$ and $R^{60b}$ are independently optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl when $Y^{10a}$ or $Y^{10b}$, respectively, is a single bond;

$Y^{10e}$ is —O—, —S—, or —$NR^{62a}$—;

$Z^{10}$ is alkylene, alkenylene, alkynylene, —O—, —S—, or —$NR^{62a}$—;

$R^{61}$ is hydrogen, acyl, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl; or $R^{61}$ is —P(=E)($Y^{10a}R^{60a}$)($Y^{10b}R^{60}$b);

$R^{100}$ is a single bond from the phosphorous atom to $X^{1b}$, or $R^{100}$ is halo, optionally substituted alkyl, optionally substituted alkenyl, optionally substituted alkynyl, optionally substituted phenyl, optionally substituted phenylalkyl, cycloalkyl, cycloalkylalkyl, heterocycloalkyl, heterocycloalkylalkyl, heteroaryl, heteroaralkyl, —$OR^{101}$, or —$NR^{102a}R^{102b}$; and where the alkyl, alkenyl, and alkynyl within $R^{100}$, either alone or as part of another substituent, are independently optionally substituted with one, two, three, four, or five halo;

$R^{101}$ is hydrogen, optionally substituted alkyl, optionally substituted alkenyl, or optionally substituted alkynyl;

$R^{102a}$ and $R^{102b}$ are independently hydrogen, optionally substituted alkyl, optionally substituted alkenyl, optionally substituted alkynyl, aryl, aralkyl, heteroaryl, heteroaralkyl, cycloalkyl, cycloalkylalkyl, heterocycloalkyl, or heterocycloalkylalkyl;

$X^{2a}$ is a bond, alkylene, alkenylene, or alkynylene where the alkylene, alkenylene, and alkynylene are optionally substituted with one, two, three, four, or five halo or one or two hydroxy;

and Y' is —OH, —$NHR^{18}$, or —C(O)$NHR^{22}$ where $R^{18}$ and $R^{22}$ are independently hydrogen, optionally substituted alkyl, optionally substituted alkenyl, optionally substituted alkynyl, hydroxy, alkoxy, or alkenyloxy;

to give a compound of Formula I(f):

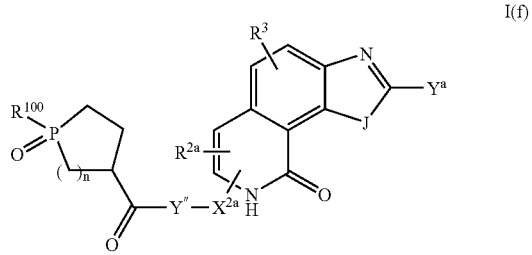

I(f)

where Y" is —O—, $NR^{18}$—, or $NR^{22}$—;

and (a) optionally separating individual isomers of the compounds;

(b) optionally forming an acid addition salt of the product formed in Step (a) or (b) above;

(c) optionally forming a free base of the product formed in Step (a) or (b) above;

(d) optionally modifying any of the J, $Y^a$, and groups in the product formed in Step (a), (b), (c), (d), or (e) above.

Preparation of Compounds

Compounds provided herein, which inhibit the activity of tyrosine kinases, such as Bruton's tyrosine kinase (Btk), may be synthesized using standard synthetic techniques known to those of skill in the art or using methods known in the art in combination with methods described herein. As a further guide the following synthetic methods may also be utilized.

The reactions can be employed in a linear sequence to provide the compounds described herein or they may be used to synthesize fragments which are subsequently joined by the methods described herein and/or known in the art.

Use of Protecting Groups

The term "protecting group" refers to chemical moieties that block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester derivatives as exemplified herein, or they may be blocked with oxidatively-removable protective groups such as 2,4-dimethoxybenzyl, while co-existing amino groups may be blocked with fluoride labile silyl carbamates. In one embodiment, a compound containing both a carboxylic acid reactive moiety and a hydroxy reactive moiety may have one of the reactive moieties blocked while the other reactive moiety is not blocked.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

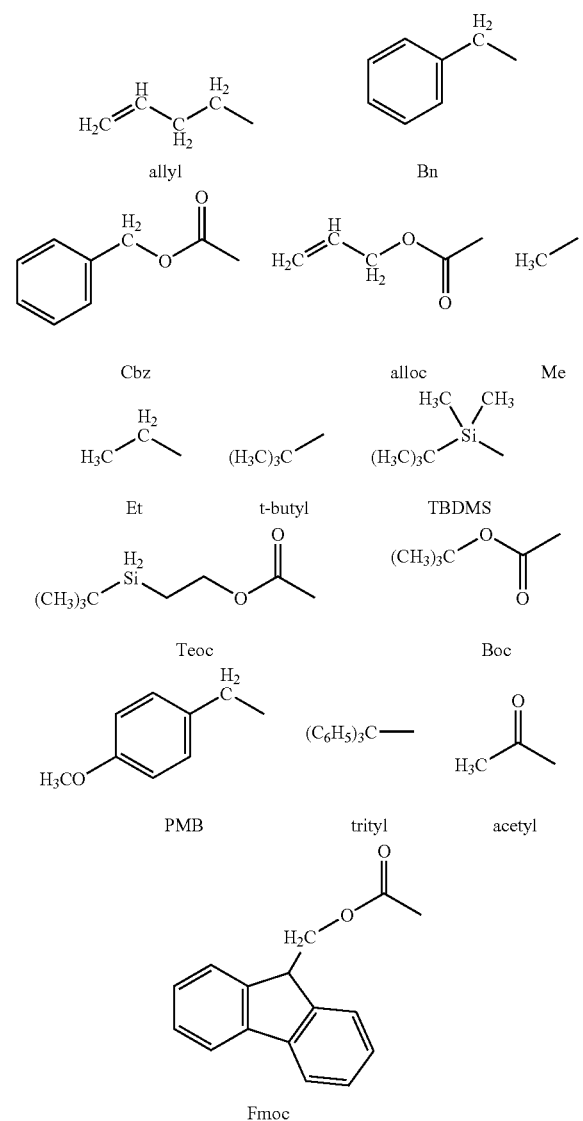

Other protecting groups are described in Greene and Wuts, Protective Groups in Organic Synthesis, 3rd Ed., John Wiley & Sons, New York, N.Y., 1999, which is incorporated herein by reference in its entirety.

Synthesis of Compounds

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

Described herein are compounds that inhibit the activity of tyrosine kinase(s), such as Btk, and processes for their preparation. Also described herein are pharmaceutically acceptable salts, pharmaceutically acceptable solvates, pharmaceutically active metabolites and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/25238, U.S. Pat. No. 6,506,769, U.S. Pat. No. 6,770,639; Snow et al. *Tetrahedron Letters*, 43 (2002) 7553-7556; Goldberg et al. *J. Med. Chem.* 2003, 46, 1337-1349; Snow et al. *J. Med. Chem.* 2002, 45, 3394-3405; and *J. Heterocyclic Chem.*, 1970, 7, 615. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

The products of the reactions may be isolated and purified, if desired, using conventional techniques, including, but not limited to, filtration, distillation, crystallization, chromatography and the like. Such materials may be characterized using conventional means, including obtaining physical properties and spectral data.

Compounds described herein may be prepared using the synthetic methods described herein as a single isomer or a mixture of isomers.

Scheme I.

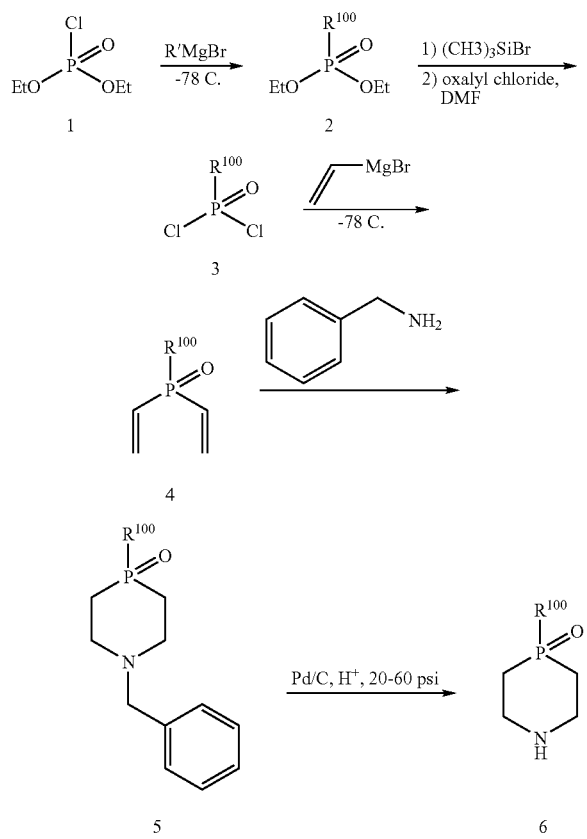

Scheme II.

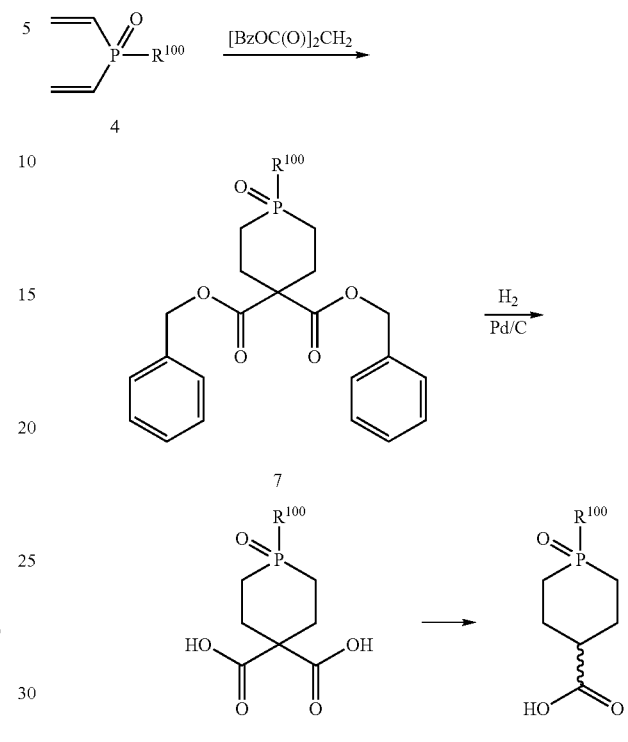

Ring systems where one ring member is a phosphine or phosphine oxide can be prepared by following the procedure outlined in Scheme I. Treatment of a halodialkoxyphosphine oxide, such as, for example, chlorodiethoxyphosphine oxide (structure 1), with an alkyl metal salt, such as for example, a grignard reagent, provide compounds of structure 2. Treatment of phosphine oxides of structure 2 with bromotrimethylsilane, followed by oxalyl chloride, provides halo phosphine oxides of structure 3. Compounds of structure 3 are also commercially available.

Compounds of structure 3 can also be prepared by reacting P(OR$^a$)$_2$(OR$^b$) where R$^a$ is methyl or ethyl and R$^b$ is hydrogen, methyl or ethyl, e.g. trimethyl phosphite or diethyl phosphite, with R$^{100}$X, where X is halogen. Where R$^{100}$ is an optionally substituted aryl or heteroaryl, the reaction is carried out in the presence of a metal catalyst, such as, for example, a palladium catalyst, such as, for example, tetrakis (triphenylphosphine)-palladium, in the presence of a base, such as, for example, triethylamine.

Compounds of structure 3 are then treated with a vinyl metal salt, such as, for example, vinylmagnesium bromide, to give compounds of structure 4. Divinyl phosphine oxides of structure 4 are treated with a primary amine, such as, for example, benzylamine or p-methoxybenzylamine, to provide the cyclic amines of structure 5. Removal of the protecting group on the nitrogen, such as, by catalytic hydrogenation, provides cyclic amines of structure 6.

Scheme II depicts the synthesis of cyclic phosphine oxides such as structure 9. Reacting divinyl phosphine oxides of structure 4 with a malonate, such as, for example, dibenzylmalonate, in the presence of a base, such as, for example, potassium carbonate, provides heterocycloalkyls of structure 7. Compounds of structure 7 are then deprotected under reducing conditions, such as, by treatment with hydrogen in the presence of a catalyst, such as, for example, palladium on carbon in a suitable solvent such as, for example, ethanol, to yield the dicarboxylic acids of structure 8. Decarboxylation of dicarboxylic acids of structure 8 provides carboxylic acids of structure 9. In one embodiment, 8 is decarboxylated under microwave conditions, such as, for example, at a temperature of over about 200° C. In another embodiment, 8 is decarboxylated under acidic conditions, such as, for example, by heating a solution of 8 in the presence of 1N HCl. Other methods of decarboxylating beta ketoacids are known in the art.

Scheme III.

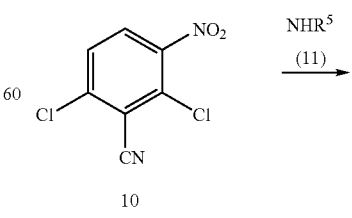

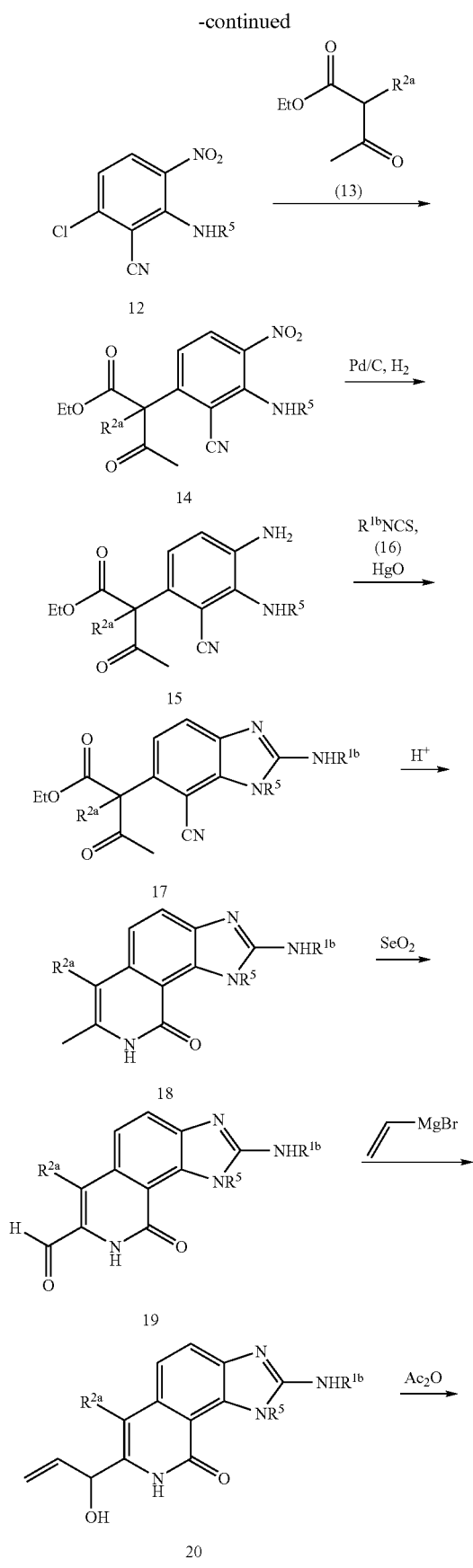
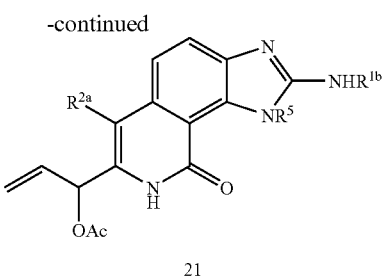

As shown in Scheme III, the synthesis of allylic acetates of structure 21 begins by performing a selective $S_NAr$ reaction with 2,6-dichloro-3-nitrobenzonitrile (10). Reaction of 10 with an amine, such as, for example, ammonia or an alkylamine, such as, for example, methylamine, provides structure 12. A subsequent $S_NAr$ reaction of structure 12 with an alkyl acetoacetate derivative provides structure 14, which contains the necessary number of atoms to form the isoquinoline core. Reduction of the nitro moiety nitroaromatics of structure 14, is followed by formation of the benzimidazole by reacting diamines of structure 15 with an isothiocyante, such as for example, an aryl isothiocyanate, in the presence of mercuric oxide (HgO) in refluxing THF. Alternatively, diamines of structure 15 are treated with a isothiocyante and the intermediate thiourea is treated with an activating agent, such as, for example, 1,3-dicyclohexylcarbodiimide (DCC), to provide benzimidazoles of structure 17.

The isoquinolone moiety is then formed by treatment of benzimidazoles of structure 17 with acid to polycycles of structure 18. The formation of polycycles of structure 18 involves hydrolysis of the nitrile followed by condensation with the ketone. Depending on the reaction conditions used, isoquinolone formation may or may not involve decarboxylation of the ester moiety. For example, under mild acidic reaction conditions, such as in the treatment of benzimidazoles of structure 17 with sulfuric acid at room temperature, 18 is obtained, where $R^{2a}$ is —C(O)OEt. In other embodiments, treatment of benzimidazoles of structure 17 with sulfuric acid, water and acetic acid at 100° C., provides 18, which involves hydrolysis of the nitrile, condensation with the ketone, and decarboxylation of the ester moiety in one, step.

Treatment of structure 18 with selenium dioxide in an ethereal solvent, such as, for example, dioxane, results in selective oxidation at the C-7 methyl to provide aldehydes of structure 19. Aldehydes of structure 19 are then treated with a vinyl metal salt, such as, for example, vinylmagnesium bromide to provide 20. Treatment of 20 with an activated carboxylic acid, such as, for example, acetic anhydride, provides allyllic acetates of structure 21.

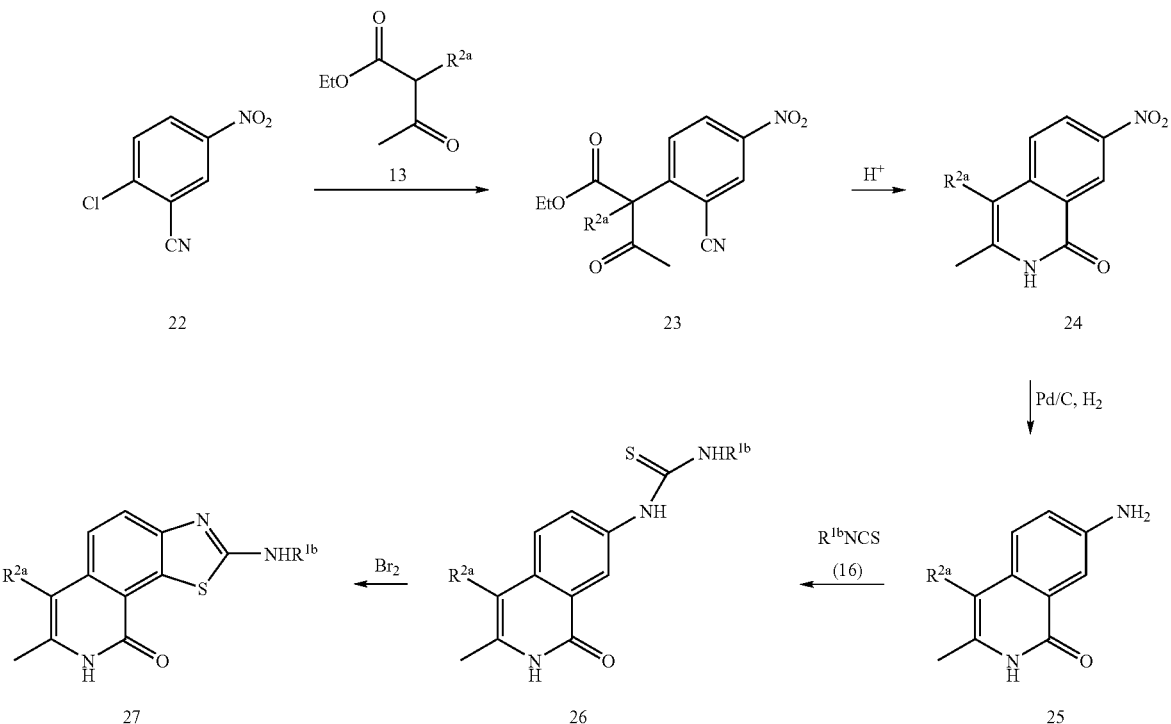

Scheme IV depicts the synthesis of benzothiazoles. A S$_N$Ar reaction of 2-chloro-5-nitrobenzonitrile (22) with an alkyl acetoacetate derivative provides structure 23. Isoquinolones of structure 24 are formed by treatment of structure 23 with acid. Reduction of the nitro moiety of structure 24 is followed by treatment of amines of structure 25 with an isothiocyante to provide a thiourea intermediate (26). Reaction of the thiourea intermediate of structure 26 under cyclizing conditions, such as in the presence of bromine in a suitable solvent, such as, for example, chloroform, provides the benzothiazole. Further fictionalization and manipulation of the benzothiazole is then carried out as described herein or known in the art.

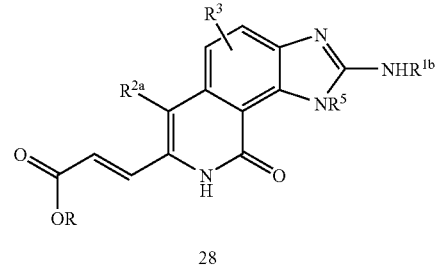

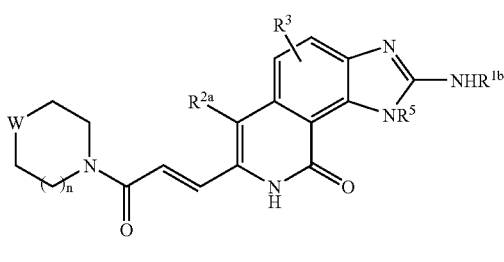

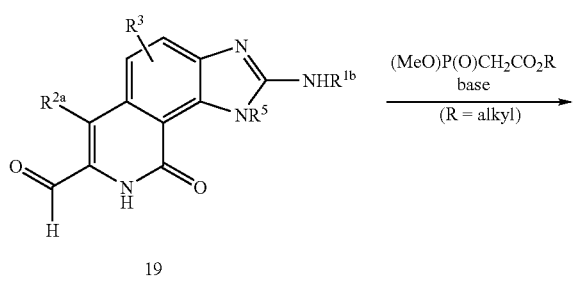

Scheme V shows derivatization of aldehydes of structure 19 using the Homer-Wadsworth-Emmons olefination reaction. Treatment of aldehydes of structure 19 with trimethyl phosphonoacetate in the presence of a base, such as, for example, lithium hydroxide, provides α, β-unsaturated esters of structure 28. Hydrolysis of structure 28 is then followed by reaction with an amine in the presence of a coupling agent, such as, for example, benzotriazole-1-yloxytrispyrrolidino-phosphonium hexafluorophosphate (PyBOP®), O-benzotria-zol-1-yl-N,N,N',N'-tetramethyl-uronium hexafluorophos-phate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), to provide amides of structure 29.

presence of a metal catalyst, such as for example, a palladium catalyst, followed by a Staudinger reaction to provide ally-lamines of structure 31. Allylamines of structure 31 can be coupled with a variety of carboxylic acids to provide amides. Sulfonamides and urea compounds can also be prepared using allylamines of structure 31.

In some embodiments, the alkene portion of the allylic moiety may be hydrogenated to provide the analogous alkyl compounds.

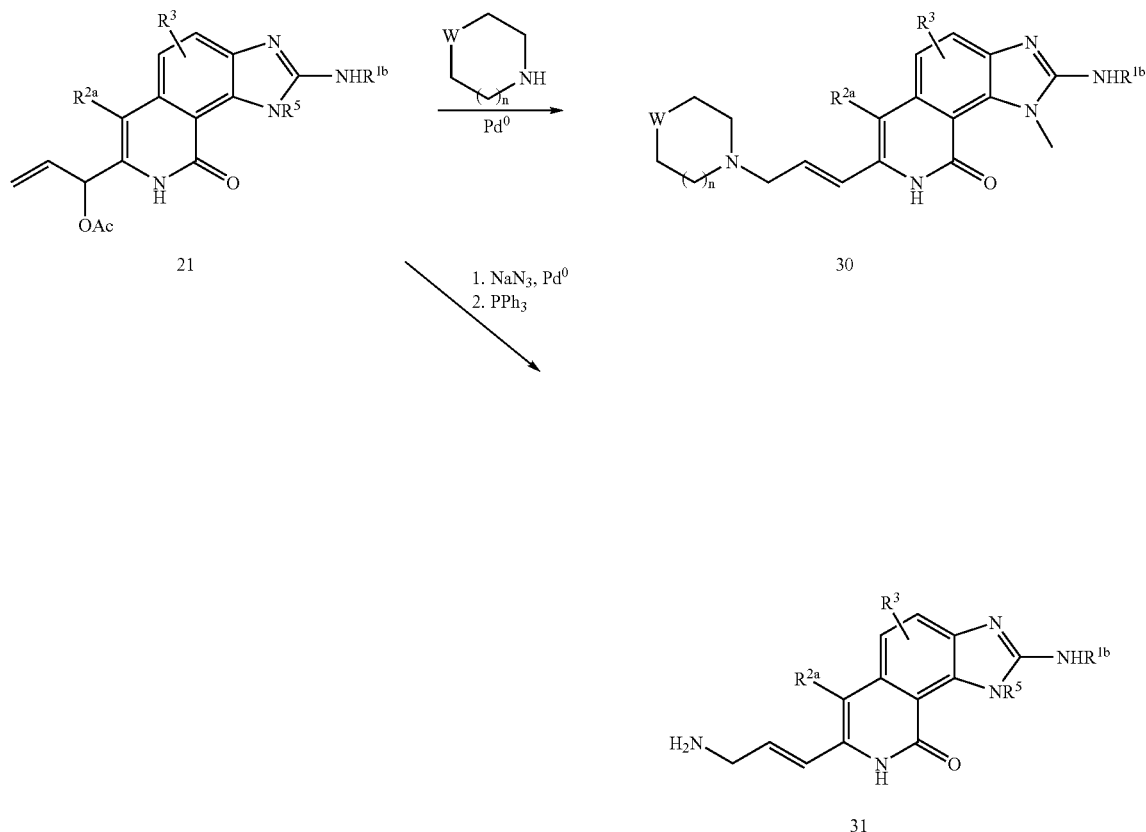

Scheme VI shows the synthesis of allylic amines through allylic transposition of allylic acetates of structure 21 with amine nucleophiles. In some embodiments, allylic acetates of structure 21 are treated with a nucleophile, such as, for example, an amine, in the presence of a metal catalyst, such as for example, a palladium catalyst, to provide allylic amines of structure 30. Suitable palladium catalysts include, but are not limited to, tris(dibenzylacetone)dipalladium (Pd$_2$(dba)$_3$), palladium dichloride, bis(acetonitrile)dichloropalladium, and tetrakistriphenylphosphine palladium. Suitable ligands for the palladium catalyst include, but are not limited to triphenylphosphine.

In other embodiments, allylic acetates of structure 21 are treated with azide, such as, for example, sodium azide, in the

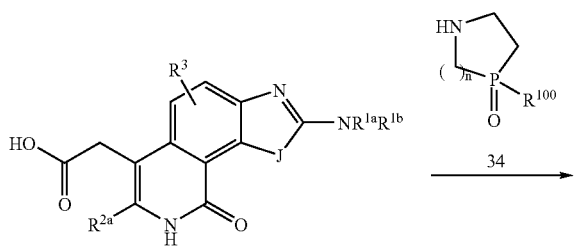

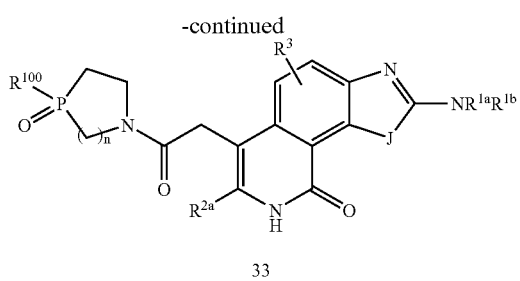

33

As shown in Scheme VII, amides of structure 33 can be prepared by reacting intermediates of structure 32 with an amines of structure 34. The reaction can be carried out in inert organic solvents such as methylene chloride, acetonitrile, N,N-dimethylformamide, ethereal solvents such as tetrahydrofuran, dioxane, and the like. The reaction is typically carried out in the presence of a suitable coupling agent, e.g., benzotriazole-1-yloxytrispyrrolidino-phosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), and in the presence of a base (typically 3 equivalents) such as N,N-diisopropylethylamine, triethylamine, N-methylmorpholine, and the like, and optionally in the presence of 1-hydroxy-benzotriazole (HOBT).

As shown in Scheme VIII, diamines of structure 15 can be reated with bromine in a suitable solvent, such as, for example, chloroform at ambient temperature to provide bromo diamines of structure 35. As described above, diamines of structure 35 is then converted to the benzimidazoles of structure 36. Cross-coupling chemistry can be used to introduce a variety of groups in the place of bromine. In one embodiment, Stille reaction conditions are used, which involves the reaction of bromo benzimidazoles of structure 36 with an alkyl tributyltin compound, in the presence of a palladium catalyst, such as $(PPh_3)_2PdCl_2$. Solvents such as 1-methyl-2-pyrrolidinone (NMP) are typically used in the Stille reaction. Alternatively, Sonagashira reaction conditions can be used, which involves the reaction of bromo bromo benzimidazoles of structure 36 with a terminal alkyne in the presence of a palladium catalyst, such as $(PPh_3)_2PdCl_1$, and CuI, and a suitable base, such as triethylamine in a solvent such as THF. Other cross coupling reactions involving aryl halides are known in the art, and involve, but are not limited to, Heck reactions, Suzuki reactions, Negishi reactions, Buchwald-Hartwig cross coupling reaction, Kumada reactions, and Hiyama cross-coupling reactions.

Alternatively, bromo benzimidazole of structure 36 is treated with acid to form the isoquinolone core. Treatment of structure 38 with an amine under an atmosphere of carbon monoxide (CO) in the presence of a palladium catalyst, such as, for example, $Pd(PPh_3)_4$, $PdCl_2(Ph_3P)_2$, or $Pd(OAc)_2$ in the presence of triphenylphosphine, and a base, such as, tributylamine or N,N-diisopropylethylamine, and optionally a suit-

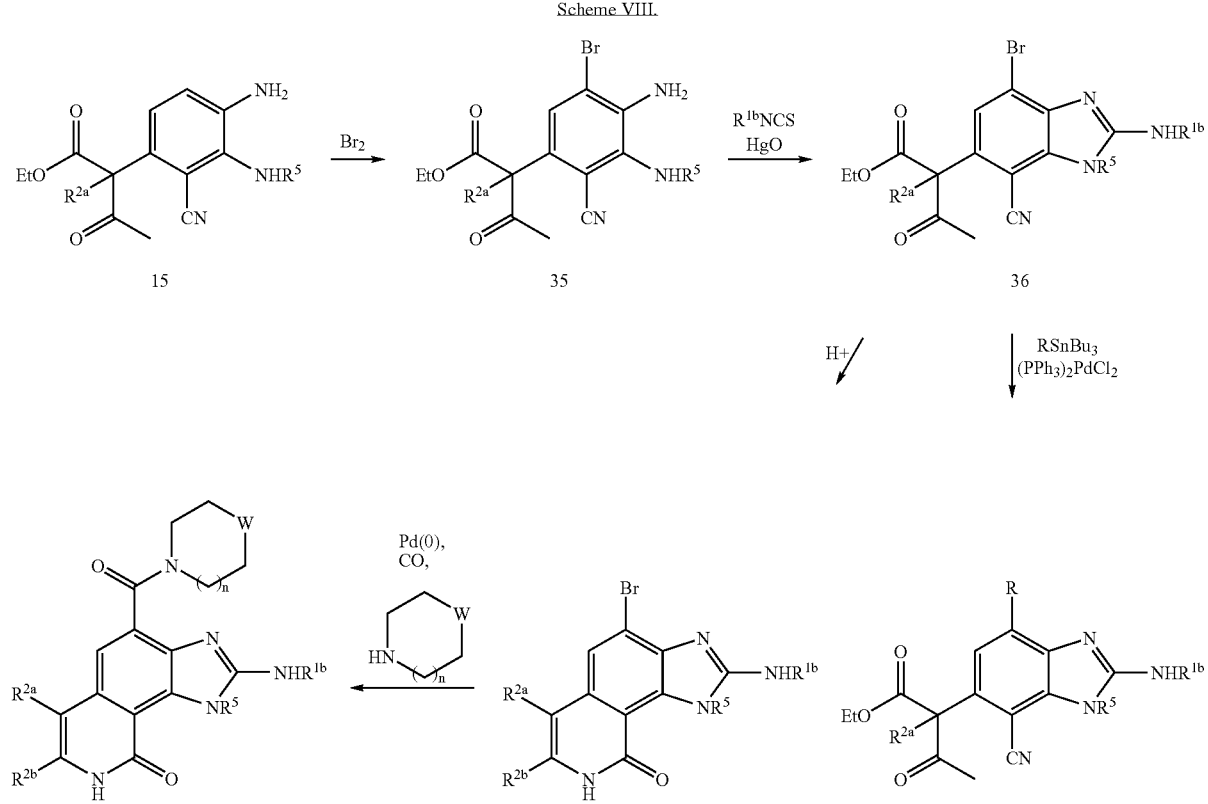

able co-solvent such N,N-dimethylacetamide (DMA), N,N-dimethylformamide (DMF), tetrahydrofuran (THF), or dioxane, provides compounds of structure 39.

Scheme IX.

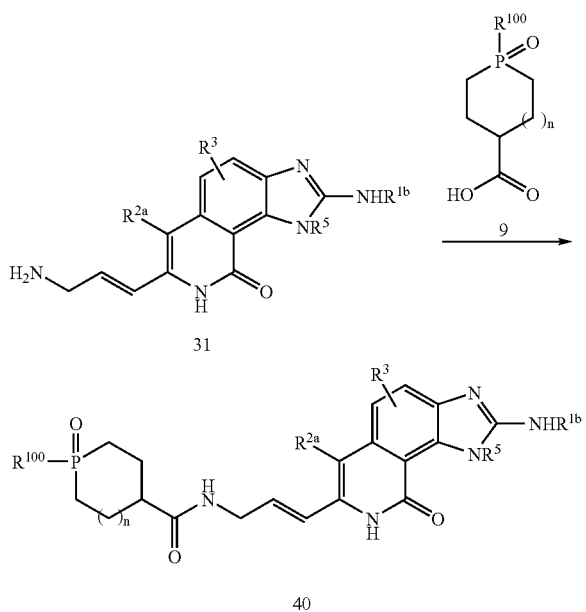

Scheme IX shows a strategy for the synthesis of amides of structure 40. Amides of structure 40 can be prepared by reacting carboxylic acid of structure 9 with amine of structure 31. The reaction is performed in the presence of a coupling agent, such as, for example, benzotriazole-1-yloxytrispyrrolidino-phosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), and in the presence of a base (typically 3 equivalents) such as N,N-diisopropylethylamine, triethylamine, N-methylmorpholine, and the like, and optionally in the presence of 1-hydroxy-benzotriazole (HOBT). Alternatively, carboxylic acid of structure 9 is first converted to an acid chloride by treatment with thionyl chloride or oxalyl chloride and then coupled with amine of structure 31.

Using the synthetic methods described herein, as well as those known in the art, tyrosine kinase inhibitors as disclosed herein are obtained in good yields and purity. The compounds prepared by the methods disclosed herein are purified by conventional means known in the art, such as, for example, filtration, recrystallization, chromatography, distillation, and combinations thereof.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Pharmaceutical Composition/Formulation

Compounds disclosed herein have a structure selected from among Formula (Ia), Formula (Ib), Formula (Ic), Formula (II), Formula (III), Formula (IIIa), Formula (IIIb), Formula (IIIc), Formula (IV), Formula (V), and Formula (VI). It is understood that when reference is made to compounds described herein, it is meant to include compounds of Formula (Ia), Formula (Ib), Formula (Ic), Formula (II), Formula (III), Formula (IIIa), Formula (IIIb), Formula (IIIc), Formula (IV), Formula (V), and Formula (VI), unless otherwise indicated.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

Provided herein are pharmaceutical compositions that include a compound described herein and a pharmaceutically acceptable diluent(s), excipient(s), or carrier(s). In addition, the compounds described herein can be administered as pharmaceutical compositions in which compounds described herein are mixed with other active ingredients, as in combination therapy. In some embodiments, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

In certain embodiments, compositions may also include one or more pH adjusting agents or buffering agents, including acids such as, but not limited to, acetic, boric, citric, lactic, phosphoric and hydrochloric acids; bases such as, but not limited to, sodium hydroxide, sodium phosphate, sodium borate, sodium citrate, sodium acetate, sodium lactate and tris-hydroxymethylaminomethane; and buffers such as, but not limited to, citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

A pharmaceutical composition, as used herein, refers to a mixture of a compound described herein with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

Certain Pharmaceutical Terminology

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "acceptable" with respect to a formulation, composition or ingredient, as used herein, means having no persistent detrimental effect on the general health of the subject being treated.

As used herein, the term "selective inhibitor compound" refers to a compound that selectively inhibits a specific function/activity of one or more target proteins.

As used herein, the term "selectively inhibits" refers to the ability of a selective inhibitor compound to inhibit a specific function/activity of a target protein (e.g., the phosphotransferase activity of a kinase) with greater potency than the activity of a non-target protein. In certain embodiments, selectively inhibiting refers to inhibiting a target protein activity with a selective inhibitor that has a $IC_{50}$ that is at least 10, 50, 100, 250, 500, 1000 or more times lower than for that of a non-target protein activity.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "selective modulator" refers to a compound that selectively modulates a target activity.

As used herein, the $IC_{50}$ refers to an amount, concentration or dosage of a particular test compound that achieves a 50% inhibition of a maximal response, such as inhibition of tyrosine kinase activity, such as, for example Btk activity, in an assay that measures such response.

As used herein, $IC_{50}$ refers to a dosage, concentration or amount of a particular test compound that elicits a dose-dependent response at 50% of maximal expression of a particular response that is induced, provoked or potentiated by the particular test compound.

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound administered, age, weight, general condition of the subject, the condition being treated, the severity of the condition being treated, and the judgment of the prescribing physician.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, a compound is metabolized to pharmacologically active metabolites.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach,* Oxford University Press, New York, pages 388-392; Silverman (1992), The Organic Chermistry of Drug Design and Drug Action, Academic Press, Inc., San Diego, pages 352-401).

By "pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. Pharmaceutically acceptable salts may be obtained by reacting a compound described herein, with acids such as: hydrochloric acid, hydrobromic acid, sulfuric acid, nitric acid, phosphoric acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also may be obtained by reacting a compound described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods known in the art.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Bioavailability" refers to the percentage of the weight of compounds disclosed herein dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which compounds disclosed herein are absorbed into the general circulation when the pharmaceutical composition is taken orally as compared to intravenous injection.

"Blood plasma concentration" refers to the concentration of compounds provided herein in the plasma component of blood of a subject. It is understood that the plasma concentration of compounds provided herein may vary significantly between subjects, due to variability with respect to metabolism and/or possible interactions with other therapeutic agents. In accordance with one embodiment disclosed herein, the blood plasma concentration of the compounds provided herein may vary from subject to subject. Likewise, values such as maximum plasma concentration ($C_{max}$) or time to reach maximum plasma concentration ($T_{max}$), or total area under the plasma concentration time curve (AUC$_{(0-\infty)}$) may vary from subject to subject. Due to this variability, the amount necessary to constitute "a therapeutically effective amount" of a compound provided herein may vary from subject to subject.

"Carrier materials" include any commonly used excipients in pharmaceutics and should be selected on the basis of compatibility with compounds disclosed herein and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy,* Nineteenth Ed (Easton, Pa.: Mack Publishing Company, 1995); Hoover, John E., *Remington's Pharmaceutical Sciences,* Mack Publishing Co., Easton, Pa. 1975; Liberman, H. A. and Lachman, L., Eds., *Pharmaceutical Dosage Forms,* Marcel Decker, New York, N.Y., 1980; and *Pharmaceutical Dosage Forms* and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, manmitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per ml, dl, or l of blood serum, absorbed into the bloodstream after administration. As used herein, measurable plasma concentrations are typically measured in ng/ml or μg/ml.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xaiithans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound provided herein, can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the present invention may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound provided herein, with one or more pharmaceutical excipients to form a bulk blend composition. When referring to these bulk blend compositions as homogeneous, it is meant that the particles of the compound provided herein, are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound provided herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound provided herein. In one embodiment, some or all of the particles of the compound provided herein are coated. In another embodiment, some or all of the particles of the compound provided herein are microencapsulated. In still another embodiment, the particles of the compound provided herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound disclosed herein from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and ricrocellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10φ), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the present invention. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compound disclosed herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound disclosed herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds disclosed herein, which sufficiently isolate the compound disclosed herein from other non-compatible excipients. Materials compatible with compounds disclosed herein are those that delay the release of the compounds disclosed herein in vivo.

Exemplary microencapsulation materials useful for delaying the release of the formulations including compounds disclosed herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds disclosed herein may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds disclosed herein are microencapsulated prior to being formulated into one of the above forms. In still another embodiment, some or most of the particles are coated prior to being further formulated by using standard coating procedures, such as those described in *Remington's Pharmaceutical Sciences*, 20th Edition (2000).

In other embodiments, the solid dosage formulations of the compounds disclosed herein are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound disclosed herein may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound disclosed herein, are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

The pharmaceutical solid oral dosage forms, which include a compound disclosed herein, can be further formulated to provide a controlled release of the compound disclosed herein. Controlled release refers to the release of the compound disclosed herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. In some embodiments the polymers for use in the present invention are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., camuba wax or PEG) may be added to the coatings besides plasticizers to solubilize or disperse the coating material, and to improve coating performance and the coated product.

In other embodiments, the formulations described herein, which include a compound disclosed herein, are delivered using a pulsatile dosage form. A pulsatile dosage form is capable of providing one or more immediate release pulses at predetermined time points after a controlled lag time or at specific sites. Pulsatile dosage forms including the formulations described herein, which include a compound disclosed herein, may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form including at least two groups of particles, (i.e. multiparticulate) each containing the formulation described herein. The first group of particles provides a substantially immediate dose of the compound disclosed herein upon ingestion by a mammal. The first group of particles can be either uncoated or include a coating and/or sealant. The second group of particles includes coated particles, which includes from about 2% to about 75%, preferably from about 2.5% to about 70%, and more preferably from about 40% to about 70%, by weight of the total dose of the compound disclosed herein in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound disclosed herein.

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compounds disclosed herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition to the particles of compound disclosed herein, the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than I minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116, 817 and 6,391,452, each of which is specifically incorporated by reference. Formulations that include a compound provided herein, which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds disclosed herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations that include compounds disclosed herein may be administered using a variety of formulations known in the art. For example, such formulations include, but are not limited to, U.S. Pat. Nos. 4,229,447, 4,596,795, 4,755, 386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound disclosed herein is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound disclosed herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiment, the transdermal formulations described herein include at least three components: (1) a formulation of a compound disclosed herein; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds disclosed herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound disclosed herein, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acidibutyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Methods of Dosing and Treatment Regimens

The compounds described herein can be used in the preparation of medicaments for the inhibition of tyrosine kinase activity, such as Btk activity, or for the treatment of diseases or conditions that would benefit, at least in part, from inhibition of Btk activity. In addition, a method for treating any of the diseases or conditions described herein in a subject in need of such treatment, involves administration of pharmaceutical compositions containing at least one compound disclosed herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.01 to 2.5 mg/kg per body weight. An indicated daily dosage in the larger mammal, including, but not limited to, humans, is in the range from about 0.5 mg to about 300 mg, conveniently administered in divided doses, including, but not limited to, up to four times a day or in extended release form. Suitable unit dosage forms for oral administration include from about 1 to 200 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The tyrosine inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one tyrosine kinase inhibitor compound described herein in combination with another therapeutic agent. By way of example only, if one of the side effects experienced by a patient upon receiving one of the tyrosine kinase inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula Ia, Ib, IIa, or IIb described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of Brtuon's tyrosine kinase activity or in which Bruton's tyrosine kinase activity is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally include an identifying description or label or instructions relating to its use in the methods described herein.

A kit may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Exemplary Therapeutic Agents for Use in Combination with a Tyrosine Kinase Inhibitor Compound Agents for Treating Autoimmune Diseases, Inflammatory Diseases, or Allergy Diseases Where the subject is suffering from or at risk of suffering from an autoimmune disease, an inflammatory disease, or an allergy disease, an tyrosine kinase inhibitor compound can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Anti-Cancer Agents

Where the subject is suffering from or at risk of suffering from a B-cell proliferative disorder (e.g., plasma cell myeloma), the subjected can be treated with a tyrosine kinase inhibitor compound in any combination with one or more other anti-cancer agents. In preferred embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is an anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds of the invention.

Further examples of anti-cancer agents for use in combination with a tyrosine kinase inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002.

Other anti-cancer agents that can be employed in combination with a tyrosine kinase inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutarnide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a tyrosine kinase inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermiine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mnitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfm; vinorelbine; vinxaltine; vitaxin; vorozole; zanoterone; zeniplatin; zilascorb; and zinostatin stimalamer.

Yet other anticancer agents that can be employed in combination with a tyrosine kinase inhibitor compound include alkylating agents, antimetabolites, natural products, or hormones, e.g., nitrogen mustards (e.g., mechloroetharnirne, cyclophosphamide, chlorambucil, etc.), alkyl sulfonates (e.g., busurfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a tyrosine kinase inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a tyrosine kinase inhibitor compound include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a tyrosine kinase inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide). Examples of anti-cancer agents which act by arresting cells in the G2-M phases due to stabilized microtubules and which can be used in combination with a tyrosine kinase inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B ), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia, LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamnide A, A-293620 (Abbott), NPI-2350 (Nereus), Taccalonolide A, TUB-245 (Aventis), A-259754 (Abbott), Diozostatin, (-)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Agents for Treating Thromboembolic Disorders

Where the subject is suffering from or at risk of suffering from a thromboembolic disorder (e.g., stroke), the subject can be treated with a tyrosine kinase inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, compounds provided herein may be administered in combination with one or more compound(s) selected from azathioprine, plaquenil, prednisone, sulfasalazine, methotrexate, Arava, Rermicade, and Enbrel.

In other embodiments, compounds provided herein may be administered in combination with one or more compound(s) selected from an estrogen receptor modulator, an androgen receptor modulator, retinoid receptor modulator, a cytotoxic agent, another antiproliferative agent, a prenyl-protein transferase inhibitor, an HMG-CoA reductase inhibitor, an HIV protease inhibitor, a reverse transcriptase inhibitor, and an angiogenesis inhibitor.

In yet other embodiments, compounds provided herein may be administered in combination with one or more chemotherapeutic compound(s) selected from among Taxol®, Taxotere®, epothilone A, epothilone B, desoxyepothilone A, desoxyepothilone B or their derivatives; epidophyllotoxin; procarbazine; mitoxantrone; the mitomycins, discodermolide, podophyllotoxins, doxorubicin, carminomycin, daunorubicin, aminopterin, methotrexate, methopterin, dichloromethotrexate, mitomycin C, porfiromycin, Herceptin®, Rituxan®, 5-fluorouracil, 6-mercaptopurine, gemcitabine, cytosine arabinoside, colchicines, etoposide, etoposide phosphate, teniposide, melphalan, vinblastine, vincristine, vinorelbein, leurosidine, vindesine, leurosine, paclitaxel, estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, interleukins, capecitabine, and gefitinib.

In yet other embodiments, compounds provided herein may be administered in combination with a β-2 adrenoreceptor agonist, corticosteroid, leukotriene antagonist, phosphodiesterase 4 inhibitor, and/or antihistamine. In further embodiments, compounds provided herein may be administered in combination with one or more compound(s) selected from salmeterol, fluticasone, budesonide, montelukast, levalbuterol, and roflumilast.

EXAMPLES

The person skilled in the art may further appreciate various aspects and advantages of the present disclosure upon review of the following illustrative and non-limiting examples:

Synthesis of Compounds

Intermediate 1: 4-Methyl-[1,4]azaphosphinane 4-oxide hydrochloride

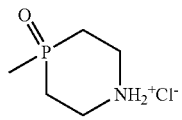

Step 1

A solution of methylphosphonic dichloride (9.92 g, 74.6 mmol) in THF (75 mL) at −78° C. was treated with vinylmagnesium bromide in THF (175 mL, 1.0 M), which was added over 4 hours via an addition funnel. The solution was warmed to 0° C. and quenched with saturated. NH$_4$Cl. The solvents were evaporated under reduced pressure and the residue was triturated with 1:1 THF/ethyl acetate several times to extract the divinyl methyl phosphine oxide product, which was used directly without further purification.

Step 2

A solution of methyl divinyl phosphine oxide (10.73 g, 92.4 mmol) and benzylamine (11.6 mL, 106.3 mmol) in 1:1 THF/water (250 mL) was heated at reflux for 16 hours. The solvents were removed under reduced pressure. The residue was crystallized from CH$_2$Cl$_2$/ether to give 1-benzyl-4-methyl-[1,4]azaphosphinane 4-oxide as a white solid (13.24 g, 64%). $^1$H NMR (400 MHz, DMSO) δ 7.13-3.37 (5H, m); 3.6 (2H, s); 2.81 (2H, m); 2.59 (2H, m); 1.7-1.9 (4H, m); 1.42 (3H, d, JH-C-P=13.6 Hz). $^{31}$P NMR δ32 ppm.

Step 3

1-Benzyl-4-methyl-[1,4]azaphosphinane 4-oxide was dissolved in ethanol (100 mL). 1 M HCl (100 mL) was added, along with palladium on carbon (10%, 2.6 g). The mixture was hydrogenated on a Parr shaker for 4 hours at 50 psi. The mixture was filtered through Celite and all solvents were removed under reduced pressure. The product was triturated in hot ethanol (50 mL) and cooled, and the solution was diluted with ether (300 mL). The white crystalline solid was filtered, washed with ether (2×50 mL), hexane (2×50 mL), and dried in vacuo. 4-methyl-[1,4]azaphosphinane 4-oxide hydrochloride was obtained as a white crystalline solid (9.46 g, 94%). $^1$H NMR (400 MHz, DMSO) δ 3.07 (m, 2H); 2.68 (m, 2H); 1.78 (m, 2H); 1.61 (m, 2H), 1.39 (3H, d, JH-C-P=13.6 Hz.); $^{31}$P NMR: δ 29 ppm; ESMS (m/z): (M+1)$^+$ found, 134.

Intermediate 2: 4-Methyl-[1,4]azaphosphinane 4-oxide

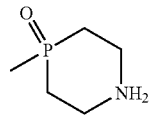

Step 1

To a scintillation vial was added 4-methyl-[1,4]azaphosphinane 4-oxide hydrochloride (0.2 g, 1.18 mmol), carbonate resin (1.0 g, MP-carbonate, Argonaut, 2.5-3 mmol/g, obtained from Argonaut Technologies, Inc., 220 Saginaw Drive, Redwood City, Calif. 94063, USA), methanol (2 mL), and THF (2 mL). The mixture was stirred at room temperature for 1 hour, then filtered and concentrated in vacuo.

Intermediate 3: 4-Phenyl-[1,4]azaphosphinane 4-oxide hydrochloride

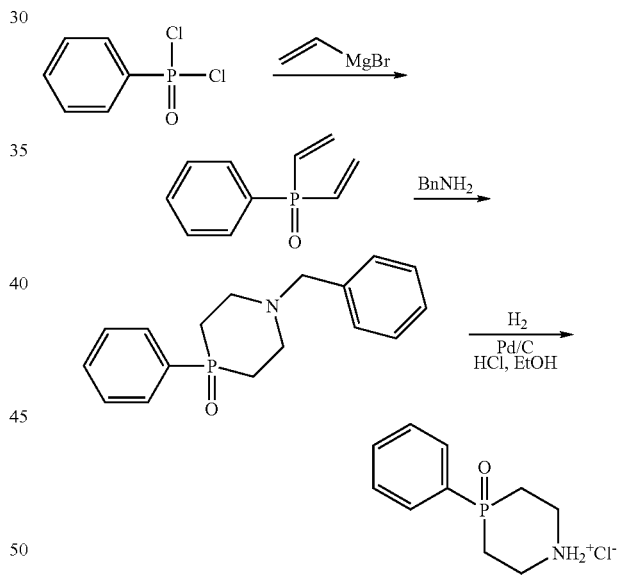

Step 1

A solution of phenylphosphonic dichloride (29 mL, 200 mmol) dissolved in anhydrous THF (600 mL) was cooled to −78° C. and mechanically stirred under an atmosphere of dry nitrogen. Vinylmagnesium bromide (1 M in THF, 500 mL) was slowly added so that the temperature of the reaction mixture never exceeded −70° C. The addition took 2 hours. After an additional 1 hour of stirring at −78° C., the cold reaction mixture was poured directly into cold, saturated NH$_4$Cl (1 L). The mixture was extracted twice with CH$_2$Cl$_2$ and the combined organic phase was washed with 1 M NaOH, brine, and then dried over Mg$_2$SO$_4$. Filtration and solvent evaporation provided divinyl-phenyl-phosphine oxide (26.8 g, 75%) as a viscous yellow oil that solidified upon standing.

$^1$H NMR (400 MHz, DMSO-d6); δ 7.8-7.4 (m, 5H), 6.7 (m, 2H), 6.4-6.1 (m, 4H). $^{31}$P NMR (DMSO-d6); δ 17.0 (s).

Step 2

Divinyl-phenyl-phosphine oxide (26.5 g, 149 mmol) and benzylamine (17.9 mL, 164 mmol) were dissolved in 50% aq. THF (400 mL) and heated to reflux under nitrogen for 38 hours. The cooled reaction mixture was partitioned between saturated aqueous NaHCO$_3$ and CH$_2$Cl$_2$. The aqueous phase was washed once more with CH$_2$Cl$_2$ and the combined organic phase was washed with brine and dried over MgSO$_4$. Filtration and solvent evaporation gave 29 g of a yellow oil, which was purified by flash chromatography on silica gel, eluting with 0-10% MeOH in EtOAc. 1-Benzyl-4-phenyl-[1,4]azaphosphinane 4-oxide was obtained as a yellow solid (25.5 g, 60%). $^1$H NMR (400 MHz, DMSO-d6); δ 7.8 (m, 2H), 7.55 (m, 3H), 7.3 (m, 5H), 3.65 (s, 2H), 2.8 (m, 4H), 2.25 (m, 2H), 1.9 (broad t, 2H). $^{31}$P NMR (DMSO-d6); δ 27.0 (s).

Step 3

1-Benzyl-4-phenyl-[1,4]azaphosphinane 4-oxide (14.2 g, 49.8 mmol) was dissolved in absolute EtOH (65 mL) and 1N HCl (50 mL). Palladium on carbon (10%, 2.0 g) was added and the mixture was hydrogenated on a Parr shaker at 50 psi for 60 hours. After filtration through Celite, the filtrate was rotovapped and the residue was triturated with ether to give 4-phenyl-[1,4]azaphosphinane 4-oxide hydrochloride, as an off-white solid (11.40 g, 99%). $^1$H NMR (400 MHz, DMSO-d6) δ 7.85 (m, 2H), 7.65 (m, 3H), 3.5 (m, 4H), 2.7 (m, 2H), 2.2 (broad t, 2H). $^{31}$P NMR (DMSO-d6); δ 24.0 (s).

The free base of 4-phenyl-[1,4]azaphosphinane 4-oxide hydrochloride was obtained using procedures similar to those described in Intermediate 2 and Example 3, Step 6.

Intermediate 4:
4-(4-Fluorophenylmethyl)-[1,4]azaphosphinane 4-oxide hydrochloride

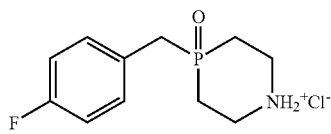

Step 1

4-fluorobenzyl bromide (25 mL, 0.20 mol) was added to a stirred solution of trimethyl phosphite (35.9 mL, 0.30 mol) at ambient temperature, under a nitrogen atmosphere. The resulting solution was heated at 110° C. for six hours, and then at 90° C. overnight. The reaction mixture was allowed to cool to ambient temperature and then ethyl acetate (350 mL) was added. The solution was washed with saturated sodium bicarbonate (350 mL) and then with saturated brine (2×350 mL). The organic phase was dried with magnesium sulfate, filtered, and concentrated by rotatry evaporation. The resulting crude product was purified by flash silica chromatography using 0-35% acetonitrile in ethyl acetate as eluant to yield (4-fluoro-benzyl)-phosphonic acid dimethyl ester (29.44 g, 135 mmol, 66% yield) as a colorless oil. $^1$H NMR (400 MHz, DMSO) δ 7.33-7.28 (m, 2H); 7.17-7.12 (dd, 2H); 3.61-3.58 (d, 6H); 3.31-3.24 (d, 2H); ESMS (m/z): (M+1)$^+$ found, 219.

Step 2

Bromotrimethylsilane (6.0 mL, 45.4 mmol) was added dropwise to (4-fluoro-benzyl)-phosphonic acid dimethyl ester (4.57 g, 20.95 mmol) and stirred in a reaction flask chilled to 0° C. The resulting solution was allowed to warm to ambient temperature and stirred for an additional hour, then concentrated by rotary evaporation to remove volatiles yielding crude (4-fluoro-benzyl) phosphonic acid bis(trimethylsilyl) ester which was used without further purification.

Step 3

To (4-fluoro-benzyl) phosphonic acid bis(trimethylsilyl) ester was added 25 mL of dry methylene chloride, 12 drops of dry DMF, followed by dropwise addition of 6 mL of oxalyl chloride (68.3 mmol). The resulting solution was stirred overnight at ambient temperature as gas was generated. The reaction was concentrated by rotary evaporation to yield 5.2 g of a yellow waxy solid that was purified by distillation at reduced pressure to yield 1.71 g (37%) of 4-fluorobenzyl phosphonic dichloride as a white solid. $^1$H NMR (400 MHz, CDCl$_3$) δ 7.37-7.31 (m, 2H); 7.11-7.05 (m, 2H); 3.93-3.87 (d, 2H).

Step 4

4-Fluorobenzyl phosphonic dichloride (1.71 g, 7.82 mmol) was dissolved in 10 mL of dry THF, under a nitrogen atmosphere, and chilled to −70° C. To this stirred solution was added dropwise vinyl magnesium bromide in THF (18.3 mL, 1M). The resulting solution was stirred for 30 minutes at −70° C. An aqueous solution of ammonium chloride (100 mL, 2 M) was chilled to 0° C. and stirred rapidly while the cold reaction mixture was added. The product was extracted into dichloromethane and washed with saturated aqueous sodium bicarbonate, and then with water. The organic phase was dried with sodium sulfate, filtered, and concentrated by rotary evaporation to yield 1.375 g of (4-fluorophenylmethyl) divinyl phosphine oxide (6.55 mmol, 84%) as a white solid. $^1$H NMR (400 MHz, CDCl$_3$) 7.20-7.14 (m, 2H); 7.01-6.95 (m 2H); 6.29-6.08 (m, 6H); 3.20-3.15 (d, 2H); ESMS (m/z): (M+1)$^+$ found, 211.

Step 5

Divinyl-(4-Fluorophenylmethyl)-phosphine oxide (0.719 g, 3.42 mmol) and benzylamine (0.45 mL, 4.11 mmol) were dissolved in a mixture of THF (15 mL) and deionized water (15 mL). The reaction mixture was heated at 82° C. for 22 hours. The reaction was not complete and so an additional 0.04 mL of benzylamine was added and the reaction mixture was heated for an additional six hours at 90° C. The reaction mixture was concentrated by rotary evaporation and the product was extracted into dichloromethane and washed with saturated brine. The organic phase was dried with sodium sulfate, filtered, and concentrated by rotary evaporation. The crude product was taken up in 1:1 ethyl acetate:dichloromethane and passed through a plug of silica. The product was then eluted from the silica with a solution of 10% methanol in ethyl acetate. The solvents were removed by rotary evaporation to yield 0.84 g of 1-benzyl-4-(4-fluorophenylmethyl)-[1,4]azaphosphinane 4-oxide (2.65 mmol, 77%). $^1$H NMR (400 MHz, CDCl$_3$) δ 7.34-7.25 (m, 5H); 7.25-7.20 (m, 2H); 7.04-6.98. (m, 2H); 3.6 (s, 2H); 3.17-3.12 (d, 2H); 3.00-2.85 (m, 2H); 2.81-2.66 (m, 2H); 1.98-1.75 (m, 4H).

Step 6

1-Benzyl-4-(4-fluorophenylmethyl)-[1,4]azaphosphinane 4-oxide was dissolved in ethanol (100 mL). Aqueous HCl (5.2 mL, 1 M) and of water (20 mL) were added. The solution was degassed with a stream of nitrogen and then palladium on carbon (10%, 0.5 g) was added. The mixture was hydrogenated on a Parr shaker overnight at 60 psi. The mixture was filtered through Celite and all solvents were removed under reduced pressure. The product was recrystallized from methanol/diethyl ether to yield 0.659 g (2.50 mmol, 93%) of 4-(4-fluorophenylmethyl-[1,4]azaphosphinane 4-oxide hydrochloride as a white crystalline solid. $^1$H NMR (400 MHz, DMSO) δ 7.38-7.32 (m, 2H); 7.23-7.18 (m, 2H) 3.46-3.36 (m, 6H); 2.10-1.96 (m, 4H); ESMS (m/z): (M+1)$^+$ found, 228; (M+23)$^+$ found, 250.

The free base of 4-(4-fluorophenylmethyl-[1,4]azaphosphinane 4-oxide hydrochloride was obtained using procedures similar to Intermediate 2 and Example 3, Step 6.

Intermediate 5:
4-(cyclopropylmethyl)-[1,4]azaphosphinane 4-oxide hydrochloride

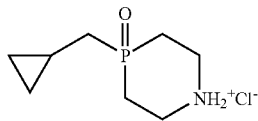

Step 1

Bromomethyl-cyclopropane (26.00 g, 0.193 mol) was added to triisopropyl phosphite (35.9 mL, 0.30 mol) at ambient temperature, under a nitrogen atmosphere. The resulting solution was stirred and heated at reflux (144° C. bath temperature) overnight. The reaction mixture was allowed to cool to ambient temperature and then ethyl acetate (350 mL) was added. The solution was washed with saturated sodium bicarbonate (350 mL) and then with saturated brine (2×350 mL). The organic phase was dried with magnesium sulfate, filtered, and concentrated by rotary evaporation and then under high vacuum to yield 39.96 g of cyclopropylmethyl-phosphonic acid diisopropyl ester (0.182 mol, 94% yield) as a colorless oil. $^1$H NMR (400 MHz, DMSO) δ 4.63-4.54 (m, 2H); 1.67-1.60 (d of d, 2H) 1.27-1.24 (d of d, 12H); 0.85-0.75 (m, 1H); 0.52-0.46 (m, 2H); 0.21-0.16 (m, 2H); ESMS (m/z): M+1)$^+$ found, 221; (M+23)$^+$ found, 243.

Step 2

Bromotrimethylsilane (43 mL, 0.326 mol) was added dropwise to cyclopropylmethyl-phosphonic acid diisopropyl ester (18.00 g, 81.8 mmol) stirred in a reaction flask chilled to 5° C. The resulting solution was allowed to warm to ambient temperature, stirred for three hours, and then concentrated by rotary evaporation yielding crude cyclopropylmethyl-phosphonic acid bis(trimethylsilyl) ester which was used without further purification.

Step 3

To the cyclopropylmethyl-phosphonic acid bis(trimethylsilyl) ester from Step 2 was added dry methylene chloride (100 mL), dry DMF (2 mL), then dropwise of oxalyl chloride (23.3 mL, 267 mmol). The resulting solution was stirred overnight at ambient temperature. The reaction was concentrated by rotary evaporation to yield 16.03 g of a yellow waxy solid that was purified by distillation at reduced pressure to yield 8.50 g of cyclopropylmethyl-phosphonic dichloride (49.1 mmol, 60%) as white solid. $^1$H NMR (400 MHz, DMSO) δ 1.57-1.45 (m, 2H); 0.95-0.75 (m, 1H) 0.53-0.43 (m, 2H); 0.24-0.12 (m, 2H).

Step 4

Cyclopropylmethyl-phosphonic dichloride (8.43 g, 48.7 mmol) was dissolved in dry THF (70 mL), placed under a nitrogen atmosphere, and chilled to −70° C. To this stirred solution was added dropwise vinyl magnesium bromide in THF (122 mL, 1 M). The resulting solution was stirred for 90 minutes at −70° C. An aqueous solution of ammonium chloride (500 mL, 2 M) was chilled to 0° C. and stirred rapidly while the cold reaction mixture was added. The product was extracted into dichloromethane and washed with saturated aqueous sodium bicarbonate and then with water. The organic phase was dried with sodium sulfate, filtered, and concentrated by rotary evaporation to yield 3.56 g of (cyclopropylmethyl)-divinyl-phosphine oxide (22.8 mmol, 47%) as a white solid. $^1$H NMR (400 MHz, CDCl$_3$) δ 6.44-6.14 (m, 6H); 1.84-1.78 (d of d, 2H) 0.98-0.86 (m, 1H); 0.66-0.60 (m, 2H); 0.25-0.19 (m, 2H); ESMS (m/z): (M+1)$^+$ found, 157; (M−1)$^-$ found, 155.

Step 5

Cyclopropylmethyl)-divinyl-phosphine oxide (3.56, 22.8 mmol) and benzylamine (3.0 mL, 27.4 mmol) were dissolved in a mixture of THF (100 mL) and deionized water (100 mL). The reaction mixture was heated at 90° C. for 24 hours. The reaction was not complete and so additional benzylamine (1.0 mL, 9.1 mmol) was added and the reaction mixture was heated for an additional six hours at 90° C. The reaction mixture was concentrated by rotary evaporation and the product was extracted into dichloromethane and washed with saturated brine. The organic phase was dried with sodium sulfate, filtered, and concentrated by rotary evaporation. The crude product was taken up in ethyl acetate and passed through a plug of silica. The product was then eluted from the silica with ethanol. The solvents were removed by rotary evaporation to yield 4.835 g of 1-benzyl-4-(cyclopropylmethyl)-[1,4]azaphosphinane 4-oxide (18.38 mmol, 81%) as an off-white crystalline solid. $^1$H NMR (400 MHz, DMSO) δ 7.38-7.30 (m, 4H); 7.30-7.24 (m, 1H); 3.59 (s, 2H); 2.81-2.63 (m, 4H); 1.94-1.83 (m, 2H); 1.82-1.71 (m, 2H); 1.74-1.68 (d of d, 2H); 0.96-0.83 (m, 1H); 0.56-0.49 (m, 2H); 0.22-0.14 (m, 2H); ESMS (m/z): (M+1)$^+$ found, 264; (M+23)$^+$ found, 286.

Step 6

The material from Step 5 was dissolved in ethanol (80 mL) and aqueous HCl (40 mL, 1 M) was added. The solution was degassed with a stream of nitrogen and palladium on carbon (10%, 1.0 g) was added. The mixture was hydrogenated on a Parr shaker overnight at 20 psi. The reaction mixture was filtered through Celite and the solvents were removed under reduced pressure. The product was dissolved in methanol, and benzene was added. The solvents were removed by rotary evaporation. The product was recrystallized from ethanol/diethyl ether to yield 3.526 g of 4-(cyclopropylmethyl-[1,4] azaphosphinane 4-oxide hydrochloride (16.83 mmol, 92%) as a white crystalline solid. $^1$H NMR (400 MHz, DMSO) 9.60-9.30 (d, 2H); 3.42-3.29 (m, 4H); 2.32-2.21 (m, 2H); 2.16-2.03 (m, 2H); 1.91-1.85 (d of d, 2H); 0.95-0.85 (m, 1H); 0.59-0.51 (m, 2H); 0.26-0.20 (m, 2H); ESMS (m/z): (M+1)$^+$ found, 174; (M+23)$^+$ found, 196.

The free base of 4-(cyclopropylmethyl-[1,4]azaphosphinane 4-oxide hydrochloride was obtained using procedures similar to Intermediate 2.

Intermediate 6:
4—Cyclopropyl-[1,4]azaphosphinane 4-oxide HBF$_4$

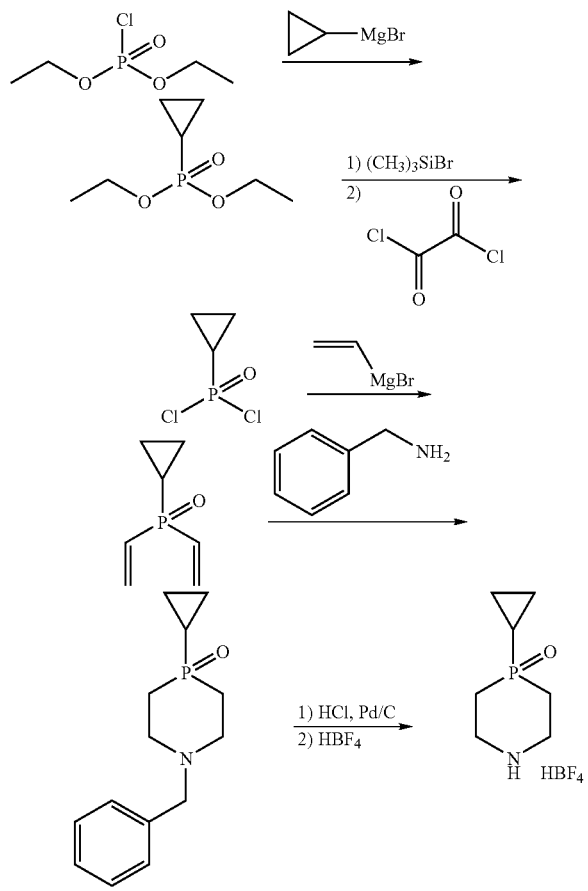

Step 1

To a 200 mL round-bottom flask equipped with a magnetic stir-bar was added phosphorochloridic acid diethyl ester (17.25 mL, 120 mmole) and THF (200 mL). The mixture was cooled to −78° C. and a solution of cyclopropylmagnesium bromide (200 mL, 0.5 M in THF, 100 mmol) was added dropwise over 30 minutes using an addition funnel. The reaction was allowed to slowly warm to room temperature overnight. The resulting clear reaction mixture was poured into saturated NH$_4$Cl (200 mL) and partitioned. The product was extracted from the aqueous layer with diethyl ether (1×100 mL). The organic fractions were combined, dried over sodium sulfate, and concentrated in vacuo. The resulting yellow oil was further purified by vacuum distillation (65-75° C. at 500 mTorr) to provide cyclopropylphosphonic acid diethyl ester (9.025 g, 51%) as a colorless oil. $^1$H NMR (400 MHz, CDCl$_3$) δ 4.11-4.03 (m, 4H), 1.32-1.29 (m, 6H), 0.90-0.77 (m, 5H); $^{13}$C NMR (100 MHz, CDCl$_3$) δ ppm 61.7 (d, J=5.3 Hz), 16.4 (d, J=6.1 Hz), 3.3 (d, J=196.3 Hz), 3.0 (d, J=4.6 Hz).

Step 2

To a 250 mL round bottom flask equipped with a stir-bar was added cyclopropyl phosphonic acid diethyl ester (9.03 g, 51 mmol). The neat solution was cooled to 4° C. by immersion in an ice-water bath. To the rapidly stirred solution was then added trimethylsilyl bromide (20.1 mL, 152 mmol) slowly via syringe. The addition was exothermic and the reaction mixture gently auto-refluxed for several minutes. The ice bath was allowed to warm to room temperature after the addition and the reaction was stirred for an additional 1.5 hours. All volatile reaction components were then removed in vacuo to give the trimethylsilyl ester as a light yellow oil which was used in the next step without further purification.

Step 3

Methylene chloride (75 mL) and DMF (200 μl) were added to the product of step 2 (in the same flask). Oxalyl chloride (12.8 mL, 152 mmol) was added dropwise to the stirring reaction mixture, which was vented to air. Vigorous gas evolution was observed upon addition, which continued for several hours. The vented reaction mixture was stirred overnight, and then all volatile components were removed in vacuo to produce a dark brown syrup. The crude reaction mixture was further purified by bulb-to-bulb distillation (115° C., 5.0 Torr) to give cyclopropyl phosphonic dichloride (3.7 g, 45%) as a light-yellow free flowing oil. $^1$H NMR (400 MHz, CDCl$_3$) δ 1.80-1.65 (m, 1H), 1.40-1.08 (m, 4H); $^{13}$C NMR (100 MHz, CDCl$_3$) δ 20.7 (d, J=151.8 Hz), 6.9 (d, J=5.3 Hz).

Step 4

To a 250 mL round-bottom flask equipped with a magnetic stir-bar was added cyclopropyl phosphonic dichloride (2.33 g, 14.7 mmol) and THF (100 mL). The solution was cooled to −78° C. and vinylmagnesium bromide (58.8 mmol, 1.0 M solution in THF) was added dropwise over 15 minutes. The solution was stirred at −78° C. for 7 hours and then poured, while still cold, into saturated aqueous NH$_4$Cl (200 mL). The resulting solution was extracted with DCM (3×100 mL). The organic layers were combined, washed with brine (2×100 mL), dried over sodium sulfate and concentrated in vacuo to provide cyclopropyl-divinyl-phosphine oxide (0.811 g, 39%) as a light-brown free-flowing oil which was used without further purification. $^1$H NMR (400 MHz, CDCl$_3$) δ 6.40-6.00 (m, 6H), 0.98-0.80 (m, 5H); GC-CIMS (m/z): (M+1)$^+$ found, 142.

Step 5

To a 100 mL round-bottom flask equipped with a magnetic stir-bar was added cyclopropyl-divinyl-phosphine oxide (0.81 g, 5.7 mmol), THF (20 mL), water (20 mL) and benyzlamine (0.73 g, 6.8 mmol). The flask was equipped with a reflux condenser and heated to 85° C. for 16 hours. The THF was removed in vacuo and the resulting cloudy aqueous solution was extracted with DCM. The organic layers were collected, washed with brine, dried over sodium sulfate, and concentrated to provide a yellow oil. The product was further purified by column chromatography eluting with MeOH/HCCl$_3$ (0-10%) to provide 1-benzyl-4-cyclopropyl-[1,4]azaphosphinane 4-oxide (0.77 g, 54%) as a light-yellow oil. $^1$H NMR (400 MHz, CDCl$_3$) δ 7.37-7.26 (m, 5H), 3.35 (s, 2H), 2.82-2.73 (m, 4H), 1.89-1.73 (m, 4H), 1.09-1.01 (m, 1H), 0.83-0.61 (m, 4H); ESMS (m/z): found, 250.

Step 6

To a 500 mL Parr pressure flask was added 1-benzyl-4-cyclopropyl-[1,4]azaphosphinane 4-oxide (0.77 g, 3.1 mmol), ethanol (50 mL), and 1 N aqueous HCl (50 mL). To the solution was then added palladium on carbon (10% w/w, 0.4 g), and the flask was pressurized to 30 psi with shaking. After 48 hours, the catalyst was removed by filtration and the reaction was concentrated in vacuo to produce a waxy solid. The crude product was re-dissolved in a methanolic HBF$_4$ solution (5% v/v) and allowed to crystallize over 24 hours by vapor diffusion of diethyl ether. The resulting crystals were isolated by filtration to provide 4-cyclopropyl-[1,4]azaphosphinane 4-oxide HBF$_4$ salt (0.12 g, 16%) as white needles. $^1$H NMR (400 MHz, d$_6$-DMSO) δ ppm 8.61 (s, 2H), 3.46-3.39 (m, 4H), 2.10-1.99 (m, 4H), 1.26-1.18 (m, 1H), 0.86-0.70 (m, 4H); ESMS (m/z): found, 160.

The free base of 4-cyclopropyl-[1,4]azaphosphinane 4-oxide HBF$_4$ salt was obtained using procedures similar to Intermediate 2.

Intermediate 7:
4-(4-Fluorophenyl)-[1,4]azaphosphinane 4-oxide hydrochloride

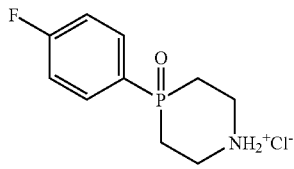

Step 1

4-Bromo-fluorobenzene (10.95 g, 62.57 mmol) was added to diethyl phosphite (8.86 mL, 68.8 mmol) at ambient temperature, followed by the addition of triethylamine (9.6 mL, 68.8 mmol). The resulting solution was degassed with nitrogen followed by the addition of tetrakis(triphenylphosphine)-palladium (3.0 g, 2.6 mmol). The resulting mixture was heated at 90° C. overnight. The reaction mixture was allowed to cool to ambient temperature and then ethyl acetate (350 mL) was added. The solution was washed with saturated sodium bicarbonate (350 mL) and then with saturated brine (2×350 mL). The crude product was purified by vacuum distillation (ca. 98° C., 0.6 Torr) to yield 8.956 g of 4-fluorophenyl-phosphonic acid diethyl ester (38.6 mmol, 94% yield) as a colorless oil. $^1$H NMR (400 MHz, CDCl$_3$) δ 7.88-7.80 (m, 2H); 7.20-7.14 (m 2H); 4.22-4.04 (m, 4H); 1.36-1.32 (t, 6H); ESMS (m/z): M+1)$^+$ found, 233.

Step 2

Bromotrimethylsilane (15.3 mL, 0.116 mol) was added dropwise to 4-fluorophenyl-phosphonic acid diethyl ester (8.95 g, 38.58 mmol) stirred in a reaction flask chilled to 0° C. The resulting solution was allowed to warm to ambient temperature and stirred for an additional hour. The mixture was then concentrated by rotary evaporation yielding crude 4-fluorophenyl-phosphonic acid bis(trimethylsilyl) ester which was used in the next step without further purification.

Step 3

To the 4-fluorophenyl-phosphonic acid bis(trimethylsilyl) ester from Step 2 was added dry methylene chloride (50 mL) and dry DMF (1 mL), followed dropwise by oxalyl chloride (11.0 mL, 126 mmol). The resulting solution was stirred overnight at ambient temperature. The reaction was concentrated by rotary evaporation to yield 10.02 g of a yellow waxy solid that was purified by distillation at reduced pressure to yield 6.86 g of 4-fluorophenyl-phosphonic dichloride (32.2 mmol, 83%) as a yellow oil. $^1$H NMR (400 MHz, CDCl$_3$) δ 8.08-7.98 (m, 2H); 7.35-7.26 (m 2H).

Step 4

4-Fluorophenyl-phosphonic dichloride (6.86 g, 32.2 mmol) was dissolved in dry THF (50 mL), placed under a nitrogen atmosphere, and chilled to −70° C. To this stirred solution was added dropwise a solution of vinyl magnesium bromide in THF (80.5 mL, 1 M). The resulting solution was stirred for 90 minutes at −70° C. An aqueous solution of ammonium chloride (500 mL, 2 M) was chilled to 0° C. and stirred rapidly while the cold reaction mixture was added. The product was extracted into dichloromethane and washed with saturated aqueous sodium bicarbonate followed by water. The organic phase was dried with sodium sulfate, filtered, and concentrated by rotary evaporation to yield 5.214 g of 4-fluoro-phenyl-divinyl-phosphine oxide (26.6 mmol, 83%) as a white solid. $^1$H NMR (400 MHz, CDCl$_3$) 7.80-7.71 (m, 2H); 7.25-7.18 (m 2H); 6.56-6.22 (m, 6H); ESMS (m/z): (M+1)$^+$ found, 197.

Step 5

(4-Fluorophenyl) divinyl phosphine oxide (1.50 g, 7.65 mmol) and benzylamine (1.05 mL, 9.57 mmol) were dissolved in a mixture of 100 mL of THF and 100 mL of deionized water. The reaction mixture was heated at 90° C. overnight. The reaction mixture was concentrated by rotary evaporation and the product was extracted into dichloromethane and washed with saturated brine. The organic phase was dried with sodium sulfate, filtered, and concentrated by rotary evaporation to yield 2.52 g of crude product. Impurities were removed by passing a solution of the crude product in ethyl acetate through a plug of silica. The product was then eluted from the silica with 10% methanol in ethyl acetate. The solvents were removed by rotary evaporation to yield 1.89 g (6.24 mmol, 82%) of 1-benzyl-4-(4-fluorophenyl)-[1,4]azaphosphinane 4-oxide as a colorless oil. ESMS (m/z): (M+1)$^+$ found, 304.

Step 6

1-Benzyl-4-(4-fluorophenyl)-[1,4]azaphosphinane 4-oxide (from Step 5) was dissolved in ethanol (80 mL) and 40 mL of 1 N aqueous HCl was added. The solution was degassed with a stream of nitrogen and then palladium on carbon (10%, 1.0 g) was added. The mixture was hydrogenated on a Parr shaker overnight at 50 psi. The mixture was filtered through Celite and washed with 2:1 ethanol: 1 N HCl and all solvents were removed under reduced pressure. The product was dissolved in ethanol and benzene was added, and the solvents were removed by rotary evaporation. The product was recrystallized from ethanol to yield 1.158 g (4.64 mmol, 61%) of 4-(4-fluorophenyl-[1,4]azaphosphinane 4-oxide hydrochloride as a white crystalline solid. $^1$H NMR (400 MHz, DMSO) δ 9.10-10.10 (d, 2H); 7.88-7.98 (m, 2H); 7.44-7.54 (m, 2H); 3.38-3.57 (m, 4H), 2.65-2.80 (m, 2H); 2.49-2.52 (m, 2H); ESMS (m/z): (M+1)$^+$ found, 214.

The free base of 4-(4-fluorophenyl-[1,4]azaphosphinane 4-oxide hydrochloride was obtained using procedures similar to those described in Intermediate 2 and Example 3, Step 6.

Intermediate 8: 1-Methyl-1-oxo-1λ$^5$-phosphinane-4-carboxylic acid

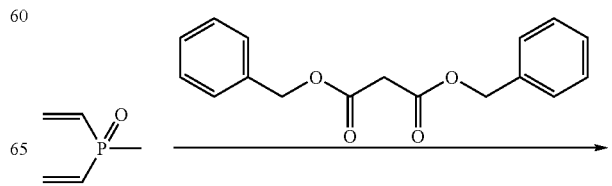

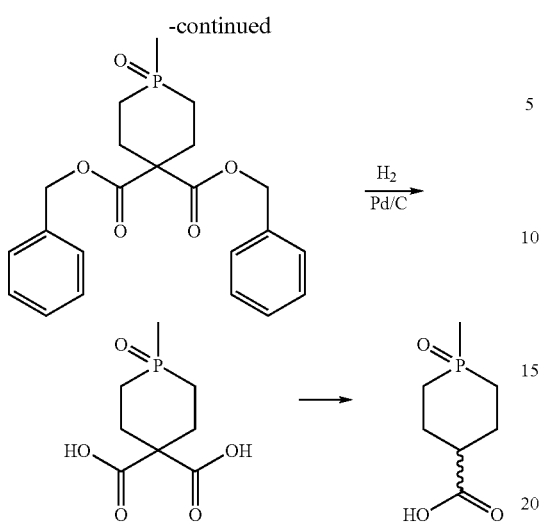

Step 1

To a 1 L round bottom flask equipped with a magnetic stir bar was added divinyl-methyl-phosphine oxide (10 g, 86 mmol), O,O-dibenzylmalonate (27 g, 95 mmol), DMSO (400 mL), and potassium carbonate (18 g, 130 mmol). The heterogeneous mixture was headed to 75° C. After 22 hours, the reaction was complete as determined by analytical HPLC. The reaction was cooled to room temperature, poured onto ice (500 mL) and extracted into EtOAc (3×100 mL). The organic fractions were collected, washed with 1 N aqueous HCl (2×125 mL), saturated sodium bicarbonate (1×100 mL), then brine (3×125 mL). The organic layer was finally washed briefly with an aqueous solution of citric acid (1 N, 50 mL), dried over sodium sulfate, and concentrated to a light brown syrup. The crude product was further purified by silica gel chromatography, eluting with MeOH/EtOAc (5% to 10%) to provide 1-methyl-1-oxo-1$\lambda^5$-phosphinane-4,4-dicarboxylic acid dibenzyl ester (12 g, 35%) as a clear amber colored syrup. $^1$H NMR (400 MHz, CDCl$_3$) δ ppm 7.33-7.29 (m, 6H), 7.27-7.22 (m, 4H), 5.13-5.11 (m, 2H), 2.61-2.50 (m, 2H), 2.33-2.23 (m, 2H), 2.02-1.95 (m, 2H), 1.92-1.73 (m, 2H), 1.45 (d, J=13 Hz, 3H); ESMS m/z: found, 423 (M+Na)$^+$.

Step 2

To a 500 mL Parr flask was added 1-methyl-1-oxo-1$\lambda^5$-phosphinane-4,4-dicarboxylic acid dibenzyl ester (23.0 g, 59.7 mmol). The solid was fully dissolved in ethanol (200 mL). To the solution was added palladium on carbon (10%, 1.15 g), and the flask was charged with hydrogen gas (48 psi). The flask was agitated with a mechanical shaker for 2.5 hours, after which time the starting material was completely consumed as determined by LC-MS. A large amount of white precipitate was present in the reaction mixture. Water (100 mL) and methanol (100 mL) was added to dissolve the precipitate, and the palladium on carbon was removed by filtration through celite, washing with water/methanol (1:1). The resulting filtrate was concentrated in vacuo to remove most of the methanol and ethanol. The remaining water was removed by lyophilization to provide 1-methyl-1-oxo-1$\lambda^5$-phosphinane-4,4-dicarboxylic acid (12.68 g, 96%) as a white free-flowing powder. $^1$H NMR (400 MHz, D$_2$O) δ 2.40-2.20 (m, 4H), 1.95-1.85 (m, 4H), 1.49 (d, J=13.3 Hz, 3H); ESMS m/z: found, 423 (221 (M+1)$^+$, 441 (2M+1)$^+$.

Step 3

To a 50 mL microwave pressure flask equipped with a stir-bar was added 1-methyl-1-oxo-1$\lambda^5$-phosphinane-4,4-dicarboxylic acid (0.25 g, 5.7 mmol) and water (20 mL) to give a suspension. The flask was sealed and heated to 215° C. over 60 seconds, at which point a pressure spike was observed. The flask was allowed to cool to room temperature then vented to release pressure from dissolved CO$_2$. The resulting clear and colorless solution was concentrated by lyophilization to provide 1-methyl-1-oxo-1$\lambda^5$-phosphinane-4-carboxylic acid in quantitative yield as a mixture of cis/trans isomers (~2:1; identity of the favored isomer not determined). $^1$H NMR (400 MHz, D$_2$O) δ ppm 2.6-2.4 (m, 1H), 2.2-1.6 (m, 8H), 1.48 (d, J=12.9 Hz, minor isomer, 1H), 1.44 (d, J=13.7 Hz, major isomer, 2H); ESMS m/z: found, 177 (M+1)$^+$, 353 (2M+1)$^+$.

Intermediate 9: 1-Oxo-1-phenyl-1$\lambda^5$-phosphinane-4,4-dicarboxylic acid dibenzyl ester

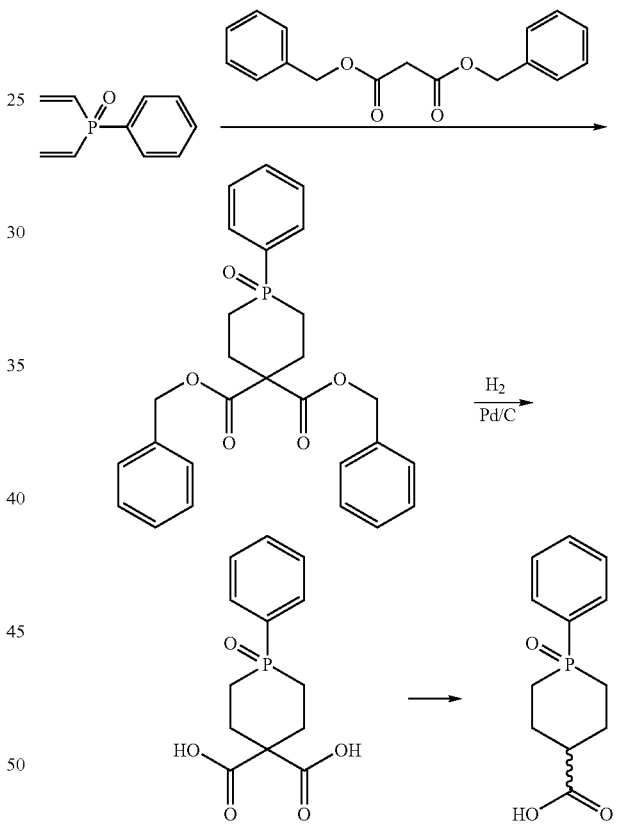

Step 1

To a 1 L round-bottom flask equipped with a magnetic stir-bar was added divinyl-phenyl-phosphine oxide (8.34 g, 46.8 mmol), DMSO (240 mL), dibenzylmalonate (13.31 g, 46.8 mmol), and K$_2$CO$_3$ (9.7 g, 70 mmol). The flask was sealed with a plastic stopper and heated to 75° C. for 2 hours, then cooled to 70° C. and heated an additional 14 hours. The reaction mixture was then cooled to room temperature, poured into 1 N aqueous HCl (300 mL) and extracted into EtOAc (3×100 mL). The organic layers were collected and washed with brine (2×100 mL), dried over sodium sulfate, and concentrated to a dark brown syrup. The crude product was purified by flash chromatography, eluting with MeOH:

DCM (0-20%) to give 1-oxo-1-phenyl-1λ⁵-phosphinane-4,4-dicarboxylic acid dibenzyl ester (8.5 g, 39%) as a light brown syrup. ¹H NMR(400 MHz, CDCl₃) δ 7.48-7.43 (m, 3H), 7.39-7.37 (m, 2H), 7.28-7.19 (m, 10H), 5.12 (s, 3H), 5.09 (s, 3H), 2.56-2.49 (m, 4H), 1.97-1.90 (m, 4H); ESMS m/z: found, 464 (M+1)⁺.

Step 2

To a 500 mL Parr flask was added 1-oxo-1-phenyl-1λ⁵-phosphinane-4,4-dicarboxylic acid dibenzyl ester (8.5 g, 18 mmol), ethanol (250 mL), and palladium on carbon (10%, 1.1 g). The flask was charged with hydrogen (51 psi), and agitated on a mechanical shaker. After 1 hour, the ballast was re-charged to 50 psi (from 40 psi) and shaking continued overnight (14 hours). The reaction mixture was filtered and the solvent removed in vacuo to provide 1-oxo-1-phenyl-1λ⁵-phosphinane-4,4-dicarboxylic acid (1.8 g, 35%) as a white solid. ¹H NMR (400 MHz, d₆-DMSO) δ 7.9-7.4 (m, 5H), 2.6 -1.4 (m, 8H); ESMS m/z: found, 283 (M+1)⁺.

Step 3

To a 250 mL round-bottom flask equipped with a magnetic stir-bar was added 1-oxo-1-phenyl-1λ⁵-phosphinane-4,4-dicarboxylic acid followed by 4 N HCl (100 mL). The flask was equipped with a condenser and heated to a vigorous reflux for 32 hours. The mixture was frozen and lyophilized to give an off white solid, which was redissolved in 1:1 water:MeCN (100 mL), filtered, and lyophilized a second time to provide crude 1-oxo-1-phenyl-1λ⁵-phosphinane-4,4-carboxylic acid, which was used without further purification. ¹H NMR (400 MHz, d₆-DMSO) δ 7.9-7.4 (m, 5H), 2.6-1.4 (m, 9H); ESMS m/z: found, 239 (M+1)⁺.

Intermediate 10: 2-(4-amino-2-cyano-3-methylamino-phenyl)-2-methyl-3-oxo-butyric acid ethyl ester

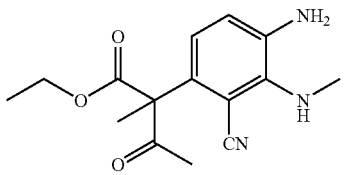

Step 1

To a 1 L two-neck round bottom flask was added 2,6-dichloro-3-nitrobenzonitrile (11.1 g, 51.1 mmol) followed by ethyl acetate (102 mL). The flask was equipped with an internal thermometer and magnetic stir bar and cooled to 5° C. by immersion into an ice bath. Methylamine was added dropwise to the cooled reaction mixture as a 40% aqueous solution (8.9 mL, 115 mmol) with vigorous stirring. The reaction mixture was stirred for an additional 3 hours with cooling, after which more methylamine (1.8 mL, 23 mmol) was added. The reaction vessel was removed from the ice bath and stirred for an additional 1.5 hours. To the reaction mixture was added water (30 mL) followed immediately by hexane (45 mL) and the resulting slurry was stirred for 15 minutes. The solid was recovered by filtration and washed with water followed by methanol to provide 6-chloro-2-methylamino-3-nitro-benzonitrile (10.49 g, 96%) as a bright yellow solid, which was used directly without further purification. 1H NMR (400 MHz, DMSO-d₆) δ 8.55-8.53 (m, 1H), 8.28 (d, 1H, J=9.0 Hz), 6.95 (d, 1H, J=9.0 Hz), 3.30 (d, 1H, J=5.5 Hz).

Step 2

To a 1 L two-neck round bottom flask equipped with a magnetic stir bar and internal thermometer was added potassium tert-butoxide (5.0 g, 45 mmol) and dimethylsulfoxide (100 mL). To the rapidly stirred suspension was added 2-methylacetoacetate (7.13 g, 49.5 mol) dropwise over 5 minutes. After the addition was complete the mixture was clear and slightly yellow. To the reaction mixture was then added 6-chloro-2-methylamino-3-nitro-benzonitrile (8.6 g, 41 mmol) from Step 1 in portions over 15 minutes. The reaction mixture immediately became deep red in color and the temperature rose to 40° C. The reaction mixture was stirred for 1.5 hours, then poured into a saturated solution of NH₄Cl (100 mL). The mixture was extracted with EtOAc (3×150 mL). The organic layers were combined and washed with brine (3×100 mL). The organic layer was dried over sodium sulfate, filtered, and concentrated under vacuum to produce a deep red oil. Methanol (40 mL) was added and the mixture was stirred for 1.5 hours with cooling over an ice bath. The resulting precipitate was recovered by filtration and washed with cold methanol to provide 2-(2-cyano-3-methylamino-4-nitro-phenyl)-2-methyl-3-oxo-butyric acid ethyl ester (7.13 g, 40.6%) as a yellow solid, which was used without further purification. ¹H NMR (400 MHz, DMSO-d₆) δ 8.23 (d, 1H, J=9.0 Hz), 8.10-8.05 (m, 1H), 6.64 (d, 1H, J=9.0 Hz), 4.28-4.19 (m, 2H), 3.17 (d, 3H, J=5.5 Hz), 2.36 (s, 3H), 1.81 (s, 3H), 1.22 (t, 3H, J=7.0 Hz).

Step 3

To a 500 mL Parr pressure flask was added 2-(2-cyano-3-methylamino-4-nitro-phenyl)-2-methyl-3-oxo-butyric acid ethyl ester (7.13 g, 16.5 mmol) as a solution in EtOAc (50 mL) followed by 10% palladium on carbon (1.0 g). The flask was purged under vacuum, then charged with hydrogen gas (50 psi). The flask was agitated at room temperature for while open to the ballast (caution: potential exotherm). After 8 hours, TLC analysis indicated that all starting material has been consumed. The reaction mixture was filtered through a pad of celite and washed with EtOAc. The resulting solution was concentrated to provide 2-(4-amino-2-cyano-3-methylamino-phenyl)-2-methyl-3-oxo-butyric acid ethyl ester (5.11 g, 77%) as a gray solid, which was used without further purification. ¹H NMR (400 MHz, d₆-DMSO) δ 6.70 (d, J=8.2 Hz, 1H), 6.33 (d, J=8.2 Hz, 1H), 6.17 (s, 2H), 4.90 (q, J₁=5.1 Hz, J₂=10.6 Hz, 1H), 4.21-4.15 (m, 2H), 2.95 (d, J=5.5 Hz, 2H), 2.22 (s, 3H), 1.66 (s, 3H), 1.2 (t, J=7.0 Hz, 3H).

Intermediate 11: Acetic acid 1-[2-(2,6-dichloro-phenylamino)-1,6-dimethyl-9-oxo-8,9-dihydro-1H-imidazo[4,5-h]isoquinolin-7-yl]-allyl ester

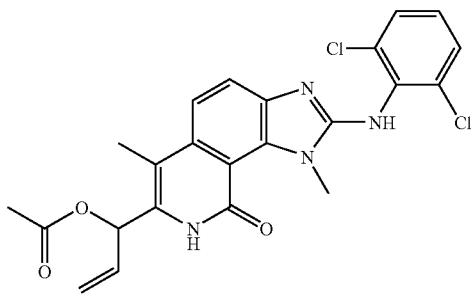

Step 1

2,6-Dichlorophenyl isothiocyanate (3.46 g, 17.0 mmol), THF (100 mL), and 2-(4-amino-2-cyano-3-methylamino-phenyl)-2-methyl-3-oxo-butyric acid ethyl ester (4.91 g, 17.0 mmol), were added to a 250 mL round bottom flask equipped with a magnetic stir bar and the reaction was stirred at room temperature. After 2 hours, mercuric oxide (4.04 g, 18.7 mmol) was added and the reaction stirred for an additional 14 h. The resultant brown slurry was filtered through celite and washed with THF. The filtrate was concentrated and the residue triturated with diethyl ether to provide 2-[4-cyano-2-(2,6-dichloro-phenylamino)-3-methyl-3H-benzoimidazol-5-yl]-2-methyl-3-oxo-butyric acid ethyl ester (4.2 g, 54%) as a gray solid, which was used without further purification.

Step 2

A 25 mL round bottom flask was charged with 2-[4-cyano-2-(2,6-dichloro-phenylamino)-3-methyl-3H-benzoimidazol-5-yl]-2-methyl-3-oxo-butyric acid ethyl ester (0.258 g, 0.562 mmol) and a stir bar. Water (3 mL), glacial acetic acid (3 mL) and concentrated sulfuric acid (3 mL) were combined and added to the round bottom flask while still hot (60° C.). The flask was sealed with a plastic stopper and heated in an oil bath at 100° C. After 2 hours, the flask was removed from the oil bath and stirred at room temperature overnight. The clear solution was then poured onto ice and neutralized with concentrated ammonium hydroxide. The resulting precipitate was recovered by filtration, resuspended in methanol and filtered. The resulting solid was washed with methanol until the filtrate was colorless to provide 2-(2,6-dichloro-phenylamino)-1,6,7-trimethyl-1,8-dihydro-imidazo[4,5-h]isoquinolin-9-one (0.106 g, 46%) as a light gray solid, which was used without further purification. $^1$H NMR (400 MHz, DMSO-$d_6$+TFA) δ 11.47 (s, 1H), 7.78-7.68 (m, 4H), 7.59 (t, 1H, J=8.6 Hz), 4.28 (s, 3H), 2.31 (s, 3H), 2.22 (s, 3H); ESMS (m/z): found, 387.

Step 3

To a 200 mL round bottom flask equipped with a stir bar was added 2-(2,6-dichloro-phenylamino)-1,6,7-trimethyl-1,8-dihydro-imidazo[4,5-h]isoquinolin-9-one (2.4 g, 6.2 mmol), selenium dioxide (2.0 g, 18 mmol) and dioxane (150 mL). The flask was fitted with a condenser and heated to reflux for 4.5 h. The reaction was then removed from heat and allowed to cool to room temperature. The slightly opaque solution was filtered through celite and washed with dichloromethane:methanol (9:1). The solution was concentrated and the resulting residue triturated with dichloromethane to produce 2-(2,6-dichloro-phenylamino)-1,6-dimethyl-9-oxo-8,9-dihydro-1H-imidazo[4,5-h]isoquinoline-7-carbaldehyde (1.8 g, 72%) as a brownish yellow solid, which was used without further purification. $^1$H NMR (400 MHz, DMSO-$d_6$+TFA) δ 10.65 (s, 1H), 10.24 (s, 1H), 7.96 (d, 1H, J=8.6 Hz), 7.78 (d, 1H, J=8.6 Hz), 7.70 (d, 2H, J=7.8 Hz), 7.49 (d, 2H, J=7.8 Hz), 4.15 (s, 3H), 2.70 (s, 3H); ESMS (m/z): found, 401.

Step 4

To a 50 mL round bottom flask equipped with a stir bar was added 2-(2,6-dichloro-phenylamino)-1,6-dimethyl-9-oxo-8,9-dihydro-1H-imidazo[4,5-h]isoquinoline-7-carbaldehyde (0.415 g, 1.03 mmol) and THF (12 mL). The reaction mixture was cooled to –78° C. To the stirred suspension was added vinylmagnesium bromide (5 mL, 1 M in THF, 5 mmol) in one portion. The solution was allowed to gradually warm to –30° C. over 1 h. Additional vinylmagnesium bromide (3 mL, 1 M in THF, 3 mmol) was added and the reaction mixture was further warmed to 0° C. over 1.5 h. The cold reaction mixture was poured into saturated aqueous ammonium chloride (50 mL) and extracted with EtOAc (3×50 mL). The organic fractions were collected, washed with brine (3×25 mL) and concentrated. The resulting solid was further purified by flash chromatography, eluting with EtOAc:Hexane (0-100%) to give 2-(2,6-dichloro-phenylamino)-7-(1-hydroxy-allyl)-1,6-dimethyl-1,8-dihydro-imidazo[4,5-h]isoquinolin-9-one (0.175 g, 40%) as a light yellow solid. $^1$H NMR (400 MHz, DMSO-$d_6$+TFA) δ 10.43 (s, 1H), 7.77-7.75 (m, 4H), 7.59 (t, 1H, J=8.6 Hz), 6.06-5.98 (m, 1H) 5.42 (app d, 1H, J=5.5 Hz), 5.32 (app d, 1H, J=17.2 Hz), 5.16 (app d, 1H, J=10.2 Hz), 4.26 (s, 3H), 2.27 (s, 3H); ESMS (m/z): found, 429.

Step 5

To a 100 mL round bottom flask equipped with a magnetic stir bar was added 2-(2,6-dichloro-phenylamino)-7-(1-hydroxy-allyl)-1,6-dimethyl-1,8-dihydro-imidazo[4,5-h]isoquinolin-9-one (0.175 g, 0.409 mmol), THF (5 mL), triethylamine (60 μL, 0.43 mmol) and acetic anhydride (1 mL). To the stirring suspension was then added N,N-dimethylaminopyridine (2 mg, 0.016 mmol). The reaction mixture became clear in 1 minute, and TLC analysis indicated that all starting material had been consumed. The reaction mixture was concentrated in vacuo and the residue was further purified by silica gel chromatography, eluting with methanol:dichloromethane (0-10%) to provide acetic acid 1-[2-(2,6-dichloro-phenylamino)-1,6-dimethyl-9-oxo-8,9-dihydro-1H-imidazo[4,5-h]isoquinolin-7-yl]-allyl ester (0.168 g, 87%) as a light yellow solid. $^1$H NMR (400 MHz, DMSO-$d_6$+TFA) δ 11.42 (s, 1H), 7.80-7.76 (m, 4H), 7.57 (t, 1H, J=8.2 Hz), 6.34 (d, 1H, J=6.3 Hz), 6.21-6.13 (m, 1H), 5.41 (d, 1H, J=17.2 Hz), 5.33 (d, 1H, J=10.2 Hz), 4.25 (s, 3H), 2.33 (s, 3H), 2.12 (s, 3H); ESMS (m/z): found, 471.

Intermediate 12: 7-(3-Amino-propenyl)-2-(4-fluoro-2-methyl-phenylamino)-1,6-dimethyl-1,8-dihydro-imidazo[4,5-h]isoquinolin-9-one

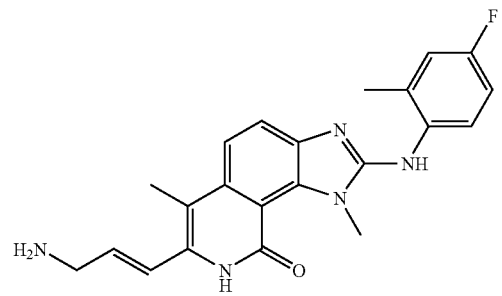

Step 1

To a 50 mL round bottom flask equipped with a magnetic stir bar was added Pd$_2$(dba)$_3$ (38 mg, 42 μmol), triphenylphosphine (52 mg, 200 μmol) and THF (6.6 mL). The resulting solution was stirred under nitrogen for 20 minutes followed by the addition of acetic acid 1-[2-(4-fluoro-2-methyl-phenylamino)-1,6-dimethyl-9-oxo-8,9-dihydro-1H-imidazo[4,5-h]isoquinolin-7-yl]-allyl ester (0.288 mg, 0.664 mmol). The resulting red solution was stirred for 20 minutes, then sodium azide (47 mg, 0.72 mmol) was added as a solution in water (0.6 mL). The flask was sealed with a plastic cap and heated to 60° C. for 3 hours. The reaction mixture was cooled to room temperature and triphenylphosphine (165 mg, 0.63 mmol) was added. After stirring at room temperature for 7 hours, ammonium hydroxide was added (0.7 mL) and the reaction was stirred for 12 additional hours. The reaction mixture was diluted with ethyl acetate (50 mL) and the solution dried over sodium sulfate, filtered, and concentrated in vacuo. The crude product was purified by flash chromatography, eluting with MeOH:HCCl$_3$ (10-40%) to give 7-(3-amino-propenyl)-2-(4-fluoro-2-methyl-phenylamino)-1,6-dimethyl-1,8-dihydro-imidazo[4,5-h]isoquinolin-9-one. $^1$H NMR (400 MHz, d$_6$-DMSO) δ 11.24 (s, 1H), 10.62 (s, 1H), 8.1-8.0 (m, 2H), 7.77 (d, J=9 Hz, 1H), 7.71 (d, J=9 Hz, 1H), 7.6-7.5 (m, 1H), 6.6-6.45 (m, 2H), 4.18 (s, 3H), 3.75-3.65 (m, 2H), 2.36 (s, 3H), 2.30 (s, 3H); ESMS m/z: found, 392 (M+1)$^+$.

Example 1

2-(4-Fluoro-2-methyl-phenylamino)-1,6-dimethyl-7-[3-(4-methyl-4-oxo-4λ$^5$[1,4]azaphosphinan-1-yl)-propenyl]-1,8-dihydro-imidazo[4,5-h]isoquinolin-9-one (Compound 1)

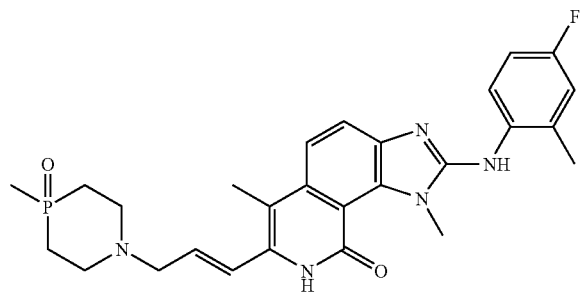

Step 1

To a glass scintillation vial was added 2-(4-amino-2-cyano-3-methylamino-phenyl)-2-methyl-3-oxo-butyric acid ethyl ester (0.247 g, 0.854 mmol), followed by THF (5 mL) and a magnetic stir bar. To the resulting solution was added 4-fluoro-1-isothiocyanato-2-methyl-benzene (0.191 g, 1.14 mmol) and the solution was stirred at room temperature for 48 h. To the solution was then added mercuric oxide (0.222 g, 1.02 mmol), and stirring was continued at room temperature for 24 h. The brown suspension was then filtered through a ½ inch thick pad of silica, washed with THF, and concentrated to dryness. The resulting deep red solid was further purified by silica gel chromatography, eluting with ethyl acetate:hexane (0% -100%) to provide 2-[4-cyano-2-(4-fluoro-2-methyl-phenylamino)-3-methyl-3H-benzoimidazol-5-yl]-2-methyl-3-oxo-butyric acid ethyl ester (0.204 g, 56%) as a deep red solid. ESMS (m/z): (M+1)$^+$ found, 423.

Step 2

To a glass scintillation vial equipped with a magnetic stir bar was added 2-[4-cyano-2-(4-fluoro-2-methyl-phenylamino)-3-methyl-3H-benzoimidazol-5-yl]-2-methyl-3-oxo-butyric acid ethyl ester (0.204 g, 0.483 mmol). A freshly prepared mixture of H$_2$O (3.3 mL), glacial acetic acid (3.3 mL), and concentrated sulfuric acid (3.3 mL) at 60° C. was added to the vial. The vial was sealed with a screw cap and heated to 100° C. in a heating block. After 2.5 hours, the vial was allowed to cool to room temperature and stirred for an additional 12 h. The reaction mixture was then poured onto ice and neutralized by addition of concentrated ammonium hydroxide. The resulting precipitate was recovered by filtration and further purified by trituration with methanol to provide 2-(4-fluoro-2-methyl-phenylamino)-1,6,7-trimethyl-1,8-dihydro-imidazo[4,5-h]isoquinolin-9-one (0.1188 g, 70%) as a light gray solid. 1H NMR (400 MHz, DMSO-d$_6$+TFA) δ 11.43 (br s, 11H), 10.49 (br s, 1H), 7.70-7.65 (m, 2H), 7.57 (dd, 1H, J$_1$=5.5 Hz, J$_2$=8.6 Hz), 7.37 (dd, 11H, J$_1$=3.1 Hz, J$_2$=9.8 Hz), 7.27 (td, 1H, J$_1$=3.1 Hz, J$_2$=11.7 Hz), 4.23 (s, 3H), 2.32 (app s, 6H), 2.23 (s, 3H); ESMS (m/z): found, 351.

Step 3

To a 200 mL round-bottom flask equipped with a magnetic stir bar was added 2-(4-fluoro-2-methyl-phenylamino)-1,6,7-trimethyl-1,8-dihydro-imidazo[4,5-h]isoquinolin-9-one (1.3 g, 3.7 mmol) selenium dioxide (1.23 g, 11.0 mmol) and dioxane (100 mL). The flask was fitted with a reflux condenser and heated to 100° C. in an oil bath for 5 h. The flask was then cooled to room temperature and the mixture filtered through a plug of celite, washing with 10% MeOH/DCM. The filtrate was concentrated to dryness and the resulting brown solid further purified by trituration with cold DCM to give 2-(4-fluoro-2-methyl-phenylamino)-1,6-dimethyl-9-oxo-8,9-dihydro-1H-imidazo[4,5-h]isoquinoline-7-carbaldehyde (1.11 g, 82%) as a red-yellow solid. $^1$H NMR (400 MHz, DMSO-d$_6$+TFA) δ 10.80 (br s, 1H), 10.70 (br s, 1H), 10.25 (s, 1H), 8.02 (d, 1H, J=8.8 Hz), 7.80 (d, 1H, J=8.8 Hz), 7.57 (dd, 1H, J$_1$=5.5 Hz, J$_2$=8.6 Hz), 7.35 (dd, 1H, J$_1$=3.1 Hz, J$_2$=9.8 Hz), 7.26 (td, 1H, J$_1$=3.1 Hz, J$_2$=8.6 Hz), 4.14 (s, 3H), 2.69 (s, 3H), 2.31 (s, 3H); ESMS (m/z): found, 365.

Step 4

To a 100 mL round-bottom flask equipped with a magnetic stir bar was added give 2-(4-fluoro-2-methyl-phenylamino)-1,6-dimethyl-9-oxo-8,9-dihydro-1H-imidazo[4,5-h]isoquinoline-7-carbaldehyde (0.750 g, 2.06 mmol) followed by THF (20 mL). The suspension was cooled to −78° C., then vinylmagnesium bromide (16.5 mmol, 1.0 M in THF) was added over 5 minutes. The reaction mixture was allowed to warm to −10° C. over 2.5 hours, after which time all material was fully dissolved. The cold reaction mixture was poured into saturate aqueous ammonium chloride (100 mL) and extracted with ethyl acetate (3×30 mL). The organic fractions were collected, washed with brine (1×50 mL), dried over sodium sulfate, and concentrated in vacuo to provide 2-(4-fluoro-2-methyl-phenylamino)-7-(1-hydroxy-allyl)-1,6-dimethyl-1,8-dihydro-imidazo[4,5-h]isoquinolin-9-one (0.680 g, 84%) as an orange-yellow solid, which was used without further purification. $^1$H NMR (400 MHz, DMSO-d$_6$+TFA) δ 10.52 (br s, 1H), 10.38 (br s, 1H), 7.71 (app s, 2H), 7.55 (dd, 1H, J$_1$=5.5 Hz, J$_2$=8.6 Hz), 7.35 (dd, 1H, J$_1$=3.1 Hz, J$_2$=9.8 Hz), 7.24 (td, 1H, J$_1$=9.1 Hz, J$_2$=11.7 Hz), 6.02 (ddd, 1H, J$_1$=5.9 Hz, J$_2$=10.6 Hz, J$_3$=17.2 Hz), 5.41 (app d, 1H, J=5.5 Hz), 5.33 (dt, 1H, J$_1$=1.6 Hz, J$_2$=7.2 Hz), 5.17 (dt, 1H, J$_1$=1.2 Hz, J$_2$=10.2 Hz), 4.19 (s, 3H), 2.29 (s, 3H), 2.26 (s, 3H); ESMS (m/z): found, 393.

Step 5

To a 25 mL round-bottom flask equipped with a magnetic stir bar was added 2-(4-fluoro-2-methyl-phenylamino)-7-(1-hydroxy-allyl)-1,6-dimethyl-1,8-dihydro-imidazo[4,5-h]isoquinolin-9-one (0.65 g, 1.7 mmol), THF (5 mL), triethylamine (0.52 g, 5.1 mmol) and acetic anhydride (0.22 g, 2.2 mmol). To the stirred suspension was then added DMAP (0.002 g, 0.02 mmol). After 1 hour, all reaction components were fully dissolved and the reaction was complete as determined by TLC analysis. To the reaction mixture was added saturated aqueous ammonium chloride (20 mL) and the solution was extracted with ethyl acetate (2×20 mL). The organic fractions were collected, washed with brine (1×20 mL), dried over sodium sulfate, and concentrated in vacuo. The crude product was further purified by silica gel chromatography, eluting with 2% methanol:DCM to provide acetic acid 1-[2-(4-fluoro-2-methyl-phenylamino)-1,6-dimethyl-9-oxo-8,9-dihydro-1H-imidazo[4,5-h]isoquinolin-7-yl]-allyl ester (0.404 g, 55%) as a yellow solid. $^1$H NMR (400 MHz, DMSO-d$_6$+TFA) δ ppm 11.35 (br s, 1H), 10.55 (br s, 1H), 7.74 (d, 1H, J=9.0 Hz), 7.70 (d, 1H, J=8.6 Hz), 7.56 (dd, 1H, J$_1$=5.5 Hz, J$_2$=8.6 Hz), 7.37-7.34 (m, 3H), 7.25 (td, 1H, J$_1$=2.7 Hz, J$_2$=8.2 Hz), 6.34 (app d, 1H, J=6.3 Hz), 6.17 (ddd, 1H, J$_1$=6.3 Hz, J$_2$=10.2 Hz, J$_3$=16.8 Hz), 5.41 (app d, 1H, J=17.2 Hz), 5.33 (app d, 1H, J=10.2 Hz), 4.18 (s, 3H), 2.32 (s, 3H), 2.12 (s, 3H); ESMS (m/z): found, 435.

Step 6

To a glass scintillation vial was added 4-methyl-[1,4]azaphosphinane 4-oxide (100 mg, 0.75 mmol). To a separate glass vial was added tris(dibenzylacetone)dipalladium (28 mg, 0.031 mmol), triphenylphosphine (30 mg, 0.12 mmol), and THF (2.5 mL). The resulting solution was stirred for 20 minutes, then acetic acid 1-[2-(4-fluoro-2-methyl-phenylamino)-1,6-dimethyl-9-oxo-8,9-dihydro-1H-imidazo[4,5-h]isoquinolin-7-yl]-allyl ester (0.270 g, 0.621 mmol) was added as a solution in THF (7.0 mL), followed by TEA (0.90 mL, 12.2 mmol). Of the resulting solution, 2.4 mL (0.15 mmol total allylic acetate) was transferred to the vial containing 4-methyl-[1,4]azaphosphinane 4-oxide. The solution was stirred at room temperature for 20 h. The solvent was removed in vacuo and the resulting solid redissolved in MeCN (2 mL) and DMSO (2 mL). The solution was filtered, then purified directly by preperative reverse-phase HPLC (0% to 100% MeCN:H$_2$O+0.1% formic acid) to give 2-(4-fluoro-2-methyl-phenylamino)-1,6-dimethyl-7-[3-(4-methyl-4-oxo-4λ5 [1,4]azaphosphinan-1-yl)-propenyl]-1,8-dihydro-imidazo[4,5-h]isoquinolin-9-one (32 mg, 42%) as a light yellow solid. $^1$H NMR (400 MHz, DMSO-d$_6$+TFA) δ 11.33 (br s, 1H), 10.68 (br s, 1H), 7.79 (d, 1H, J=8.6 Hz), 7.72 (d, 1H, J=8.6 Hz), 7.56 (dd, 1H, J$_1$=5.5 Hz, J$_2$=8.6 Hz), 7.35 (dd, 1H, J$_1$=3.9 Hz, J$_2$=9.8 Hz), 7.25 (td, 1H, J$_1$=3.1 Hz, J$_2$=8.6Hz), 7.19-7.15 (m, 2H), 6.54-6.48 (m, 1H), 4.18 (s, 3H), 4.10-4.00 (br s, 2H), 3.80-3.30 (br m, 4H), 3.16 (s, 3H), 2.36 (s, 3H), 3.31 (s, 3H), 2.30-2.10 (br m, 4H), 1.7-1.6 (br r, 3H); ESMS (m/z): found, 508.

Example 2

2-(2,6-dichloro-phenylamino)-1,6-dimethyl-7-[3-(4-oxo-4-phenyl-4λ$^5$[1,4]-azaphosphinan-1-yl)-propenyl]-1,8-dihydro-imidazo[4,5-h]isoquinolin-9-one (Compound 5)

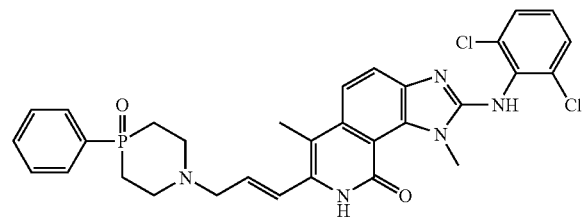

2-(2,6-Dichloro-phenylamino)-1,6-dimethyl-7-[3-(4-oxo-4-phenyl-4λ$^5$-[1,4]azaphosphinan-1-yl)-propenyl]-1,8-dihydro-imidazo[4,5-h]isoquinolin-9-one was prepared following the procedure of Example 1 form acetic acid 1-[2-(2,6-dichloro-phenylamino)-1,6-dimethyl-9-oxo-8,9-dihydro-1H-imidazo[4,5-h]isoquinolin-7-yl]-allyl ester and 4-phenyl-[1,4]azaphosphinane 4-oxide. $^1$HNMR (400 MHz, DMSO-d6+TFA) δ 11.38 (br s, 1H), 10.71 (br s, 1H), 7.90-7.60 (m, 9H), 7.56 (t, 1H, J=7.8 Hz), 7.22 (br d, 1H, J=15.3 Hz), 7.70-6.40 (br m, 1H), 4.23 (s, 3H), 4.18 (br m, 2H), 4.00-4.15 (br m, 4H), 2.60-2.40 (br n, 4H), 2.39 (s, 1H); ESMS (m/z): found, 606 (M+1)$^+$.

Example 3

2-(4-Fluoro-2-methyl-phenylamino)-1,6-dimethyl-7-[3-(4-oxo-4-phenyl-4λ$^5$-[1,4]-azaphosphinan-1-yl)-propenyl]-1,8-dihydro-imidazo[4,5-h]isoquinolin-9-one HCl (Compound 3)

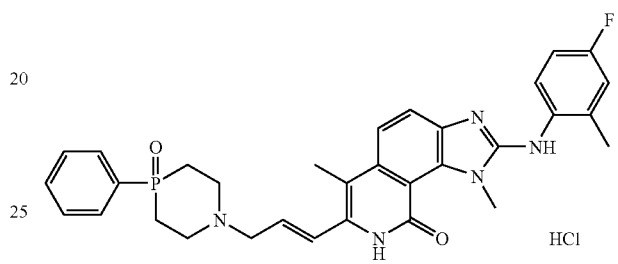

Step 1

To a 250 mL round-bottom flask was added 2-(4-amino-2-cyano-3-methylamino-phenyl)-2-methyl-3-oxo-butyric acid ethyl ester (10.8 g, 37.4 mmol), DMAP (228 mg, 1.87 mmole), and THF (80 mL). The solution was stirred with gentle heating until all the material was fully dissolved. The reaction mixture was then concentrated under vacuum to achieve a final volume of approximately 20 mL. After cooling to room temperature, 4-fluoro-1-isothiocyanato-2-methyl-benzene (9.36 g, 56.0 mmole) was added in one portion, and stirring was continued at room temperature for 12 hours, after which time all the diamine had been converted to the corresponding thiourea as determined by TLC analysis. To the reaction mixture was then added mercuric oxide (12.15 g, 56 mmole) and the resulting slurry stirred at room temperature. The slurry rapidly became black, indicating the formation of mercuric sulfide. After 1 hour, the reaction was complete as determined by TLC analysis. Silica gel was added to the mixture and the resulting thick slurry was filtered through a pad of celite, washing with several volumes of EtOAc. The clear filtrate was concentrated to produce a dark gray solid. To the solid was added diethylether, and the insoluble material was isolated by filtration to provide 2-[4-cyano-2-(4-fluoro-2-methyl-phenylamino)-3-methyl-3H-benzoimidazol-5-yl]-2-methyl-3-oxo-butyric acid ethyl ester (8.25 g, 52%) as a white solid. $^1$H NMR (400 MHz, DMSO-d$_6$) δ 8.71 (s, 1H), 7.46-7.42 (m, 2H), 7.14 (dd, 1H, J$_1$=3.1 Hz, J$_2$=9.8 Hz), 7.06 (td, 1H, J$_1$=2.7 Hz, J$_2$=8.6 Hz), 6.87 (d, 1H, J=8.6 Hz), 4.28-4.19 (m, 2H), 3.95 (s, 3H), 2.30 (s, 3H), 2.22 (s, 3H), 1.81 (s, 3H), 1.23 (t, 3H, J=7.4 Hz); ESMS (m/z): 423 (M+1)$^+$.

Step 2

To a 500 mL round-bottom flask equipped with a magnetic stir-bar was added 2-[4-cyano-2-(4-fluoro-2-methyl-phenylamino)-3-methyl-3H-benzoimidazol-5-yl]-2-methyl-3-oxo-butyric acid ethyl ester (8.25 g, 1.95 mmole), followed by a freshly prepared mixture of water (25 mL), acetic acid (25 mL), and concentrated sulfuric acid (25 mL) at 60° C. The flask was fitted with a reflux condenser and heated to a bath temperature of 100° C. under a nitrogen atmosphere. After 5 hours, the reaction was allowed to cool to room temperature, and stirred for an additional 14 hours. The mixture was then poured onto ice and brought to a slightly basic pH by careful addition of concentrated ammonium hydroxide, while maintaining a temperature of less than 15° C. The resulting precipitate was isolated by filtration, and washed with several volumes of water. The solid was then slurried in methanol for 1 hour, and filtered. The isolated solid was washed with cold methanol until the filtrate was colorless, to provide 2-(4-fluoro-2-methyl-phenylamino)-1,6,7-trimethyl-1,8-dihydro-imidazo[4,5-h]isoquinolin-9-one (6.11 g, 89%) as a light gray solid. $^1$H NMR (400 MHz, DMSO-d$_6$+TFA) δ 11.43 (br s, 1H), 10.49 (br s, 1H), 7.70-7.65 (m, 2H), 7.57 (dd, 1H, $J_1$=5.5 Hz, $J_2$=8.6 Hz), 7.37 (dd, 1H, $J_1$=3.1 Hz, $J_2$=9.8 Hz), 7.27 (td, 1H, $J_1$=3.1 Hz, $J_2$=11.7 Hz), 4.23 (s, 3H), 2.32 (app s, 6H), 2.23 (s, 3H); ESMS (m/z): 351 (M+1)$^+$.

Step 3

To a 1 L round-bottom flask equipped with a magnetic stir-bar was added dioxane (500 mL) and water (16.5 mL). The solution was heated to 55° C., and selenium dioxide (8.6 g, 77 mmole) was added. The mixture was stirred at 55° C. for one hour, over which time all the selenium dioxide had dissolved. To the solution was then added 2-(4-fluoro-2-methyl-phenylamino)-1,6,7-trimethyl-1,8-dihydro-imidazo[4,5-h]isoquinolin-9-one. The flask was fitted with a reflux condenser and the resulting slurry heated to a bath temperature of 115° C. After 18 hours, additional selenium dioxide (4.0 g, 36 mmole) was added and stirring continued for 6 hours. The reaction mixture was dark red, with gray metallic selenium lining the sides of the flask. The reaction mixture was cooled to room temperature then filtered through a pad of celite and washed with 10% MeOH/DCM. The filtrate was concentrated in vacuo to produce a gummy red solid. Methanol (50 mL) was added, and the mixture stirred over an ice bath, during which time a flocculent yellow precipitate formed. The solid was isolated by filtration, and washed sparingly with cold methanol to give 2-(4-fluoro-2-methyl-phenylamino)-1,6-dimethyl-9-oxo-8,9-dihydro-1H-imidazo[4,5-h]isoquinoline-7-carbaldehyde (3.90 g, 61%) as a bright yellow solid. $^1$H NMR (400 MHz, DMSO-d$_6$+TFA) δ 10.80 (br s, 1H), 10.70 (br s, 1H), 10.25 (s, 1H), 8.02 (d, 1H, J=8.8 Hz), 7.80 (d, 1H, J=8.8 Hz), 7.57 (dd, 1H, $J_1$=5.5 Hz, $J_2$=8.6 Hz), 7.35 (dd, 1H, $J_1$=3.1 Hz, $J_2$=9.8 Hz), 7.26 (td, 1H, $J_1$=3.1 Hz, $J_2$=8.6 Hz), 4.14 (s, 3H), 2.69 (s, 3H), 2.31 (s, 3H); ESMS (m/z): 365 (M+1)$^+$.

Step 4

To a 1 L 3-neck round-bottom flask equipped with a magnetic stir-bar was added 2-(4-fluoro-2-methyl-phenylamino)-1,6-dimethyl-9-oxo-8,9-dihydro-1H-imidazo[4,5-h]isoquinoline-7-carbaldehyde (7.96 g, 21.9 mmole) and THF (260 mL). The resulting slurry was cooled to −78° C., and vinylmagnesium bromide (175 mL, 1.0 M in THF) was added dropwise over 30 minutes. The mixture was stirred at −78° C. for 2 hours, then warmed to -10° C. over 30 minutes and maintained at −10° C. for an additional 2 hours. The reaction was then quenched by addition of saturated aqueous ammonium chloride (200 mL), and extracted into EtOAc (2×200 mL). The organic layers were collected, washed with brine (2×100 mL), dried over sodium sulfate, and concentrated in vacuo to provide 2-(4-fluoro-2-methyl-phenylamino)-7-(1-hydroxy-allyl)-1,6-dimethyl-1,8-dihydro-imidazo[4,5-h]isoquinolin-9-one (7.8 g, 91%) as an orange-yellow solid, which was used without further purification. $^1$H NMR (400 MHz, DMSO-d$_6$+TFA) δ 10.52 (br s, 1H), 10.38 (br s, 1H), 7.71 (app s, 2H), 7.55 (dd, 1H, $J_1$=5.5 Hz, $J_2$=8.6 Hz), 7.35 (dd, 1H, $J_1$=3.1 Hz, $J_2$=9.8 Hz), 7.24 (td, 1H, $J_1$=9.1 Hz, $J_2$=11.7 Hz), 6.02 (ddd, 1H, $J_1$=5.9 Hz, $J_2$=10.6 Hz, $J_3$=17.2 Hz), 5.41 (app d, 1H, J=5.5 Hz), 5.33 (dt, 1H, $J_1$=1.6 Hz, $J_2$=17.2 Hz), 5.17 (dt, 1H, $J_1$=1.2 Hz, $J_2$=10.2 Hz), 4.19 (s, 3H), 2.29 (s, 3H), 2.26 (s, 3H); ESMS (m/z): 393 (M+1)$^+$.

Step 5

To a 500 mL round-bottom flask equipped with a magnetic stir-bar was added 2-(4-fluoro-2-methyl-phenylamino)-7-(1-hydroxy-allyl)-1,6-dimethyl-1,8-dihydro-imidazo[4,5-h]isoquinolin-9-one (7.8 g, 20 mmole), DCM (100 mL), TEA (3.0 g, 30 mmole), and DMAP (25 mg, 0.2 mmole). To the rapidly stirred suspension at room temperature was added acetic anhydride (2.3 g, 23 mmole). The reaction was complete after 10 minutes as determined by TLC analysis. The mixture was diluted with DCM (100 mL), and washed with saturated aqueous ammonium chloride. The aqueous layer was back-extracted with additional DCM (100 mL). The combined organic fractions were washed with brine (2×100 mL), dried over sodium sulfate, and concentrated in vacuo to give an amorphous orange solid. The crude product was re-dissolved in 5% MeOH/DCM (65 mL). To the stirred solution was added diethyl ether (200 mL), which resulted in the formation of a bright yellow precipitate. The stirred suspension was cooled over a salt/ice bath to −-5° C., then filtered to recover the solids. The solids were washed sparingly with diethyl ether and collected to provide acetic acid 1-[2-(4-fluoro-2-methyl-phenylamino)-1,6-dimethyl-9-oxo-8,9-dihydro-1H-imidazo[4,5-h]isoquinolin-7-yl]-allyl ester (6.94 g, 80.4%) as a yellow powder. $^1$H NMR (400 MHz, DMSO-d$_6$+TFA) δ 11.35 (br s, 1H), 10.55 (br s, 1H), 7.74 (d, 1H, J=9.0 Hz), 7.70 (d, 1H, J=8.6 Hz), 7.56 (dd, 1H, $J_1$=5.5 Hz, $J_2$=8.6 Hz), 7.37-7.34 (m, 3H), 7.25 (td, 1H, $J_1$=2.7 Hz, $J_2$=8.2 Hz), 6.34 (app d, 11H, J=6.3 Hz), 6.17 (ddd, 1H, $J_1$=6.3 Hz, $J_2$=10.2 Hz, $J_3$=16.8 Hz), 5.41 (app d, 1H, J=17.2 Hz), 5.33 (app d, 1H, J=10.2 Hz), 4.18 (s, 3H), 2.32 (s, 3H), 2.12 (s, 3H); ESMS (m/z): 435 M+1)$^+$.

Step 6

To a 500 mL round-bottom flask was added 4-phenyl-[1,4]azaphosphinane 4-oxide hydrochloride salt (5.91 g, 25.6 mmole), MP-carbonate resin (20 g, 2.9 mmole/g), and water (200 mL). The flask was sealed with a plastic stopper and placed on an orbital shaker for 12 hours. The resin was then removed by filtration with though a glass frit, and washed with water (40 mL) to provide 4-phenyl-[1,4]azaphosphinane 4-oxide free-base as an aqueous solution.

Step 7

To a 500 mL 3-neck round-bottom flask equipped with a magnetic stir-bar and internal thermometer was added Pd$_2$(dba)$_3$.HCCl$_3$ (0.476 g, 0.46 mmole), triphenylphosphine (0.383 g, 1.5 mmol), and THF (100 mL). The resulting wine-red solution was stirred under a nitrogen atmosphere for 30 minutes. To the stirred solution was then added solid acetic acid 1-[2-(4-fluoro-2-methyl-phenylamino)-1,6-dimethyl-9-oxo-8,9-dihydro-1H-imidazo[4,5-h]isoquinolin-7-yl]-allyl ester (4.0 g, 9.2 mmole) in a single portion. An aqueous solution of 4-phenyl-[1,4]azaphosphinane 4-oxide free-base (200 mL, 0.106 M) was next added to the stirring solution over 3 minutes via an addition funnel. The temperature of the reaction immediately rose from 24° C. to 29.5° C. and maintained this temperature for about 20 minutes. After 1 hour, the reaction mixture had cooled to room temperature and a yellow precipitate had formed. The precipitate was isolated by filtration and washed with water followed by diethyl ether. The filter cake was re-dissolved in methanol (150 mL) and cooled over an ice bath. To the chilled solution with rapid stirring was added anhydrous HCl (10 mL, 1.25 M in methanol). The solution was then poured into a flask containing diethyl ether (600 mL) with stirring. Pentane (100 mL) was added, followed by additional anhydrous HCl (20 mL, 1.25 M in methanol). The resulting solution was decanted, leaving crude product as a gum on the sides of the flask. This material was re-dissolved in methanol (100 mL). Into the stirred solution was poured diethyl ether, resulting in a yellow flocculent precipitate. This was recovered by filtration and washed with diethyl ether to give 2-(4-fluoro-2-methyl-phenylamino)-1,6-dimethyl-7-[3-(4-oxo-4-phenyl-4λ⁵-[1,4]azaphosphinan-1-yl)-propenyl]-1,8-dihydro-imidazo[4,5-h]isoquinolin-9-one HCl salt (2.9 g, 52%). ¹H NMR (400 MHz, CD₃OD) δ 7.96-7.89 (m, 2H), 7.89 (d, 1H, J=9.0 Hz), 7.73 (d, 1H, J=9.0 Hz), 7.71-7.65 (n, 1H), 7.66-7.61 (m, 2H), 7.51 (dd, 1H, $J_1$=5.5 Hz, $J_2$=8.6 Hz), 7.32 (d, 1H, J=15.7 Hz), 7.26 (dd, 1H, $J_1$=3.1 Hz, $J_2$=9.4 Hz), 7.16 (td, 1H, $J_1$=3.1 Hz, $J_2$=8.6 Hz), 6.56-6.48 (m, 1H), 4.26 (s, 3H), 4.19 (d, 2H, J=7.0 Hz), 4.2-3.8 (br m, 2H), 3.8-3.6 (br m, 2H), 3.0-2.9 (br m, 2H), 2.47 (s, 3H), 2.37 (s, 3H), 2.5-2.3 (br m, 2H); ESMS m/z 569.7 (MH+).

Example 4

2-(4-fluoro-2-methyl-phenylamino)-1,6-dimethyl-7-{3-[4-(4-fluorophenylmethyl)-4-oxo-4λ⁵-[1,4]azaphosphinan-1-yl]-propenyl}-1,8-dihydro-imidazo[4,5-h]isoquinolin-9-one (Compound 12)

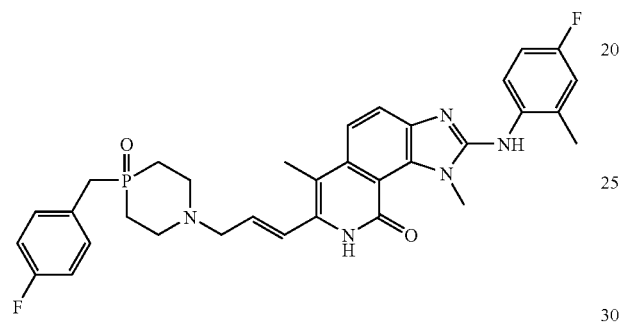

Proceeding as above for Example 3, 2-(4-fluoro-2-methyl-phenylamino)-1,6-dimethyl-7-{3-[4-(4-fluorophenylmethyl)-4-oxo-4λ⁵-[1,4]azaphosphinan-1-yl]-propenyl}-1,8-dihydro-imidazo[4,5-h]isoquinolin-9-one was prepared by replacing 4-methyl-[1,4]azaphosphinane 4-oxide with 4-(4-fluorophenylmethyl)-[1,4]azaphosphinane 4-oxide. 1H NMR (400 MHz, DMSO-d₆+TFA) δ 11.32 (br s, 1H), 10.62 (br s, 1H), 7.79 (d, 1H, J=9.2 Hz), 7.72 (d, 1H, J=9.2 Hz), 7.56 (dd, 1H, $J_1$=6.0 Hz, $J_2$=8.8 Hz), 7.37-7.28 (m, 3H), 7.25 (dt, 1H, $J_1$=2.8 Hz, $J_2$=8.8 Hz), 7.23-7.14 (m, 3H), 6.48 (dt, 1H, $J_1$=7.2 Hz, $J_2$=14.8 Hz), 4.17 (s, 3H), 4.07 (d, 2H, J=6.8 Hz), 3.8-3.6 (br m, 2H), 3.6-3.4 (br m, 4H), 2.36 (s, 3H), 2.30 (s, 3H), 2.4-2.0 (br m, 4H); ESMS (m/z): found, 602.1 (M+1)⁺.

Example 5

2-(4-fluoro-2-methyl-phenylamino)-1,6-dimethyl-7-{3-[4-(cyclopropylmethyl)-4-oxo-4λ⁵-[1,4]azaphosphinan-1-yl]-propenyl}-1,8-dihydro-imidazo[4,5-h]isoquinolin-9-one (Compound 13)

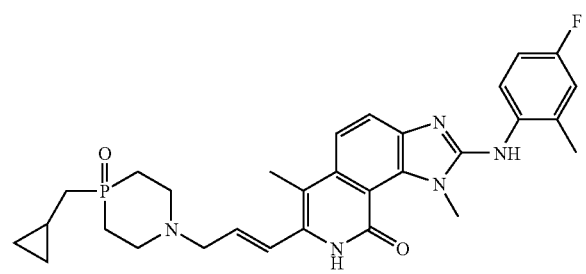

Proceeding as above for Example 3, 2-(4-fluoro-2-methyl-phenylamino)-1,6-dimethyl-7-{3-[4-(cyclopropylmethyl)- 4-oxo-4λ⁵-[1,4]azaphosphinan-1-yl]-propenyl}-1,8-dihydro-imidazo[4,5-h]isoquinolin-9-one was prepared by replacing 4-methyl-[1,4]azaphosphinane 4-oxide with 4-cyclopropylmethyl-[1,4]azaphosphinane 4-oxide. ¹H NMR (400 MHz, DMSO-d₆+TFA) δ 11.08 (br s, 1H), 10.70 (s, 1H), 7.79 (d, 1H, J=8.8 Hz), 7.72 (d, 1H, J=8.8 Hz), 7.55 (dd, 1H, $J_1$=5.5 Hz, $J_2$=8.6 Hz), 7.35 (dd, 1H, $J_1$=2.7 Hz, $J_2$=9.8 Hz), 7.25 (td, 1H, $J_1$=3.1 Hz, $J_2$=8.6 Hz), 7.30-7.10 (br m, 1H), 6.6-6.45 (br m, 1H), 4.18 (s, 3H), 4.10-4.00 (br m, 2H), 3.80-3.65 (br m, 2H), 3.60-3.45 (br m, 1H), 3.45-3.30 (br m, 1H), 2.36 (s, 3H), 2.31 (s, 3H), 2.50-1.70 (m, 6H), 1.0-0.70 (br m, 1H), 0.56 (d, 2H, J=7.4 Hz), 0.23 (s, 2H);-ESMS (m/z): found, 548 (M+1)⁺.

Example 6

2-(4-fluoro-2-methyl-phenylamino)-1,6-dimethyl-7-{3-[4-(cyclopropyl)-4-oxo-4λ⁵-[1,4]azaphosphinan-1-yl]-propenyl}-1,8-dihydro-imidazo[4,5-h]isoquinolin-9-one (Compound 14)

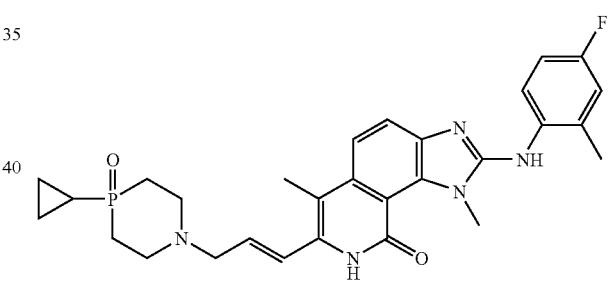

Proceeding as above for Example 3, 2-(4-fluoro-2-methyl-phenylamino)-1,6-dimethyl-7-{3-[4-(cyclopropyl)-4-oxo-4λ⁵-[1,4]azaphosphinan-1-yl]-propenyl}-1,8-dihydro-imidazo[4,5-h]isoquinolin-9-one was prepared by replacing 4-methyl-[1,4]azaphosphinane 4-oxide with 4-cyclopropyl-[1,4]azaphosphinane 4-oxide. ¹H NMR (400 MHz, DMSO-d₆+TFA) δ 11.37 (br s, 1H), 10.63 (s, 1H), 10.49 (br s, 1H), 7.80 (d, 1H, J=8.8 Hz), 7.72 (d, 1H, J=8.8 Hz), 7.56 (dd, 1H, $J_1$=5.5 Hz, $J_2$=8.6 Hz), 7.36 (dd, 1H, $J_1$=2.7 Hz, $J_2$=7.8 Hz), 7.26 (td, 1H, $J_1$=2.7 Hz, $J_2$=8.2 Hz), 7.18 (br d, 1H, 15.3 Hz), 6.60-6.50 (br m, 1H), 4.18 (s, 3H), 4.15-4.05 (br m, 2H), 4.00-3.40 (br m, 4H), 2.37 (s, 3H), 2.30 (s, 3H), 2.50-2.10 (br m, 4H), 1.50-1.00 (br m, 1H), 0.90-0.82 (br m, 2H), 0.81-0.70 (br m, 2H); ESMS (m/z): found, 534 (M+1)⁺.

Example 7

2-(4-fluoro-2-methyl-phenylamino)-7-[3-(4-methanesulfonyl-piperazin-1-yl)-propenyl]-1,6-dimethyl-1,8-dihydro-imidazo[4,5-h]isoquinolin-9-one (Compound 24)

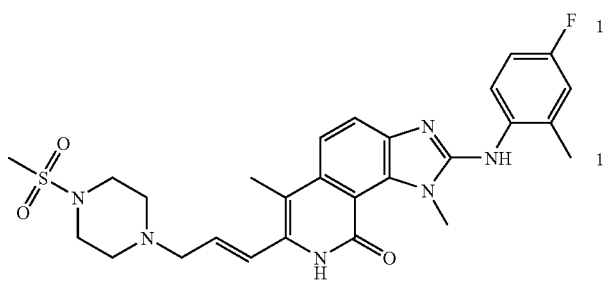

Proceeding as above for Example 3, 2-(4-fluoro-2-methyl-phenylamino)-7-[3-(4-methanesulfonyl-piperazin-1-yl)-propenyl]-1,6-dimethyl-1,8-dihydro-imidazo[4,5-h]isoquinolin-9-one was prepared by replacing 4-phenyl-[1,4]azaphosphinane 4-oxide hydrochloride with methansulfonylpiperazine. $^1$H NMR (400 MHz, DMSO-d$^6$) (free base) δ 10.78 (1H, s); 8.41 (1H, m); 7.69 (d, 1H, J=9.0 Hz); 7.7-7.66 (1H, m); 7.5 (1H, J=9 Hz); 7.07 (1H, m); 7.02 (1H, m); 6.82 (1H, d); 6.5 (1H, m) 14.08 (3H, s); 3.26 (2H, m); 3.19 (4H, m); 2.92 (3H, s); 2.59 (4H, m); 2.37 (3H, s); 2.26 (3H, s). ESMS m/z 539 (MH+).

Example 8

2-(4-Fluoro-2-methyl-phenylamino)-1,6-dimethyl-7-{3-[(1-methyl-1-oxo-phosphinan-4-yl)carbonylamino]-propenyl}-1,8-dihydro-imidazo[4,5-h]isoquinolin-9-one (Compound 15)

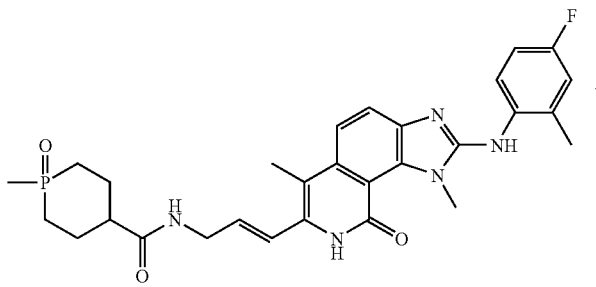

Step 1

To scintillation vial with a magnetic stir-bar was added 7-(3-amino-propenyl)-2-(4-fluoro-2-methyl-phenylamino)-1,6-dimethyl-1,8-dihydro-imidazo[4,5-h]isoquinolin-9-one (68 mg, 173 mmol), followed by dimethylformamide (DMF) (1.0 mL) and triethylamine (TEA) (0.25 mL). To a separate scintillation vial was added 1-methyl-1-oxo-1λ$^5$-phosphinane-4-carboxylic acid (130 mg, 0.74 mmol, mixture of cis/trans isomers), HATU (300 mg, 0.79 mmol), and DMF (2.0 mL), followed by TEA (0.25 mL). The solution was sonicated until most of the solids were dissolved. A solution of the activated ester (1.0 mL, or roughly half) was transferred to the solution of amine and stirred for 2.5 hours at room temperature, after which time the starting material was completely consumed as determined by LC-MS. The reaction mixture was quenched by addition of water (0.5 mL), then acidified with TFA. The mixture was filtered (syringe membrane filter) and purified directly by reverse-phase HPLC to provide 2-(4-fluoro-2-methyl-phenylamino)-1,6-dimethyl-7-{3-[(1-methyl-1-oxo-phosphinan-4-yl)carbonylamino]-propenyl}-1,8-dihydro-imidazo[4,5-h]isoquinolin-9-one (24.9 mg, 26%) as a mixture of cis/trans isomers. $^1$H NMR (400 MHz, d$_6$-DMSO) δ 11.12 (s, 1H), 10.55 (s, 1H), 8.21-8.17 (m, 1H), 7.74 (d, J=8.6Hz, 1H), 7.69 (d, J=8.6Hz, 1H), 7.55 (dd, J$_1$=5.9 Hz, J$_2$=9.0 Hz, 1H), 7.27 (td, J$_1$=2.7 Hz, J$_2$=8.6 Hz, 1H), 6.66 (d, J=15 Hz, 1H), 6.55-6.49 (m, 1H), 4.18 (s, 3H), 3.92 (m, 2H), 2.31 (s, 3H), 2.30 (s, 3H), 2.35-2.30 (m, 1H), 2.08-1.90 (m, 6H), 1.78-1.65 (m, 2H), 1.52-1.47 (m, 3H); ESMS m/z: found, 550 (M+1)$^+$.

Example 9

2-(4-fluoro-2-methyl-phenylamino)-1,6-dimethyl-7-{3-[(trans-1-phenyl-1-oxo-phosphinan-4-yl)carbonylamino]-propenyl}-1,8-dihydro-imidazo[4,5-h]isoquinolin-9-one (Compound 16) and 2-(4-fluoro-2-methyl-phenylamino)-1,6-dimethyl-7-{3-[(cis-1-phenyl-1-oxo-phosphinan-4-yl)carbonylamino]-propenyl}-1,8-dihydro-imidazo[4,5-h]isoquinolin-9-one (Compound 17)

Compound 16

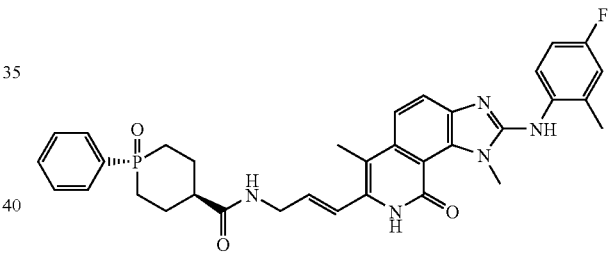

Compound 17

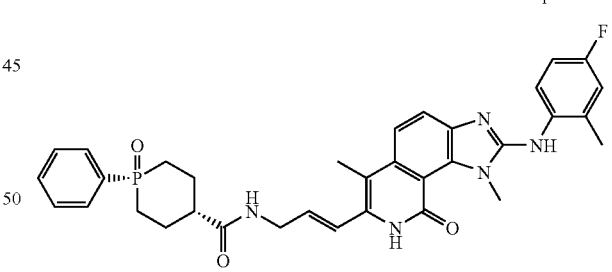

To a scintillation vial was added 7-(3-amino-propenyl)-2-(4-fluoro-2-methyl-phenylamino)-1,6-dimethyl-1,8-dihydro-imidazo[4,5-h]isoquinolin-9-one (70 mg, 180 μmol), DMF (2.0 mL), and TEA (110 mg, 1.1 mmol). To a separate vial was added crude 1-oxo-1-phenyl-1λ$^5$-phosphinane-4,4-carboxylic acid (64 mg, 270 μmol), HATU (108 mg, 284 μmol), and DMF (2.0 mL). Once the solution of activate ester had fully dissolved, the entire volume was transferred to the solution of amine. The reaction mixture was stirred at room temperature for 2 hours, then quenched by addition of saturated aqueous ammonium chloride solution (10 mL). The mixture was extracted with EtOAc (3×10 mL), washed with brine, dried over sodium sulfate, and concentrated in vacuo.

The crude material was further purified by flash chromatography, eluting with MeOH:DCM (5-25%) to provide 1-oxo-1-phenyl-1λ⁵-phosphinane-4-carboxylic acid {3-[2-(4-fluoro-2-methyl-phenylamino)-1,6-dimethyl-9-oxo-8,9-dihydro-1H-imidazo[4,5-h]isoquinolin-7-yl]-allyl}-amide as two chromatographically distinct geometric isomers (12.7 mg of the first eluting isomer and 10.5 mg of the second eluting isomer, 21% combined yield). The first eluting isomer: $^1$H NMR (400 MHz, d$_6$-DMSO+TFA) δ 11.09 (s, 1H), 10.56 (s, 1H), 8.21 (t, J=6.3 Hz, 1H), 7.83-7.81 (m, 2H), 7.73 (d, J=8.6 Hz, 1H), 7.66 (d, J=8.6 Hz, 1H), 7.61-7.53 (m, 4H), 7.36-7.33 (m, 1H), 7.25 (td, J$_1$=3.1 Hz, J$_2$=8.2 Hz, 1H), 6.63 (d, J=16 Hz, 1H), 6.47 (dt, J$_1$=5.1 Hz, J$_2$=16 Hz, 1H), 4.18 (s, 3H), 3.9-3.86 (m, 2H), 2.30 (s, 3H), 2.28 (s, 3H), 2.7-1.9 (m, 7H), 1.7-1.6 (2H); ESMS m/z: found, 612 (M+1)⁺. The second eluting isomer: $^1$H NMR (400 MHz, d$_6$-DMSO+TFA) δ 11.16 (s, 1H), 10.57 (s, 1H), 8.25 (t, J=5.8 Hz, 1H), 7.87-7.82 (m, 1H), 7.77 (d, J=9 Hz, 1H), 7.71 (d, J=9 Hz, 1H), 7.62-7.5 (m, 4H), 7.38-7.32 (m, 2H), 7.28 (td, J$_1$=3.1 Hz, J$_2$=8.6 Hz, 1H), 6.76 (d, J=16 Hz, 1H), 6.6-6.5 (m, 1H), 4.20 (s, 3H), 4.0-3.9 (m, 2H), 2.35 (s, 3H), 2.33 (s, 3H), 2.37-2.29 (m, 1H), 2.11-2.00 (m, 8H); ESMS m/z: found, 612 (M+1)⁺.

Example 10

2-(4-Fluoro-2-methylphenylamino)-7-{3-[4-(4-fluorophenyl)-piperazin-1-yl]-propenyl}-1,6-dimethyl-1,8-dihydro-inidazo[4,5-h]isoquinolin-9-one (Compound 30)

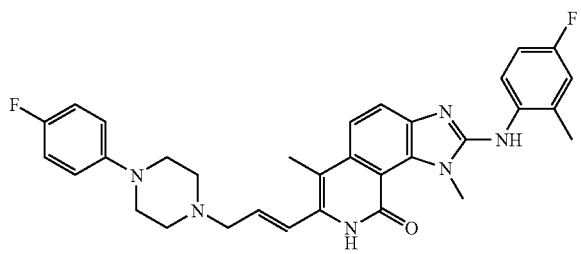

2-(4-Fluoro-2-methylphenylamino)-7-{3-[4-(4-fluorophenyl)-piperazin-1-yl]-propenyl}-1,6-dimethyl-1,8-dihydro-imidazo[4,5-h]isoquinolin-9-one was prepared following the procedure in Example 3, but replacing 4-phenyl-[1,4]azaphosphinane 4-oxide with 4-fluorophenylpiperazine. $^1$H NMR (400 MHz DMSO-d$^6$) (free base) δ ppm 10.78 (1H, s); 8.4 (1H, s); 7.67 (1H, d); 7.58 (1H, dd); 7.45 (1H, d); 7.07 (1H, m); 7.02 (2H, m); 6.95 (2H, m); 6.9 (1H, d); 6.56 (1H, td); 4.05 (3H, s): 3.23 (2H, d); 3.1 (4H, br. s); 2.61 (4H, br. s); 2.36 (3H, s); 2.23 (3H, s). ESMS m/z 539 (MH+).555.2.

Example 11

Inhibitory Activity Against Kinases: Enzyme Assays and Cellular Assays

Suitable in vitro assays for measuring kinase activity and the inhibition thereof by compounds are known (e.g., see Kuzmic et al. *Anal. Biochem.* 2000, 286, 45-50).

The following protocol represents an assay for determination of inhibition of kinases under physiological conditions (pH 7.4). Kinase activity was determined using a time-resolved fluorescence resonance energy transfer (TR-FRET) methodology. Measurements were performed in a reaction volume of 50 µL using 96-well assay plates. Kinase enzyme, inhibitor, ATP (at the K$_m$ for the kinase), and 1 µM peptide substrate (Biotin-AVLESEEELYSSARQ-NH$_2$) were incubated in a reaction buffer composed of 20 mM Tris, 50 mM NaCl, MgCl$_2$ (5-25 mM depending on the kinase), 1 mM DTT, 0.1 mM EDTA, 0.01% bovine serum albumin, 0.005% Tween-20, and 10% DMSO at pH 7.4 for one hour. The reaction was quenched by the addition of 1.2 equivalents of EDTA (relative to Mg$^{2+}$) in 25 µL of 1x Lance buffer (Perkin-Elmer). Streptavidin-APC (Perkin-Elmer) and Eu-labeled p-Tyr100 antibody (Perkin-Elmer) in 1x Lance buffer were added in a 25 µL volume to give final concentrations of 100 nM and 2.5 nM, respectively, and the mixture was allowed to incubate for one hour. The TR-FRET signal was measured on a multimode plate reader with an excitation wavelength of 330 nm and detection wavelengths of 615 nm and 665 nm. Activity was determined by the ratio of the fluorescence at 665 nm to that at 615 nm. For each compound, enzyme activity was measured at various concentrations of compound. Negative control reactions were performed in the absence of inhibitor in replicates of six, and two no-enzyme controls were used to determine baseline fluorescence levels. Inhibition constants were obtained using the program BatchKi (Kuzmic et al. *Anal. Biochem.* 2000, 286, 45-50). IC$_{50}$s were obtained according to this equation: IC$_{50}$={Ki (app)/(1+[ATP]/K$_m^{ATP}$)}+[E]$_{total}$/2; for all kinases, [ATP]=K$_m^{ATP}$, [Btk]$_{total}$=0.5 nM and [Lck]$_{total}$=6 nM.

Cellular calcium flux assays were done according to manufacturer descriptions (Molecular Devices). In brief, actively growing Ramos B-cells (ATCC) in RPM1 medium supplemented with 10% FBS (Invitrogen) were washed and replated in low serum medium to approximately 5×10⁵ cells per 100 ul per well in 96-well plate. Compounds to be assayed were dissolved in DMSO, diluted to appropriate concentrations in low serum medium (from 0 to 10 µM final concentrations at a dilution factor of 0.3), added to each well (the final DMSO concentration was 0.01% in each well) and incubated at 37 degree in 5% CO$_2$ incubator for 1 hour. 100 ul calcium assay dye (Calcium 3 assay kit, Molecular Devices) was then added to each well and incubated for an additional one hour. The compound treated cells were stimulated with a goat anti-human IgM antibody (80 ug/ml; Jackson Inmmunoresearch) and read in a Flexstation II384 (Molecular Devices) at Ex=485nm and Em=538nm for 200 seconds. The relative fluorescence unit (RFU) and the fifty percent of inhibition (IC50%) were recorded and analyzed using a built-in SoftMax program (Molecular devices).

Data for both kinase and cellular calcium flux assays are shown in Table 7. All values are shown in µM units.

TABLE 7

| Assay Data for Representative Compounds | |
|---|---|
| Cmpd No. | Btk-TRFRET (Ki) |
| 1 | A |
| 2 | A |
| 3 | A |
| 4 | A |
| 5 | A |
| 6 | A |
| 7 | B |
| 8 | B |
| 9 | B |
| 10 | A |
| 11 | A |
| 12 | A |
| 13 | A |

TABLE 7-continued

Assay Data for Representative Compounds

| Cmpd No. | Btk-TRFRET (Ki) |
|---|---|
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 40 | C |
| 41 | B |
| 42 | A |
| 43 | A |
| 44 | A |
| 45 | B |
| 46 | C |
| 47 | B |
| 48 | B |
| 49 | B |
| 50 | B |
| 51 | B |

A = < 100 nM; B = >100 nM and <1000 nM; C = >1000 Nm; nd = not determined

Example 12

Pharmaceutical Compositions

Example 12a

Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
|---|---|
| compound described herein | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60-70° C. with stirring. A sufficient quantity of water at 60° C. is then added with vigorous stirring to emulsify the ingredients, and water then added q.s. to 100 g.

Example 12b

Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

In another embodiment, the following ingredients are mixed intimately and pressed into single scored tablets:

| Ingredient | Quantity per tablet, mg |
|---|---|
| compound described herein | 400 |
| cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
|---|---|
| compound described herein | 200 |
| lactose, spray-dried | 148 |
| magnesium stearate | 2 |

In some other embodiments, the following ingredients are mixed to form a suspension for oral administration:

| Ingredient | Amount |
|---|---|
| compound described herein | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Example 12c

Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 12d

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administ

2. The compound of claim 1, wherein:

T is 1,6-dimethyl-9-oxo-8,9-dihydro-1H-imidazo[4,5-h]isoquinolin-2,7-ylene substituted at the 2 position with

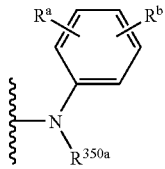

and substituted at the 7 position with

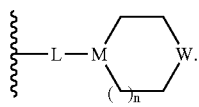

3. The compound of claim 2, wherein $Y^{250}$ is a bond, —O—, —S(=O)—, —S(=O)$_2$—, —C(=)—, —NH—, —NHC(=O)—, —NHC(=O)NH—, —C(=O)NH—, —OC(=O)—, —C(=O)O—, —NHSO$_2$—, —SO$_2$NH—, —NHC(=O)O—, or —OC(=O)NH—;

E is O; and $R^{350a}$ is hydrogen, a substituted or unsubstituted $C_1$-$C_6$alkyl, or a substituted or unsubstituted $C_1$-$C_6$haloalkyl.

4. The compound of claim 3, wherein $X^{250a}$ is a substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl; and n is 1.

5. The compound of claim 4, wherein compound has a structure selected from among:

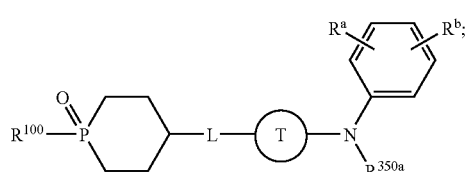

Formula (IIIa)

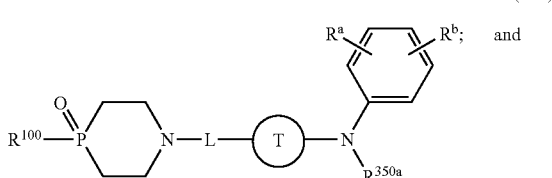

Formula (IIIb) and

-continued

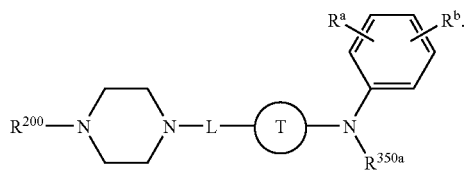

Formula (IIIc)

6. The compound of claim 5, wherein:

$R^{100}$ is halogen, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-Cycloalkyl), $C_2$-$C_8$heterocycloalkyl, and $C_1$-$C_4$alkyl($C_2$-$C_8$heterocycloalky);

$R^{200}$ is an optionally substituted group selected from among $C_2$-$C_{10}$acyl, $C_1$-$C_6$alkylsulfonyl, $C_2$-$C_6$alkenylsulfonyl, arylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

7. The compound of claim 6, wherein:

$R^{350a}$ is hydrogen;

$Y^{250}$ is a bond, —C(=O)—, —NHC(=O)—, —C(=O)NH—.

8. The compound of claim 7, wherein L is selected from among:

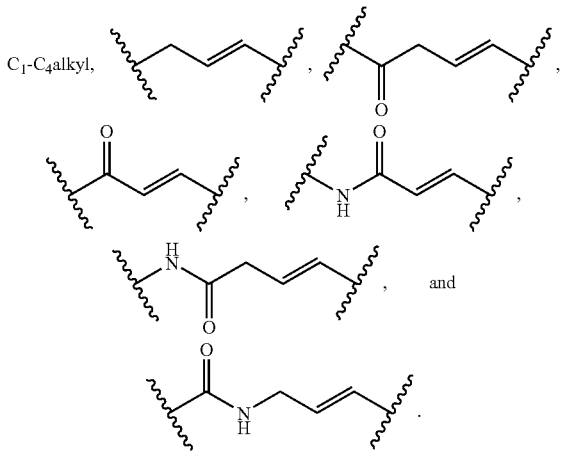

9. The compound of claim 8, wherein the compound has a structure of Formula (IIIc).

10. The compound of claim 9, wherein:

L is $C_1$-$C_4$alkyl or

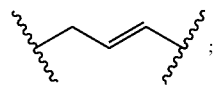

and $R^{200}$ is an optionally substituted group selected from among $C_2$-$C_{10}$acyl, aryl, $C_1$-$C_6$alkylsulfonyl, $C_2$-$C_6$alkenylsulfonyl, arylsulfonyl, C₁-C₁₀alkoxycarbonyl, aminosulfonyl, C₁-C₆alkylaminosulfonyl, and di(C₁-C₆alkyl)aminosulfonyl.

11. The compound of claim 1, wherein: T is 1,7-dimethyl-9-oxo-8,9-dihydro-1H-imidazo[4,5-h]isoquinolin-2,6-ylene substituted at the 2 position with

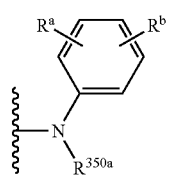

and substituted at the 6 position with

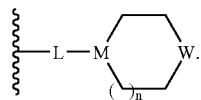

12. The compound of claim 11, wherein Y²⁵⁰ is a bond, —O—, —S(=O)—, —S(=O)₂—, —C(=O)—, —NH—, —NHC(=O)—, —NHC(=O)NH—, —C(=O)NH—, —OC(=O)—, —C(=O)O—, —NHSO₂—, —SO₂NH—, —NHC(=O)O—, or —OC(=O)NH—;
E is O; and
R³⁵⁰ᵃ is hydrogen, or a substituted or unsubstituted C₁-C₆alkyl.

13. The compound of claim 12, wherein X²⁵⁰ᵃ is a substituted or unsubstituted C₁-C₆alkyl, substituted or unsubstituted C₁-C₆haloalkyl, substituted or unsubstituted C₂-C₆alkenyl, substituted or unsubstituted C₂-C₆haloalkenyl, substituted or unsubstituted C₂-C₆alkynyl, or substituted or unsubstituted C₂-C₆haloalkynyl; and
n is 1.

14. The compound of claim 13, wherein compound has a structure selected from among:

Formula (IIIa)

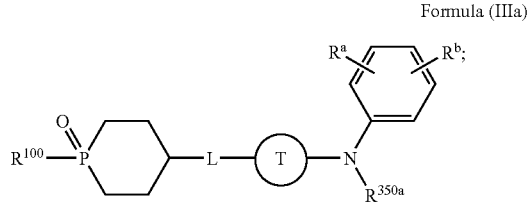

-continued

Formula (IIIb)

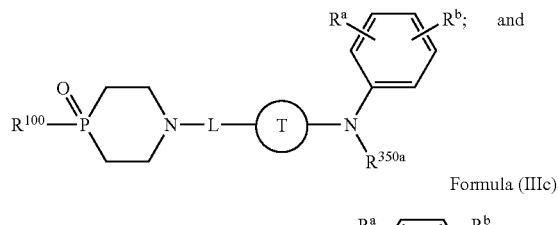
and

Formula (IIIc)

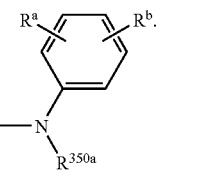

15. The compound of claim 14, wherein:
R¹⁰⁰ is halogen, or an optionally substituted group selected from among C₁-C₆alkyl, C₂-C₆alkenyl, C₂-C₆alkynyl, phenyl, C₁-C₄alkyl(phenyl), C₃-C₈cycloalkyl, C₁-C₄alkyl(C₃-C₈cycloalkyl), C₂-C₈heterocycloalkyl, and C₁-C₄alkyl(C₂-C₈heterocycloalkyl);
R²⁰⁰ is an optionally substituted group selected from among C₂-C₁₀acyl, C₁-C₆alkylsulfonyl, C₂-C₆alkenylsulfonyl, arylsulfonyl, C₁-C₁₀alkoxycarbonyl, aminosulfonyl, C₁-C₆alkylaminosulfonyl, and di(C₁-C₆alkyl)aminosulfonyl.

16. The compound of claim 15, wherein:
R³⁵⁰ᵃ is hydrogen;
Y²⁵⁰ is —C(=O)—; and
X²⁵⁰ᵃ is a substituted or unsubstituted C₁-C₆alkyl.

17. The compound of claim 16, wherein L is

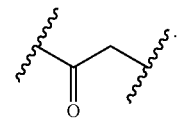

18. The compound of claim 17, wherein the compound has a structure of Formula (IIIb).

19. A pharmaceutical composition comprising a therapeutically effective amount of a compound of claim 1 and a pharmaceutically acceptable excipient.

20. The pharmaceutical composition of claim 19, wherein the composition is formulated for oral administration.

* * * * *

UNITED STATES PATENT AND TRADEMARK OFFICE
CERTIFICATE OF CORRECTION

PATENT NO. : 7,625,880 B2
APPLICATION NO. : 11/617651
DATED : December 1, 2009
INVENTOR(S) : Orion D. Jankowski et al.

It is certified that error appears in the above-identified patent and that said Letters Patent is hereby corrected as shown below:

Col. 155, line 54,

Claim 1:

A compound of Formula (III):

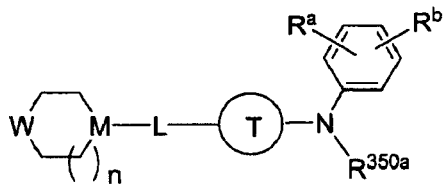

wherein:

$R^a$ and $R^b$ are each independently selected from among H, halogen, CN, $NO_2$, $C_1$-$C_4$alkyl, $C_1$-$C_4$haloalkyl, and $C_1$-$C_4$alkoxy;

T is 1,6-dimethyl-9-oxo-8,9-dihydro-1H-imidazo[4,5-h]isoquinolin-2,7-ylene, or 1,7-dimethyl-9-oxo-8,9-dihydro-1H-imidazo[4,5-h]isoquinolin-2,6-ylene;

L is -$X^{250a}$-$Y^{250}$- or -$Y^{250}$-$X^{250a}$-, wherein, $X^{250a}$ is a substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;

$Y^{250}$ is a bond, -O-, -S(=O)-, -S(=O)$_2$-, -C(=O)-, -$NR^{45}$-, -NH-, -NHC(=O)-, $NR^{45}$C(=O)-, -$NR^{45}$C(=O)$NR^{45}$-, -C(=O)NH-, -C(=O)$NR^{45}$-, -OC(=O)-, -C(=O)O-, -$NHSO_2$-, -$NR^{45}SO_2$-, -$SO_2$NH-, -$SO_2NR^{45}$-, -C($R^{45}$)=NO-, -CH=NO-, -ON=CH-, aryl, -NHC(=O)O-, -OC(=O)NH-, -$NR^{45}$C(=O)O-, or -OC(=O)$NR^{45}$-;

Signed and Sealed this
Fifteenth Day of March, 2011

David J. Kappos
*Director of the United States Patent and Trademark Office*

CERTIFICATE OF CORRECTION (continued)

where each $R^{45}$ is independently selected from among hydrogen, substituted or unsubstituted $C_1$-$C_6$alkyl, substituted or unsubstituted $C_3$-$C_8$cycloalkyl, substituted or unsubstituted $C_2$-$C_6$alkenyl, substituted or unsubstituted $C_2$-$C_6$alkynyl;

M is N or CH;

W is 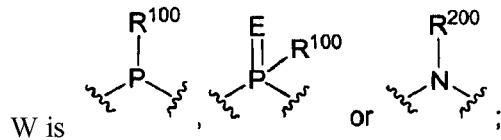 ;

E is oxygen or sulfur;

$R^{100}$ is halogen, -OH, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-Cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), $C_1$-$C_6$alkoxy, $C_1$-$C_6$alkenyloxy, $C_1$-$C_6$alkynyloxy, or -$NR^{102a}R^{102b}$;

$R^{102a}$ and $R^{102b}$ are independently hydrogen, or an optionally substituted group selected from among $C_1$-$C_6$alkyl, $C_2$-$C_6$alkenyl, $C_2$-$C_6$alkynyl, aryl, aralkyl, $C_3$-$C_8$cycloalkyl, $C_1$-$C_4$alkyl($C_3$-$C_8$cycloalkyl), $C_2$-$C_8$heterocycloalkyl, and $C_1$-$C_4$alkyl($C_2$-$C_8$heterocycloalkyl);

$R^{200}$ is an optionally substituted group selected from among $C_2$-$C_{10}$acyl, aryl, $C_1$-$C_6$alkylsulfonyl, $C_2$-$C_6$alkenylsulfonyl, arylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl;

$R^{350a}$ is hydrogen, a substituted or unsubstituted $C_1$-$C_6$alkyl, a substituted or unsubstituted $C_2$-$C_8$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl;

n is 1; or a pharmaceutically acceptable salt, or a pharmaceutically acceptable prodrug thereof.

Should read as follows:

Claim 1:

A compound of Formula (III):

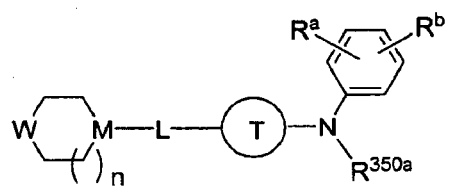

wherein:

$R^a$ and $R^b$ are each independently selected from among H, halogen, CN, $NO_2$, $C_1$-$C_4$alkyl, $C_1$-$C_4$haloalkyl, and $C_1$-$C_4$alkoxy;

T is 1,6-dimethyl-9-oxo-8,9-dihydro-1H-imidazo[4,5-h]isoquinolin-2,7-ylene, or 1,7-dimethyl-9-oxo-8,9-dihydro-1H-imidazo[4,5-h]isoquinolin-2,6-ylene;

L is $-X^{250a}-Y^{250}-$ or $-Y^{250}-X^{250a}-$, wherein, $X^{250a}$ is a substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_5$-$C_8$cycloalkenyl, substituted or unsubstituted $C_2$-$C_6$alkenyl, substituted or unsubstituted $C_2$-$C_6$haloalkenyl, substituted or unsubstituted $C_2$-$C_6$alkynyl, or substituted or unsubstituted $C_2$-$C_6$haloalkynyl;

$Y^{250}$ is a bond, -O-, -S(=O)-, -S(=O)$_2$-, -C(=O)-, $-NR^{45}-$, -NH-, -NHC(=O)-, $-NR^{45}C(=O)-$, $-NR^{45}C(=O)NR^{45}-$, -C(=O)NH-, $-C(=O)NR^{45}-$, -OC(=O)-, -C(=O)O-, -NHSO$_2$-, $-NR^{45}SO_2-$, -SO$_2$NH-, $-SO_2NR^{45}-$, $-C(R^{45})=NO-$, -CH=NO-, -ON=CH-, aryl, -NHC(=O)O-, -OC(=O)NH-, $-NR^{45}C(=O)O-$, or $-OC(=O)NR^{45}-$;

where each $R^{45}$ is independently selected from among hydrogen, substituted or unsubstituted $C_1$-$C_6$alkyl, substituted or unsubstituted $C_3$-$C_8$cycloalkyl, substituted or unsubstituted $C_2$-$C_6$alkenyl, substituted or unsubstituted $C_2$-$C_6$alkynyl;

M is N or CH;

W is 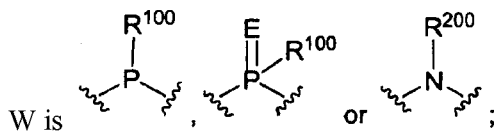

E is oxygen or sulfur;

$R^{100}$ is halogen, -OH, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-$C_8$cycloalkyl), $C_2$-$C_8$heterocycloalkyl, $C_1$-$C_4$alkyl($C_2$-$C_8$heterocycloalkyl), $C_1$-$C_6$alkoxy, $C_1$-$C_6$alkenyloxy, $C_1$-$C_6$alkynyloxy, or $-NR^{102a}R^{102b}$;

$R^{102a}$ and $R^{102b}$ are independently hydrogen, or an optionally substituted group selected from among $C_1$-$C_6$alkyl, $C_2$-$C_6$alkenyl, $C_2$-$C_6$alkynyl, aryl, aralkyl, $C_3$-$C_8$cycloalkyl, $C_1$-$C_4$alkyl($C_3$-$C_8$cycloalkyl), $C_2$-$C_8$heterocycloalkyl, and $C_1$-$C_4$alkyl($C_2$-$C_8$heterocycloalkyl);

CERTIFICATE OF CORRECTION (continued)

U.S. Pat. No. 7,625,880 B2

$R^{200}$ is an optionally substituted group selected from among $C_2$-$C_{10}$acyl, aryl, $C_1$-$C_6$alkylsulfonyl, $C_2$-$C_6$alkenylsulfonyl, arylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl;

$R^{350a}$ is hydrogen, a substituted or unsubstituted $C_1$-$C_6$alkyl, a substituted or unsubstituted $C_2$-$C_6$alkenyl, a substituted or unsubstituted $C_2$-$C_6$alkynyl, a substituted or unsubstituted $C_1$-$C_6$haloalkyl, a substituted or unsubstituted $C_2$-$C_6$haloalkenyl, or a substituted or unsubstituted $C_2$-$C_6$haloalkynyl;

n is 1; or a pharmaceutically acceptable salt, or a pharmaceutically acceptable prodrug thereof.

Col. 158, line 13,

Claim 6:

The compound of claim 5, wherein:

$R^{100}$ is halogen, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-Cycloalkyl), $C_2$-$C_8$heterocycloalkyl, and $C_1$-$C_4$alkyl($C_2$-$C_8$heterocycloalkyl);

$R^{200}$ is an optionally substituted group selected from among $C_2$-$C_{10}$acyl, aryl, $C_1$-$C_6$alkylsulfonyl, $C_2$-$C_6$alkenylsulfonyl, arylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.

Should read as follows:

Claim 6:

The compound of claim 5, wherein:

$R^{100}$ is halogen, or an optionally substituted group selected from among $C_1$-$C_6$alkyl, $C_2$-$C_6$alkenyl, $C_2$-$C_6$alkynyl, phenyl, $C_1$-$C_4$alkyl(phenyl), $C_3$-$C_8$cycloalkyl, $C_1$-$C_4$alkyl($C_3$-$C_8$cycloalkyl), $C_2$-$C_8$heterocycloalkyl, and $C_1$-$C_4$alkyl($C_2$-$C_8$heterocycloalkyl);

$R^{200}$ is an optionally substituted group selected from among $C_2$-$C_{10}$acyl, aryl, $C_1$-$C_6$alkylsulfonyl, $C_2$-$C_6$alkenylsulfonyl, arylsulfonyl, $C_1$-$C_{10}$alkoxycarbonyl, aminosulfonyl, $C_1$-$C_6$alkylaminosulfonyl, and di($C_1$-$C_6$alkyl)aminosulfonyl.